(12) United States Patent (10) Patent No.: US 8,163,164 B2
Feldman et al. (45) Date of Patent: *Apr. 24, 2012

(54) SMALL VOLUME IN VITRO ANALYTE SENSOR AND METHODS OF MAKING

(75) Inventors: Benjamin J. Feldman, Oakland, CA (US); Adam Heller, Austin, TX (US); Ephraim Heller, Piedmont, CA (US); Fei Mao, Fremont, CA (US); Joseph A. Vivolo, San Francisco, CA (US); Jeffery V. Funderburk, Stevenson Ranch, CA (US); Fredric C. Colman, Woodside, CA (US); Rajesh Krishnan, San Leandro, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/569,141

(22) Filed: Sep. 29, 2009

(65) Prior Publication Data

US 2010/0081907 A1 Apr. 1, 2010

Related U.S. Application Data

(60) Continuation of application No. 11/734,979, filed on Apr. 13, 2007, which is a division of application No. 10/662,081, filed on Sep. 12, 2003, now Pat. No. 7,225,535, which is a division of application No. 09/594,285, filed on Jun. 15, 2000, now Pat. No. 6,618,934, which is a continuation of application No. 09/295,962, filed on Apr. 21, 1999, now Pat. No. 6,338,790.

(60) Provisional application No. 60/103,627, filed on Oct. 8, 1998, provisional application No. 60/105,773, filed on Oct. 8, 1998.

(51) Int. Cl.
 *G01N 27/327* (2006.01)

(52) U.S. Cl. .................................. 205/792; 205/777.5
(58) Field of Classification Search .............. 204/403.01–403.15; 205/777.5, 205/778, 792
 See application file for complete search history.

(56) References Cited

U.S. PATENT DOCUMENTS 3,260,656 A 7/1966 Ross, Jr.
(Continued)

FOREIGN PATENT DOCUMENTS

DE 2903216 8/1979
(Continued)

OTHER PUBLICATIONS

*Therasense, Inc.*, v. *Becton, Dickinson and Co.*, 560 F. Supp. 2d 835—Dist. Court, ND California 2008, Apr. 3, 2008.*

(Continued)

*Primary Examiner* — Alex Noguerola
(74) *Attorney, Agent, or Firm* — Edward J. Baba; Brian E. Davy; Bozicevic, Field & Francis LLP

(57) ABSTRACT

A sensor utilizing a non-leachable or diffusible redox mediator is described. The sensor includes a sample chamber to hold a sample in electrolytic contact with a working electrode, and in at least some instances, the sensor also contains a non-leachable or a diffusible second electron transfer agent. The sensor and/or the methods used produce a sensor signal in response to the analyte that can be distinguished from a background signal caused by the mediator. The invention can be used to determine the concentration of a biomolecule, such as glucose or lactate, in a biological fluid, such as blood or serum, using techniques such as coulometry, amperometry; and potentiometry. An enzyme capable of catalyzing the electrooxidation or electroreduction of the biomolecule is typically provided as a second electron transfer agent.

20 Claims, 28 Drawing Sheets

U.S. PATENT DOCUMENTS

| | | |
|---|---|---|
| 3,506,544 A | 4/1970 | Silverman et al. |
| 3,623,960 A | 11/1971 | Williams |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,205 A | 10/1978 | Ripphahn et al. |
| 4,133,735 A | 1/1979 | Afromowitz et al. |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,210,156 A | 7/1980 | Bennett |
| 4,216,245 A | 8/1980 | Johnson |
| 4,224,125 A | 9/1980 | Nakamura et al. |
| 4,225,410 A | 9/1980 | Pace |
| 4,240,438 A | 12/1980 | Updike et al. |
| 4,240,889 A | 12/1980 | Yoda et al. |
| 4,244,800 A * | 1/1981 | Frazzini et al. ............... 204/406 |
| 4,247,297 A | 1/1981 | Berti et al. |
| 4,271,119 A | 6/1981 | Columbus |
| 4,318,784 A | 3/1982 | Higgins et al. |
| 4,339,317 A | 7/1982 | Meiattini et al. |
| 4,340,458 A | 7/1982 | Lerner et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,388,166 A | 6/1983 | Suzuki et al. |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,418,148 A | 11/1983 | Oberhardt |
| 4,420,564 A | 12/1983 | Tsuji et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,462,405 A | 7/1984 | Ehrlich |
| 4,469,110 A | 9/1984 | Slama |
| 4,477,314 A | 10/1984 | Richter et al. |
| 4,483,924 A | 11/1984 | Tsuji et al. |
| 4,484,987 A | 11/1984 | Gough |
| 4,490,464 A | 12/1984 | Gorton et al. |
| 4,492,622 A * | 1/1985 | Kuypers ................... 204/403.07 |
| 4,496,454 A | 1/1985 | Berger |
| 4,522,690 A | 6/1985 | Venkatasetty |
| 4,524,114 A | 6/1985 | Samuels et al. |
| 4,526,661 A | 7/1985 | Steckhan et al. |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,615,340 A | 10/1986 | Cronenberg et al. |
| 4,619,754 A | 10/1986 | Niki et al. |
| 4,627,445 A | 12/1986 | Garcia et al. |
| 4,627,908 A | 12/1986 | Miller |
| 4,629,563 A | 12/1986 | Wrasidlo |
| 4,633,878 A | 1/1987 | Bombardieri |
| 4,637,403 A | 1/1987 | Garcia et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,750,496 A | 6/1988 | Reinhart et al. |
| 4,757,022 A | 7/1988 | Shults et al. |
| 4,758,323 A | 7/1988 | Davis et al. |
| 4,759,371 A | 7/1988 | Franetski |
| 4,759,828 A | 7/1988 | Young et al. |
| 4,764,416 A | 8/1988 | Ueyama et al. |
| 4,764,485 A | 8/1988 | Loughran et al. |
| 4,776,944 A | 10/1988 | Janata et al. |
| 4,781,798 A | 11/1988 | Gough |
| 4,784,736 A | 11/1988 | Lonsdale et al. |
| 4,787,398 A | 11/1988 | Garcia et al. |
| 4,795,707 A | 1/1989 | Niiyama et al. |
| 4,796,634 A | 1/1989 | Huntsman |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| RE32,922 E | 5/1989 | Levin et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,895,479 A | 1/1990 | Michaelsen et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,274 A | 4/1990 | Asa et al. |
| 4,917,800 A | 4/1990 | Lonsdale et al. |
| 4,919,141 A | 4/1990 | Zier et al. |
| 4,919,767 A | 4/1990 | Vadgama et al. |
| 4,923,586 A | 5/1990 | Katayama et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,968,400 A | 11/1990 | Shimomura et al. |

| | | | | | | |
|---|---|---|---|---|---|---|
| 4,969,468 A | 11/1990 | Byers et al. | | 5,288,636 A | 2/1994 | Pollmann et al. |
| 4,970,145 A | 11/1990 | Bennetto et al. | | 5,293,546 A | 3/1994 | Tadros et al. |
| 4,974,929 A | 12/1990 | Curry | | 5,298,144 A | 3/1994 | Spokane |
| 4,986,271 A | 1/1991 | Wilkins | | 5,310,885 A | 5/1994 | Maier et al. |
| 4,994,167 A | 2/1991 | Shults et al. | | 5,312,527 A | 5/1994 | Mikkelsen et al. |
| 5,001,054 A | 3/1991 | Wagner | | 5,318,584 A | 6/1994 | Lange et al. |
| 5,025,798 A | 6/1991 | Schindele | | 5,320,098 A | 6/1994 | Davidson |
| 5,034,192 A | 7/1991 | Wrighton et al. | | 5,320,725 A | 6/1994 | Gregg et al. |
| 5,037,527 A | 8/1991 | Hayashi et al. | | 5,320,732 A | 6/1994 | Nankai et al. |
| 5,058,592 A | 10/1991 | Whisler | | 5,322,063 A | 6/1994 | Allen et al. |
| 5,059,290 A | 10/1991 | Uchiyama et al. | | 5,325,853 A | 7/1994 | Morris et al. |
| 5,070,535 A | 12/1991 | Hochmair et al. | | 5,326,449 A | 7/1994 | Cunningham |
| 5,078,854 A | 1/1992 | Burgess et al. | | 5,337,747 A | 8/1994 | Neftel |
| 5,082,550 A | 1/1992 | Rishpon et al. | | 5,352,348 A | 10/1994 | Young et al. |
| 5,082,786 A | 1/1992 | Nakamoto | | 5,352,351 A | 10/1994 | White et al. |
| 5,089,112 A | 2/1992 | Skotheim et al. | | 5,354,447 A | 10/1994 | Uenoyama et al. |
| 5,089,320 A * | 2/1992 | Straus et al. ................ 428/216 | | 5,356,786 A | 10/1994 | Heller et al. |
| 5,094,951 A | 3/1992 | Rosenberg | | 5,364,797 A | 11/1994 | Olson et al. |
| 5,095,407 A | 3/1992 | Kanezawa et al. | | 5,366,609 A | 11/1994 | White et al. |
| 5,095,904 A | 3/1992 | Seligman et al. | | 5,368,028 A | 11/1994 | Palti |
| 5,096,560 A | 3/1992 | Takai et al. | | 5,372,133 A | 12/1994 | Hogen Esch |
| 5,096,836 A | 3/1992 | Macho et al. | | 5,376,251 A | 12/1994 | Kaneko et al. |
| 5,101,814 A | 4/1992 | Palti | | 5,378,628 A | 1/1995 | Gratzel et al. |
| 5,104,813 A | 4/1992 | Besemer et al. | | 5,380,422 A | 1/1995 | Negishi et al. |
| 5,108,564 A | 4/1992 | Szuminsky et al. | | 5,382,346 A | 1/1995 | Uenoyama et al. |
| 5,108,889 A | 4/1992 | Smith et al. | | 5,387,327 A | 2/1995 | Khan |
| 5,109,850 A | 5/1992 | Blanco et al. | | 5,387,329 A | 2/1995 | Foos et al. |
| 5,112,455 A | 5/1992 | Cozzette et al. | | 5,390,671 A | 2/1995 | Lord et al. |
| 5,120,420 A | 6/1992 | Nankai et al. | | 5,391,250 A | 2/1995 | Cheney, II et al. |
| 5,120,421 A | 6/1992 | Glass et al. | | 5,393,903 A | 2/1995 | Gratzel et al. |
| 5,126,034 A | 6/1992 | Carter et al. | | 5,395,504 A | 3/1995 | Saurer et al. |
| 5,126,247 A | 6/1992 | Palmer et al. | | 5,411,647 A | 5/1995 | Johnson et al. |
| 5,128,015 A | 7/1992 | Szuminsky et al. | | 5,413,690 A | 5/1995 | Kost et al. |
| 5,130,009 A | 7/1992 | Marsoner et al. | | 5,422,246 A | 6/1995 | Koopal et al. |
| 5,133,856 A | 7/1992 | Yamaguchi et al. | | 5,424,035 A | 6/1995 | Hones et al. |
| 5,135,003 A | 8/1992 | Souma | | 5,437,973 A | 8/1995 | Vadgama et al. |
| 5,140,393 A | 8/1992 | Hijikihigawa et al. | | 5,437,999 A | 8/1995 | Diebold et al. |
| 5,141,868 A | 8/1992 | Shanks et al. | | 5,438,271 A | 8/1995 | White et al. |
| 5,161,532 A | 11/1992 | Joseph | | 5,469,846 A | 11/1995 | Khan |
| 5,165,407 A | 11/1992 | Wilson et al. | | 5,478,751 A | 12/1995 | Oosta et al. |
| 5,168,046 A | 12/1992 | Hamamoto et al. | | 5,494,562 A | 2/1996 | Maley et al. |
| 5,174,291 A | 12/1992 | Schoonen et al. | | 5,496,453 A | 3/1996 | Uenoyama et al. |
| 5,185,256 A | 2/1993 | Nankai et al. | | 5,497,772 A | 3/1996 | Schulman et al. |
| 5,190,041 A | 3/1993 | Palti | | 5,501,956 A | 3/1996 | Wada et al. |
| 5,192,415 A | 3/1993 | Yoshioka et al. | | 5,502,396 A | 3/1996 | Desarzens et al. |
| 5,192,416 A | 3/1993 | Wang et al. | | 5,507,288 A | 4/1996 | Bocker et al. |
| 5,198,367 A | 3/1993 | Aizawa et al. | | 5,508,171 A | 4/1996 | Walling et al. |
| 5,200,051 A | 4/1993 | Cozzette et al. | | 5,508,200 A | 4/1996 | Tiffany et al. |
| 5,201,324 A | 4/1993 | Swierczek | | 5,509,410 A | 4/1996 | Hill et al. |
| 5,202,261 A | 4/1993 | Musho et al. | | 5,510,266 A | 4/1996 | Bonner et al. |
| 5,205,920 A | 4/1993 | Oyama et al. | | 5,512,159 A | 4/1996 | Yoshioka et al. |
| 5,206,145 A | 4/1993 | Cattell | | 5,514,253 A | 5/1996 | Davis et al. |
| 5,206,147 A | 4/1993 | Hoenes | | 5,518,006 A | 5/1996 | Mawhirt et al. |
| 5,208,154 A | 5/1993 | Weaver et al. | | 5,520,787 A | 5/1996 | Hanagan et al. |
| 5,209,229 A | 5/1993 | Gilli | | 5,525,511 A | 6/1996 | D'Costa |
| 5,217,480 A | 6/1993 | Haber et al. | | 5,526,120 A | 6/1996 | Jina et al. |
| 5,217,595 A | 6/1993 | Smith et al. | | 5,531,878 A | 7/1996 | Vadgama et al. |
| 5,223,321 A | 6/1993 | Sinnadurai et al. | | 5,545,191 A | 8/1996 | Mann et al. |
| 5,227,042 A | 7/1993 | Zawodzinski et al. | | 5,547,555 A | 8/1996 | Schwartz et al. |
| 5,229,282 A | 7/1993 | Yoshioka et al. | | 5,552,027 A | 9/1996 | Birkle et al. |
| 5,230,786 A | 7/1993 | Preidel | | 5,556,524 A | 9/1996 | Albers |
| 5,250,439 A | 10/1993 | Musho et al. | | 5,560,357 A | 10/1996 | Faupel et al. |
| 5,262,035 A | 11/1993 | Gregg et al. | | 5,565,085 A | 10/1996 | Ikeda et al. |
| 5,262,305 A | 11/1993 | Heller et al. | | 5,567,302 A | 10/1996 | Song et al. |
| 5,264,103 A | 11/1993 | Yoshioka et al. | | 5,568,186 A | 10/1996 | Althouse |
| 5,264,104 A | 11/1993 | Gregg et al. | | 5,568,806 A | 10/1996 | Cheney, II et al. |
| 5,264,105 A | 11/1993 | Gregg et al. | | 5,569,186 A | 10/1996 | Lord et al. |
| 5,264,106 A | 11/1993 | McAleer et al. | | 5,575,403 A | 11/1996 | Charlton et al. |
| 5,266,179 A * | 11/1993 | Nankai et al. ................ 204/401 | | 5,575,895 A | 11/1996 | Ikeda et al. |
| 5,269,891 A | 12/1993 | Colin | | 5,580,527 A | 12/1996 | Bell et al. |
| 5,271,815 A | 12/1993 | Wong | | 5,582,184 A | 12/1996 | Erickson et al. |
| 5,272,060 A | 12/1993 | Hamamoto et al. | | 5,582,697 A * | 12/1996 | Ikeda et al. ................ 205/777.5 |
| 5,276,294 A | 1/1994 | Jalbert | | 5,582,698 A | 12/1996 | Flaherty et al. |
| 5,278,079 A | 1/1994 | Gubinski et al. | | 5,586,553 A | 12/1996 | Halili et al. |
| 5,279,294 A | 1/1994 | Anderson et al. | | 5,589,045 A | 12/1996 | Hyodo |
| 5,280,551 A | 1/1994 | Bowen | | 5,589,326 A | 12/1996 | Deng et al. |
| 5,282,950 A | 2/1994 | Dietze et al. | | 5,593,852 A | 1/1997 | Heller et al. |
| 5,286,362 A | 2/1994 | Hoenes et al. | | 5,595,479 A | 1/1997 | Hansen et al. |
| 5,286,364 A | 2/1994 | Yacynych et al. | | 5,596,150 A | 1/1997 | Arndt et al. |

| | | | | | | |
|---|---|---|---|---|---|---|
| 5,601,694 | A | 2/1997 | Maley et al. | D427,312 | S | 6/2000 | Douglas |
| 5,611,900 | A | 3/1997 | Worden et al. | 6,071,249 | A | 6/2000 | Cunningham et al. |
| 5,617,851 | A | 4/1997 | Lipkovker | 6,071,251 | A | 6/2000 | Cunningham et al. |
| 5,628,890 | A | 5/1997 | Carter et al. | 6,071,391 | A | 6/2000 | Gotoh et al. |
| 5,630,986 | A | 5/1997 | Charlton et al. | 6,093,156 | A | 7/2000 | Cunningham et al. |
| 5,632,410 | A | 5/1997 | Moulton et al. | 6,099,484 | A | 8/2000 | Douglas et al. |
| 5,650,002 | A | 7/1997 | Bolt | 6,103,033 | A | 8/2000 | Say et al. |
| 5,650,062 | A | 7/1997 | Ikeda et al. | 6,117,290 | A | 9/2000 | Say et al. |
| 5,651,869 | A | 7/1997 | Yoshioka et al. | 6,120,676 | A | 9/2000 | Heller et al. |
| 5,653,863 | A | 8/1997 | Genshaw et al. | 6,129,823 | A | 10/2000 | Hughes et al. |
| 5,658,443 | A | 8/1997 | Yamamoto et al. | 6,129,843 | A | 10/2000 | Petty et al. |
| 5,660,163 | A | 8/1997 | Schulman et al. | 6,132,580 | A | 10/2000 | Mathies et al. |
| 5,666,966 | A | 9/1997 | Horie et al. | 6,134,461 | A | 10/2000 | Say et al. |
| 5,670,031 | A | 9/1997 | Hintsche et al. | 6,143,164 | A | 11/2000 | Heller et al. |
| 5,680,858 | A | 10/1997 | Hansen et al. | 6,156,051 | A | 12/2000 | Schraga |
| 5,682,233 | A | 10/1997 | Brinda | 6,174,420 | B1 | 1/2001 | Hodges et al. |
| 5,682,884 | A | 11/1997 | Hill et al. | 6,179,979 | B1 | 1/2001 | Hodges et al. |
| 5,686,829 | A | 11/1997 | Girault | 6,190,398 | B1 | 2/2001 | Schraga |
| 5,695,623 | A | 12/1997 | Michel et al. | 6,192,891 | B1 | 2/2001 | Gravel et al. |
| 5,695,947 | A | 12/1997 | Guo et al. | 6,206,841 | B1 | 3/2001 | Cunningham et al. |
| 5,700,695 | A | 12/1997 | Yassinzadeh et al. | 6,210,420 | B1 | 4/2001 | Mauze et al. |
| 5,704,354 | A | 1/1998 | Preidel et al. | 6,283,926 | B1 | 9/2001 | Cunningham et al. |
| 5,707,502 | A | 1/1998 | McCaffrey et al. | 6,283,982 | B1 | 9/2001 | Levaughn et al. |
| 5,708,247 | A | 1/1998 | McAleer et al. | 6,284,125 | B1 | 9/2001 | Hodges et al. |
| 5,711,861 | A | 1/1998 | Ward et al. | 6,299,757 | B1 | 10/2001 | Feldman et al. |
| 5,711,862 | A | 1/1998 | Sakoda et al. | 6,306,104 | B1 | 10/2001 | Cunningham et al. |
| 5,720,862 | A | 2/1998 | Hamamoto et al. | 6,306,152 | B1 | 10/2001 | Verdonk et al. |
| 5,723,345 | A | 3/1998 | Yamauchi et al. | 6,338,790 | B1 | 1/2002 | Feldman et al. |
| 5,726,565 | A | 3/1998 | Uchiyama et al. | 6,346,114 | B1 | 2/2002 | Schraga |
| 5,727,548 | A | 3/1998 | Hill et al. | 6,352,514 | B1 | 3/2002 | Douglas et al. |
| 5,736,029 | A | 4/1998 | Pinkowski | 6,368,141 | B1 | 4/2002 | VanAntwerp et al. |
| 5,741,211 | A | 4/1998 | Renirie et al. | 6,409,740 | B1 | 6/2002 | Kuhr et al. |
| 5,741,688 | A | 4/1998 | Oxenboll et al. | 6,436,255 | B2 | 8/2002 | Yamamoto et al. |
| 5,743,861 | A | 4/1998 | Columbus et al. | 6,444,115 | B1 | 9/2002 | Hodges et al. |
| 5,746,217 | A | 5/1998 | Erickson et al. | 6,461,496 | B1 | 10/2002 | Feldman et al. |
| 5,767,480 | A | 6/1998 | Anglin et al. | 6,475,360 | B1 | 11/2002 | Hodges et al. |
| 5,770,028 | A | 6/1998 | Maley et al. | 6,506,168 | B1 | 1/2003 | Fathallah et al. |
| 5,781,455 | A | 7/1998 | Hyodo | 6,521,110 | B1 | 2/2003 | Hodges et al. |
| 5,786,584 | A | 7/1998 | Button et al. | 6,540,891 | B1 | 4/2003 | Stewart et al. |
| 5,791,344 | A | 8/1998 | Schulman et al. | 6,551,494 | B1 | 4/2003 | Heller et al. |
| 5,798,031 | A | 8/1998 | Charlton et al. | 6,576,101 | B1 | 6/2003 | Heller et al. |
| 5,800,420 | A | 9/1998 | Gross et al. | 6,591,125 | B1 | 7/2003 | Buse et al. |
| 5,801,057 | A | 9/1998 | Smart et al. | 6,592,745 | B1 | 7/2003 | Feldman et al. |
| 5,804,048 | A | 9/1998 | Wong et al. | 6,592,815 | B1 | 7/2003 | Zimmer |
| 5,807,375 | A | 9/1998 | Gross et al. | 6,599,407 | B2 | 7/2003 | Taniike et al. |
| 5,820,551 | A | 10/1998 | Hill et al. | 6,607,658 | B1 | 8/2003 | Heller et al. |
| 5,820,570 | A | 10/1998 | Erickson et al. | 6,616,819 | B1 | 9/2003 | Liamos et al. |
| 5,820,622 | A | 10/1998 | Gross et al. | 6,618,934 | B1 | 9/2003 | Feldman et al. |
| 5,830,341 | A | 11/1998 | Gilmartin | 6,630,415 | B2 | 10/2003 | Phillips et al. |
| 5,834,224 | A | 11/1998 | Ruger et al. | 6,632,349 | B1 | 10/2003 | Hodges et al. |
| 5,837,199 | A | 11/1998 | Dumschat | 6,740,215 | B1 | 5/2004 | Nakaminami et al. |
| 5,837,454 | A | 11/1998 | Cozzette et al. | 6,749,740 | B2 | 6/2004 | Liamos et al. |
| 5,842,983 | A | 12/1998 | Abel et al. | 6,764,581 | B1 | 7/2004 | Forrow et al. |
| 5,846,702 | A | 12/1998 | Deng et al. | 6,793,633 | B2 | 9/2004 | Douglas et al. |
| 5,846,744 | A | 12/1998 | Athey et al. | 6,863,800 | B2 | 3/2005 | Karinka et al. |
| 5,849,055 | A | 12/1998 | Arai et al. | 6,863,801 | B2 | 3/2005 | Hodges et al. |
| 5,857,983 | A | 1/1999 | Douglas et al. | 6,878,251 | B2 | 4/2005 | Hodges et al. |
| 5,873,990 | A | 2/1999 | Wojciechowski et al. | 6,885,196 | B2 | 4/2005 | Taniike et al. |
| 5,879,311 | A | 3/1999 | Duchon et al. | 6,939,450 | B2 | 9/2005 | Karinka et al. |
| 5,906,723 | A | 5/1999 | Mathies et al. | 6,942,518 | B2 | 9/2005 | Liamos et al. |
| 5,906,921 | A | 5/1999 | Ikeda et al. | 7,058,437 | B2 | 6/2006 | Buse et al. |
| 5,942,102 | A | 8/1999 | Hodges et al. | 7,063,771 | B2 | 6/2006 | Halabisky |
| 5,951,492 | A | 9/1999 | Douglas et al. | 7,063,776 | B2 | 6/2006 | Huang |
| 5,951,493 | A | 9/1999 | Douglas et al. | 7,125,481 | B2 | 10/2006 | Musho et al. |
| 5,951,836 | A | 9/1999 | McAleer et al. | 7,335,294 | B2 | 2/2008 | Heller et al. |
| 5,954,643 | A | 9/1999 | VanAntwerp et al. | 7,348,183 | B2 | 3/2008 | Fritsch et al. |
| 5,958,779 | A | 9/1999 | Bonnick et al. | 2003/0116447 | A1 | 6/2003 | Wilsey |
| 5,971,941 | A | 10/1999 | Simons et al. | 2003/0143113 | A2 | 7/2003 | Yuzhakov et al. |
| 5,989,409 | A | 11/1999 | Kurnik et al. | 2003/0155237 | A1 | 8/2003 | Wilsey |
| 5,997,708 | A | 12/1999 | Craig | 2004/0002682 | A1 | 1/2004 | Kovelman et al. |
| 5,997,817 | A | 12/1999 | Crismore et al. | 2004/0031682 | A1 | 2/2004 | Wilsey |
| 6,004,441 | A | 12/1999 | Fujiwara et al. | 2008/0277292 | A1 | 11/2008 | Heller et al. |
| 6,022,366 | A | 2/2000 | Schraga | 2010/0081907 | A1* | 4/2010 | Feldman et al. ............ 600/347 |
| 6,027,459 | A | 2/2000 | Shain et al. | | | | |
| 6,032,059 | A | 2/2000 | Henning et al. | | | FOREIGN PATENT DOCUMENTS | |
| 6,033,866 | A | 3/2000 | Guo et al. | DE | | 227029 | 9/1985 |
| 6,036,924 | A | 3/2000 | Simons et al. | DE | | 3934299 | 10/1990 |
| 6,045,676 | A | 4/2000 | Mathies et al. | DE | | 4234553 | 4/1993 |
| 6,063,039 | A | 5/2000 | Cunningham et al. | DE | | 29720299 | 1/1998 |

| | | |
|---|---|---|
| EP | 0010375 | 4/1980 |
| EP | 0026995 | 4/1981 |
| EP | 0048090 | 3/1982 |
| EP | 0078636 | 5/1983 |
| EP | 0080304 | 6/1983 |
| EP | 0096288 | 12/1983 |
| EP | 0136362 | 4/1984 |
| EP | 0125139 | 11/1984 |
| EP | 0127958 | 12/1984 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0286084 | 10/1988 |
| EP | 0359831 | 3/1990 |
| EP | 0368209 | 5/1990 |
| EP | 0390390 | 10/1990 |
| EP | 0400918 | 12/1990 |
| EP | 0453283 | 10/1991 |
| EP | 0470290 | 2/1992 |
| EP | 0470649 | 2/1992 |
| EP | 0537761 | 4/1993 |
| EP | 0781406 | 7/1997 |
| EP | 1060707 | 12/2000 |
| GB | 1318815 | 5/1973 |
| GB | 1394171 | 5/1975 |
| GB | 1599241 | 9/1981 |
| GB | 2073891 | 10/1981 |
| GB | 2154003 | 8/1985 |
| GB | 2204408 | 11/1988 |
| GB | 2254436 | 10/1992 |
| JP | 54-41191 | 4/1979 |
| JP | 55-10581 | 1/1980 |
| JP | 55-10583 | 1/1980 |
| JP | 55-10584 | 1/1980 |
| JP | 55-12406 | 1/1980 |
| JP | 56-163447 | 12/1981 |
| JP | 57-70448 | 4/1982 |
| JP | 57-98853 | 6/1982 |
| JP | 58-211646 | 12/1983 |
| JP | 59-34882 | 2/1984 |
| JP | 59-67452 | 4/1984 |
| JP | 59-147249 | 8/1984 |
| JP | 60-173457 | 9/1985 |
| JP | 60-173458 | 9/1985 |
| JP | 60-173459 | 9/1985 |
| JP | 60-211350 | 10/1985 |
| JP | 61-2060 | 1/1986 |
| JP | 62-114747 | 5/1987 |
| JP | 62-139629 | 6/1987 |
| JP | 63-58149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 64-54345 | 3/1989 |
| JP | 1-114746 | 5/1989 |
| JP | 1-114747 | 5/1989 |
| JP | 1-124060 | 5/1989 |
| JP | 1-134244 | 5/1989 |
| JP | 1-134245 | 5/1989 |
| JP | 1-134246 | 5/1989 |
| JP | 1-156658 | 6/1989 |
| JP | 1-291153 | 11/1989 |
| JP | 02-19758 | 1/1990 |
| JP | 2-62958 | 3/1990 |
| JP | 2-120655 | 5/1990 |
| JP | 2-245650 | 10/1990 |
| JP | 2-287145 | 11/1990 |
| JP | 2-310457 | 12/1990 |
| JP | 3-26956 | 2/1991 |
| JP | 3-28752 | 2/1991 |
| JP | 3-165249 | 7/1991 |
| JP | 3-202764 | 9/1991 |
| JP | 03-293556 | 12/1991 |
| JP | 4-194660 | 7/1992 |
| JP | 04-264246 | 9/1992 |
| JP | 5-72171 | 3/1993 |
| JP | 05-149910 | 6/1993 |
| JP | 5-196595 | 8/1993 |
| JP | 06-109688 | 4/1994 |
| JP | 06-130032 | 5/1994 |
| JP | 61-90050 | 7/1994 |
| JP | 62-85855 | 10/1994 |
| JP | 7-27734 | 1/1995 |
| JP | 7-55757 | 3/1995 |
| JP | 7-72585 | 3/1995 |
| JP | 7-270373 | 10/1995 |
| JP | 8-285814 | 11/1996 |
| JP | 8-285815 | 11/1996 |
| JP | 8-320304 | 12/1996 |
| JP | 9-21778 | 1/1997 |
| JP | 9-101280 | 4/1997 |
| JP | 09-159642 | 6/1997 |
| JP | 09-166571 | 6/1997 |
| JP | 9-264870 | 10/1997 |
| JP | 9-285459 | 11/1997 |
| JP | 10-2874 | 1/1998 |
| JP | 10-170471 | 6/1998 |
| SU | 1281988 | 1/1987 |
| WO | WO 85/05119 | 11/1985 |
| WO | WO 86/00513 | 1/1986 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/09139 | 6/1991 |
| WO | WO 91/15993 | 10/1991 |
| WO | WO 92/13271 | 8/1992 |
| WO | WO 94/20602 | 9/1994 |
| WO | WO 94/27140 | 11/1994 |
| WO | WO 95/02817 | 1/1995 |
| WO | WO 95/13534 | 5/1995 |
| WO | WO 95/22597 | 8/1995 |
| WO | WO 95/28634 | 10/1995 |
| WO | WO 96/00614 | 1/1996 |
| WO | WO 96/06947 | 3/1996 |
| WO | WO 96/30431 | 10/1996 |
| WO | WO 96/32635 | 10/1996 |
| WO | WO 97/00441 | 1/1997 |
| WO | WO 97/02847 | 1/1997 |
| WO | WO 97/13870 | 4/1997 |
| WO | WO 97/18464 | 5/1997 |
| WO | WO 97/18465 | 5/1997 |
| WO | WO 97/19344 | 5/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/01208 | 1/1998 |
| WO | WO 98/35225 | 8/1998 |
| WO | WO 98/35225 A1 * | 8/1998 |
| WO | WO 98/43073 | 10/1998 |
| WO | WO 98/58250 | 12/1998 |
| WO | WO 99/08106 | 2/1999 |
| WO | WO 99/30152 | 6/1999 |
| WO | WO 00/78210 | 12/2000 |
| WO | WO 01/64105 | 9/2001 |
| WO | WO 01/72220 | 10/2001 |
| WO | WO 01/73395 | 10/2001 |

OTHER PUBLICATIONS

Bindra, D.S. et al., "Design and in Vitro Studies of a Needle-Type Glucose Sensor for Subcutaneous Monitoring", Anal. Chem., 63(17):1692-1696 (Sep. 1, 1991).

Bobbioni-Harsch, E. et al., "Lifespan of Subcutaneous glucose sensors and their performances during dynamic glycaemia changes in rats," J. Biomed. Eng. 15:457-463 (1993).

Bowyer et al., "Electrochemical Measurements in Submicroliter Volumes", Analytical Chemistry, 64, pp. 459-462 (1992).
Brandt, J. et al., "Covalent attachment of proteins to polysaccharide carriers by means of benzoquinone," Biochim. Biophys. Acta, 386(1) (1 page Abstract only) (1975).
Bratten et al. "Micromachining Sensors for Electrochemical Measurement in Subnanoliter Volumes" Analytical Chemistry, vol. 69, No. 2, (Jan. 15, 1997).
Brownlee, M. et al., "A Glucose-Controlled Insulin-Delivery System: Semisynthetic Insulin Bound to Lectin", Science, 206(4423):1190-1191 (Dec. 7, 1979).
Cass, A.E.G. et al., "Ferrocene-Mediated Enzyme Electrode for Amperometric Determination of Glucose", Anal. Chem., 56(4):667-671 (Apr. 1984).
Cass, A.E.G. et al., "Ferricinum Ion As an Electron Acceptor for Oxido-Reductases," J. Electroanal. Chem., 190:117-127 (1985).
Cassidy et al., "Novel Electrochemical Device for the Detection of Cholesterol or Glucose" Analyst, Apr. 1993 vol. 118 pp. 415-418.
Castner, J. F. et al., "Mass Transport and Reaction Kinetic Parameters Determined Electrochemically for Immobilized Glucose Oxidase," Biochemisty, 23(10):2203-2210 (1984).
Claremont, D.J. et al., "Biosensors for Continuous in Vivo Glucose Monitoring", IEEE Engineering in Medicine and Biology Society 10th Annual International Conference, New Orleans, Louisiana, 3 pp. (Nov. 4-7, 1988).
Clark, L.C., Jr. et al., "Electrode Systems for Continuous Monitoring in Cardiovascular Surgery," Annals New York Academy of Sciences, pp. 29-45 (1962).
Clark, L.C. et al., "Differential Anodic Enzyme Polarography for the Measurement of Glucose", Oxygen Transport to Tissue: Instrumentation, Methods, and Physiology, 127-133 (1973).
Clark, L.C. et al., "Long-term Stability of Electroenzymatic Glucose Sensors Implanted in Mice," Trans. Am. Soc. Artif. Intern. Organs, XXXIV:259-265 (1988).
Clarke, W. L., et al., "Evaluating Clinical Accuracy of Systems for Self-Monitoring of Blood Glucose," Diabetes Care, 10(5):622-628 (Sep.-Oct. 1987).
Creager et al. ("Self-assembled monolayers and enzyme electrodes: progress, problems and prospects", Analytica Chimica Acta 307:277-289 (1995)).
Csoregi, E. et al., "Design, Characterization, and One-Point in Vivo Calibration of a Subcutaneously Implanted Glucose Electrode," Anal. Chem. 66(19):3131-3138 (Oct. 1, 1994).
Csoregi, E. et al., "On-Line Glucose Monitoring by Using Microdialysis Sampling and Amperometric Detection Based on "Wired" Glucose Oxidase in Carbon Paste," Mikrochim. Acta. 121:31-40 (1995).
Csoregi, E. et al., "Design and Optimization of a Selective Subcutaneously Implantable Glucose Electrode Based on "Wired" Glucose Oxidase," Anal. Chem. 67(7):1240-1244 (Apr. 1, 1995).
Darahazi and Tokuda, "Cyclic voltammetry for reversible redox-electrode reactions I thin-layer cells with closely separated working an auxiliary electrodes of the same size", J. Electroanaly. Chem, 264, p. 77-89, (1989).
Davis, G., "Electrochemical Techniques for the Development of Amperometric Biosensors", Biosensors, 1:161-178 (1985).
Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme," J. Phys. Chem., 91(6):1285-1289 (1987).
Degani, Y. et al., "Direct Electrical Communication between Chemically Modified Enzymes and Metal Electrodes. 2. Methods for Bonding Electron-Transfer Relays to Glucose Oxidase and D-Amino-Acid Oxidase," J. Am. Chem. Soc., 110(8):2615-2620 (1988).
Degani, Y. et al., "Electrical Communication between Redox Centers of Glucose Oxidase and Electrodes via Electrostatically and Covalently Bound Redox Polymers," J. Am. Chem. Soc., 111:2357-2358 (1989).
Denisevich, P. et al., "Unidirectional Current Flow and Charge State Trapping at Redox Polymer Interfaces on Bilayer Electrodes: Principles, Experimental Demonstration, and Theory," J. Am. Chem. Soc., 103(16):4727-4737 (1981).

Dicks, J. M., "Ferrocene modified polypyrrole with immobilised glucose oxidase and its application in amperometric glucose microbiosensors," Ann. Biol. clin., 47:607-619 (1989).
Ellis, C. D., "Selectivity and Directed Charge Transfer through an Electroactive Metallopolymer Film," J. Am. Chem. Soc., 103(25):7480-7483 (1981).
Engstrom, R.C., "Electrochemical Pretreatment of Glassy Carbon Electrodes", Anal. Chem., 54(13):2310-2314 (Nov. 1982).
Engstrom, R.C. et al., "Characterization of Electrochemically Pretreated Glassy Carbon Electrodes", Anal. Chem., 56(2):136-141 (Feb. 1984).
Enthone Inc., "Enplate DSR-3241 Cost and Process Control: Application Process," Imaging Technologies Update. Jun. 2001, No. 3.
Feldman, B.J. et al., "Electron Transfer Kinetics at Redox Polymer/Solution Interfaces Using Microelectrodes and Twin Electrode Thin Layer Cells", J. Electroanal. Chem., 194(1):63-81 (Oct. 10, 1985).
Fischer, H. et al., "Intramolecular Electron Transfer Mediated by 4,4'-Bipyridine and Related Bridging Groups", J. Am. Chem. Soc., 98(18):5512-5517 (Sep. 1, 1976).
Foulds, N.C. et al., "Enzyme Entrapment in Electrically Conducting Polymers," J. Chem. Soc., Faraday Trans 1., 82:1259-1264 (1986).
Foulds, N.C. et al., "Immobilization of Glucose Oxidase in Ferrocene-Modified Pyrrole Polymers," Anal. Chem., 609(22):2473-2478 (Nov. 15, 1988).
Frew, J.E. et al., "Electron-Transfer Biosensors", Phil. Trans. R. Soc. Lond., B316:95-106 (1987).
Gamache et al. ("Simultaneous measurement of monamines, metabolites and amino acids in brain tissue and microdialysis perfusates", J. Chromatogr., Biomed. Appl. (1993), 614(2), 213-20), 1993.
Gorton, L. et al., "Selective detection in flow analysis based on the combination of immobilized enzymes and chemically modified electrodes," Analytica Chimica Acta., 250:203-248 (1991).
Gregg, B. A. et al., "Cross-Linked Redox Gels Containing Glucose Oxidase for Amperometric Biosensor Applications," Analytical Chemistry, 62(3):258-263 (Feb. 1, 1990).
Gregg, B. A. et al., "Redox Polymer Films Containing Enzymes. 1. A Redox-Conducting Epoxy Cement: Sythesis, Characterization, and Electrocatalytic Oxidation of Hydroquinone," J. Phys. Chem., 95(15):5970-5975 (1991).
Groom et al. ("Electrical communication between a water-soluble 1,1'-dimethylferrocene-2-hydroxypropyl-b-cyclodextrin complex and glucos oxidase; biosensor applications", Biosensors & Bioelectronics 9:305-313 (1994).
Grubb et al., "Blood oxygen content in microliter samples using an easy-to-build galvanic cell", Journal of Applied Physiology, pp. 456-464 (1981).
Hale, P.D. et al., "A New Class of Amperometric Biosensor Incorporating a Polymeric Electron-Transfer Mediator," J. Am. Chem. Soc., 111(9):3482-3484 (1989).
Harrison, D.J. et al., "Characterization of Perfluorosulfonic Acid Polymer Coated Enzyme Electrodes and a Miniaturized Integrated Potentiostat for Glucose Analysis in Whole Blood", Anal. Chem., 60(19):2002-2007 (Oct. 1, 1988).
Hawkridge, F. M. et al., "Indirect Coulometric Titration of Biological Electron Transport Components," Analytical Chemistry, 45(7):1021-1027 (Jun. 1973).
Heineman, W.R. "Spectro-electro-chemistry", Analytical Chemistry, 50(3):390-392, 394, 396, 398, 400, 402 (Mar. 1978).
Heineman, W.R. et al., "Measurement of Enzyme E.degree. Values by Optically Transparent Thin Layer Electrochemical Cells", Analytical Chemistry, 47(1):79, 82-84 (Jan. 1975).
Heller, A., "Electrical Wiring of Redox Enzymes," Acc. Chem. Res., 23(5):129-134 (1990).
Heller, A., "Electrical Connection of Enzyme Redox Centers to Electrodes," J. Phys. Chem 96(9):3579-3587 (1992).
Heller, A., "Amperometric biosensors based on three-dimensional hydrogel-forming epoxy networks," Sensors and Actuators B, 13-14:180-183 (1993).
Hubbard, A. et al. "The Theory and Practice of Electrochemistry with Thin Layer Cells", Electroanalytical Chemistry A Series of Advances, vol. 4, pp. 129-131, 142-147, 168-171, edited by Allen J. Bard, Marcel Deckker, Inc. New York (1970).

Huang et al., "Detection of basal acetylcholine in rat brain microdialyse", Journal of Chromatography B, 670. 323-327 (1995).

Ianniello, R.M. et al., "Differential Pulse Voltammetric Study of Direct Electron Transfer in Glucose Oxidase Chemically Modified Graphite Electrodes", Anal. Chem., 54:(7):1098-1101 (Jun. 1982).

Ianniello, R.M. et al. "Immobilized Enzyme Chemically Modified Electrode as an Amperometric Sensor", Anal. Chem., 53(13):2090-2095 (Nov. 1981).

Ikeda, T. et al., "Glucose oxidase-immobilized benzoquinone-carbon paste electrode as a glucose sensor," Agric. Biol. Chem., 49(2) (1 page—Abstract only) (1985).

Ikeda, T. et al., "Kinetics of Outer-Sphere Electon Transfers Between Metal Complexes in Solutions and Polymeric Films on Modified Electrodes", J. Am. Chem. Soc., 103(25):7422-7425 (Dec. 16, 1981).

Jobst et al., Mass producible miniaturized flow through a device with a biosensor array, Sensors and Actuators B: 43 (Sep. 1997) 121-125.

Johnson, J. M. et al., "Potential-Dependent Enzymatic Activity in a Enzyme Thin-Layer Cell," Anal. Chem. 54:1377-1383 (1982).

Johnson, K.W., "Reproducible Electrodeposition of Biomolecules for the Fabrication of Miniature Electroenzymatic Biosensors", Sensors and Actuators B Chemical, B5:85-89 (1991).

Jonsson, G. et al., "An Amperometric Glucose Sensor Made by Modification of a Graphite Electrode Surface With Immobilized Glucose Oxidase and Adsorbed Mediator", Biosensors, 1:35-368 (1985).

Josowicz, M. et al., "Electrochemical Pretreatment of Thin Film Platinum Electrodes", J. Elecrochem. Soc., 135(1):112-115 (Jan. 1988).

Karube et al., "Microbiosensors Prepared by Micromachining," GBF Monographs (1992), 17 (Biosens.: Fundam. Technol. appl.) 477-89.

Katakis, I. et al., "L-.alpha.-Glycerophosphate and L-Lactate Electrodes Based on the Electrochemical "Wiring" of Oxidases," Analytical Chemistry, 64(9):1008-1013 (May 1, 1992).

Katakis, I. et al., "Electrostatic Control of the Electron Transfer Enabling Binding of Recombinant Glucose Oxidase and Redox Polyelectrolytes," J. Am. Chem. Soc., 116(8):3617-3618 (1994).

Kenausis, G. et al., "'Wiring' of glucose oxidase and lactate oxidase within a hydrogel made with poly(vinyl pyridine) complexed with [Os(4,4'-dimethoxy-2,2'-bipyridine).sub.2 C1].sup.+/2+," J. Chem. Soc., Faraday Trans., 92(20):4131-4136 (1996).

Kishimoto et al., "Home Care Disposable Glucose Sensor for Blood-Sugar Monitoring," Sumimoto Met., 46(4) (1994).

Kissinger, "Biomedical Applications of Liquid Chromatography-Electrochemistry" Journal of Chromatography, 488 (1989) 31-52, month unknown.

Koudelka, M. et al., "In-Vivo Behaviour of Hypodermically Implanted Microfabricated Glucose Sensors", Biosensors & Bioelectronics, 24:305-311 (1990).

Koudelka, M. et al., "In-Vivo Behaviour of Hypodermically Implanted Microfabricated Glucose Sensors", Biosensors & Bioelectronics, 6(1):31-36 (1991).

Kulys, J. et al., "Mediatorless peroxidase electrode and preparation of bienzyme sensors," Bioelectrochemistry and Bioenergetics, 24:305-311 (1990).

Lager, W. et al., "Implantable Electrocatalytic Glucose Sensor," Horm. Metab. Res., 26:526-530 (Nov. 1994).

Lindner, E. et al. "Flexible (Kapton-Based) Microsensor Arrays of High Stability for Cardiovascular Applications", J. Chem. Soc. Faraday Trans., 89(2):361-367 (Jan. 21, 1993).

Liu et al., "Miniature Multiple Cathode Dissolved Oxygen Sensor for Marine Science Applications", Marine Technology "The Decade of Oceans" pp. 468-472 (1980).

Liu and Neuman, "Fabrication of Miniature PO2 and pH Sensors Using Microelectronic Techniques", Diabetes Care, vol. 5, No. 3, pp. 275-276 (May-Jun. 1982).

Maidan, R. et al., "Elimination of Electrooxidizable Interferant-Produced Currents in Amperometric Biosensros," Analytical Chemistry, 64(23):2889-2896 (Dec. 1, 1992).

Mann-Buxbaum, E. et al, "New Microminiaturized Glucose Sensors Using Covalent Immobilization Techniques", Sensors and Actuators, B1:518-522 (1990).

McKean et al., "A telemetry-Instrumentation System for Chronically Implanted Glucose and Oxygen Sensors", IEEE Transactions of Biomedical Engineering, 35(7):526-532 (Jul. 1988).

McNeil, C. J. et al., "Thermostable Reduced Nicotinamide Adenine Dinucleotide Oxidase: Application to Amperometric Enzyme Assay," Anal. Chem., 61(1):25-29 (Jan. 1, 1989).

Miyasaka, Takehiro, "Development of Enzyme Controlled Glucose Sensor in Blood Activated . . . ," Chemical Engineering, vol. 42, No. 5 (Jun. 19, 1995).

Moatti-Sirat, D. et al., "Evaluating in vitro and in vivo the inteference of ascorbate and acetaminophen on glucose detection by a needle-type glucose sensor," Biosensors & Bioelectronics, 7(5):345-352 (1992).

Moatti-Sirat, D. et al., "Towards continuous glucose monitoring: in vivo evaluation of a miniaturized glucose sensor implanted for several days in rat subcutaneous tissue," Diabetologia, 35(3) (1 page—Abstract only) (Mar. 1992).

Moatti-Sirat, D. et al., "Reduction of acetaminophen interference in glucose sensors by a composite Nafion membrane: demonstration in rats and man," Diabetologia, 37(6) (1 page—Abstract only) (Jun. 1994).

Morris, N.A., "An Electrochemical Capillary Fill Device for the Analysis of Glucose Incorporating Glucose Oxidase and Ruthenium (III) Hexamine as Mediator," Electroanalysis, vol. 4, No. 1 (Jan. 1992).

Moser, I. et al., "Advanced Immobilization and Protein Techniques on thin Film Biosensors", Sensors and Actuators, B7:356-362 (1992).

Moser et al., "Rapid liver enzyme assay with miniaturized liquid handling system comprising thin film biosensor array", Sensors and Actuators B: Chemical 1997;44(1-3):377-80.

Moussy, F. et al., "Performance of Subcutaneously Implanted Needle-Type Glucose Sensors Employing a Novel Trilayer Coating", Anal. Chem., 65:2072-2077 (1993).

Nakamura, S. et al., "Effect of Periodate Oxidation on the Structure and Properties of Glucose Oxidase," Biochimica et Biophysica Acta., 445:294-308 (1976).

Narazimhan, K. et al., "p-Benzoquinone activation of metal oxide electrodes for attachment of enzymes," Enzyme Microb. Technol., 7(6) (1 page—Abstract only) (1985).

Niwa et al. "Small-Volume Voltammetric Detection of 4-aminophenol with Interdigitated Array Electrodes and its Application to Electrochemcial Enzyme Immunoassay," Anal. Chem., (Jun. 1993), 65, 1559-1563.

Niwa, O. et al., "Concentration of Extracellular L-Glutamate Released from Cultured Nerve Cells Measured with a Small-Volume Online Sensor," Analytical Chemistry, 68(11), Jun. 1, 1996, pp. 1865-1870.

Ohara, T. J. et al., ""Wired" Enzyme Electrodes for Amperometric Determination of Glucose or Lactate in the Presence of Interfering Substances," Analytical Chemistry, 66(15):2451-2457 (Aug. 1, 1994).

Ohara, T. J., "Osmium Bipyridyl Redox Polymers Used in Enzyme Electrodes," Platinum Metals Rev., 39(2):54-62 (Apr. 1995).

Olievier, C. N. et al., "In vivo Measurement of Carbon Dioxide Tension with a Miniature Electrode," Pflugers Arch. 373:269-272 (1978).

Paddock, R. et al., "Electrocatalytic reduction of hydrogen peroxide via direct electron transfer from pyrolytic graphite electrodes to irreversibly adsorbed cytochrome c peroxidase," J. Electroanal. Chem., 260:487-494 (1989).

Palleschi, G. et al., "A Study of Interferences in Glucose Measurements in Blood by Hydrogen Peroxide Based Glucose Probes", Anal. Biochem., 159:114-121 (1986).

Palleschi, G. et al., "Ideal Hydrogen Peroxide-Based Glucose Sensor", Applied Biochemistry and Biotechnology, 31:21-35 (1991).

Pankratov, I. et al., "Sol-gel derived renewable-surface biosensors," Journal of Electroanalytical Chemistry, 393:35-41 (1995).

Pickup, J. et al., "Potentially-implantable amperometric glucose sensors with mediated electron transfer: improving the operating stability," Biosensors, 4(2) (1 page—Abstract only) (1989).

Pickup, J. C. et al., "In vivo molecular sensing in diabetes mellitus: an implantable glucose sensor with direct electron transfer," Diabetologia, 32(3):213-217 (1989).

Pickup, J., "Developing glucose sensors for in vivo use," TIBTECH, 11(7): 285-289 (Jul. 1993).

Pishko, M.V. et al., "Amperometric Glucose Microelectrodes Prepared Through Immobilization of Glucose Oxidase in Redox Hydrogels", Anal. Chem., 63(20):2268-2272 (Oct. 15, 1991).

Poitout, V. et al., "In vitro and in vivo evaluation in dogs of a miniaturized glucose sensor," ASAIO Transactions, 37(3) (1 page—Abstract only) (Jul.-Sep. 1991).

Poitout, V. et al., "Calibration in dogs of a Subcutaneous miniaturized glucose sensor using a glucose meter for blood glucose determination," Biosensors & Bioelectronics, 7:587-592 (1992).

Poitout, V. et al., "A glucose monitoring system for on line estimation in man of blood glucose concentration using a miniaturized glucose sensor implanted in the Subcutaneous tissue and a wearable control unit," Diabetolgia, 36(7) (1 page—Abstract only) (Jul. 1993).

Pollak, A. et al., "Enzyme Immobilization by Condensation Copolymerization into Cross-Linked Polyacrylamide Gels," J. Am. Chem. Soc., 102(20):6324-6336 (1980).

Reach, G. et al., "Can Continuous Glucose Monitoring Be Used for the Treatment of Diabetes?" Analytical Chemistry, 64(6):381-386 (Mar. 15, 1992).

Rebrin, K. et al., "Automated Feedback Control of Subcutaneous Glucose Concentration in Diabetic Dogs", Diabetologia, 32(8):573-576 (Aug. 1989).

Roche's Final Invalidity Contentions of '745 and '551 Patents as of Jun. 18, 2007, and references.

Roe, "Comparison of Amperometric and Coulometric Electrochemical Detectors for HPLC through a Figure of Merit", Analytical Letters, 16(A8), 613-631 (1983).

Sakakida, M. et al., "Ferrocene-mediate needle-type glucose sensor covered with newly designed biocompatible membrane," Sensors and Actuators .beta., 13-14:319-322 (1993).

Samuels, G. J. et al., "An Electrode-Supported Oxidation Catalyst Based on Ruthenium (IV). pH "Encapsulation" in a Polymer Film," J. Am. Chem. Soc., 103(2):307-312 (1981).

Sasso, S.V. et al., "Electropolymerized 1,2-Diaminobenzene as a Means to Prevent Interferences and Fouling and to Stabilize Immobilized Enzyme in Electrochemical Biosensors", Anal. Chem., 62(11): 1111-1117 (Jun. 1, 1990).

Scheller, F. et al., "Enzyme electrodes and their application," Phil. Trans. R. Soc. Lond., B 316:85-94 (1987).

Schmehl, R.H. et al., "The Effect of Redox Site Concentration on the Rate of Mediated Oxidation of Solution Substrates by a Redox Copolymer Film", J. Electroanal. Chem., 152:97-109 (Aug. 25, 1983).

Shichiri, M. et al., "Glycemic Control in Pancreatectomized Dogs with a Wearable Artificial Endocrine Pancreas", Diabetologia, 24(3):179-184 (Mar. 1983).

Shigeru, T. et al, "Simultaneous Determination of Glucse and 1,5-= Anydroglucitol", Chemical Abstracts, 111:394 (1989).

Sittampalam, G. et al., "Surface-Modified Electrochemical Detector for Liquid Chromatography", Anal. Chem., 55(9):1608-1610 (Aug. 1983).

Soegijoko, S. et al., Horm. Metabl. Res., Suppl. Ser, 12 (1 page—Abstract only) (1982).

Sprules, S. D. et al., "Evaluation of a New Disposable Screen-Printed Sensor Strip for the Measurement of NADH and Its Modification to Produce a Lactate Biosensor Employing Microliter Volumes," Electroanalysis, 8(6):539-543 (1996).

Sternberg, R. et al., "Study and Development of Multilayer Needle-type Enzyme-based Glucose Microsensors," Biosensors, 4:27-40 (1988).

Sternberg, R. et al., "Covalent Enzyme Coupling on Cellulose Acetate Membranes for Glucose Sensor Development," Analytical Chemistry, 60(24):2781-2786 (Dec. 15, 1988).

Sternberg, F. et al., "Calibration Problems of Subcutaneous Glucosensors when Applied "In-Situ" in Man," Horm. metabl. Res, 26:523-525 (1994).

Suekane, M., "Immobilization of glucose isomerase," Zeitschrift fur Allgemeine Mikrobiologie, 22(8):565-576 (1982).

Tajima, S. et al., "Simultaneous Determination of Glucose and 1.5-Anydrogluc.sub.—tol", Chemical Abstracts, 111(25):394 111:228556g (Dec. 18, 1989).

Takata, Y., "Liquid Chromatography with Coulometric Detector", Advances in Liquid Chromatography: 35 years of Column Liquid, Eds. Hanai et al., World Scientific, pp. 43-74 (1996).

Tarasevich, M.R. "Bioelectrocatalysis", Comprehensive Treatise of Electrochemistry, 10 (Ch. 4):231-295 (1985).

Tatsuma, T. et al., "Enzyme Monolayer- and Bilayer-Modified Tin Oxide Electrodes for the Determination of Hydrogen Peroxide and Glucose," Anal. Chem., 61(2):2352-2355 (Nov. 1, 1989).

Taylor, C. et al., "'Wiring' of glucose oxidase within a hydrogel made with polyvinyl imidazole complexed with [(Os-4,4'-dimethoxy-2,2'-bipyridine)C1].sup.+/2+," Journal of Electroanalytical Chemistry, 396:511-515 (1995).

Therasense, Inc. (now known as Abbott Diabetes Care Inc.) and Abbott Laboratories v. Becton, Dickinson and Company and Nova Biomedical Corporation, and Bayer Healthcare LLC, United States Court of Appeals for the Federal Circuit, Decided: Jan. 25, 2010.

Tietz, in: "Textbook of Clinical Chemistry", C. A. Burtis and E.R. Ashwood, eds., W. B. Saunders Co., Phila 1994, pp. 2210-2212.

Trojanowicz, M. et al., "Enzyme Entrapped Polypyrrole Modified Electrode for Flow-Injection Determination of Glucose," Biosensors & Bioelectronics, 5:149-156 (1990).

Turner, A.P.F. et al., "Diabetes Mellitus: Biosensors for Research and Management", Biosensors, 1:85-115 (1985).

Turner, R. F. B. et al., "A Biocompatible Enzyme Electrode for Continuous in vivo Glucose Monitoring in Whole Blood," Sensors and Actuators, B1(1-6):561-564 (Jan. 1990).

Tuzhi, P. et al., "Constant Potential Pretreatment of Carbon Fiber Electrodes for in Vivo Electrochemistry", Analytical Letters, 24(6):935-945 (1991).

Uhegbu et al., "Initial Studies of a New Approach to the Design and Use of Enzyme-Based Reactor/Sensor Systems: Amperometric System for Glucose" Anal. Chem. 1993, 65, 2443-2451, month unknown.

Umaha, M., "Protein-Modified Electrochemically Active Biomaterial Surface," U.S. Army Research Office Report, (12 pages) (Dec. 1988).

Urban, G. et al., "Miniaturized Thin-Film Biosensors Using Covalently Immobilized Glucose Oxidase", Biosensors & Bioelectronics, 6(7):555-562 (1991).

Van Der Schoot et al., "An ISFET-Based Microlite Titrator: Integration of a Chemical Sensor-Actuator System*", Sensors and Actuators, 8:11-22 (1985).

Velho, G. et al., "In Vitro and in Vivo Stability of Electrode Potentials in Needle-Type Glucose Sensors", Diabetes, 38(2):164-171 (Feb. 1989).

Velho, G. et al., "Strategies for calibrating a Subcutaneous glucose sensor," Biomed. Biochin. Acta, 48(11/12):957-964 (1989).

Von Woedtke, T. et al., "In Situ Calibration of Implanted Electrochemical Glucose Sensors," Biomed. Biochim. Acta, 48(11/12):943-952 (1989).

Vreeke, M. et al., "Hydrogen Peroxide and .beta.-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network," Analytical Chemistry, 64(24):3084-3090 (Dec. 15, 1992).

Vreeke, M. S. et al., "Chapter 15: Hydrogen Peroxide Electrodes Based on Electrical Connection of Redox Centers of Various Peroxidases to Electrodes through a Three-Dimensional Electron Relaying Polymer Network," Diagnostic Biosensor Polymers, 7 pp. (Jul. 26, 1993).

Vriend, J., "Determination of Amino Acids and Monoamine Neurotransmitters in Caudate Nucleus of Seizure-Resistant and Seizure-Prone BALB/c Mice," Journal of Neurochemistry, vol. 60, No. 4, pp. 1300-1307 (1993).

Wang, J. et al., "Activation of Glassy Carbon Electrodes by Alternating Current Electrochemical Treatment", Analytica Chimica Acta, 167:325-334 (Jan. 1985).

Wang, J. et al., "Amperometric biosensing of organic peroxides with peroxidase-modified electrodes," Analytica Chimica Acta. 254:81-88 (1991).

Wang, D. L. et al., "Miniaturized Flexible Amperometric Lactate Probe," Analytical Chemistry, 65(8):1069-1073 (Apr. 15, 1993).

Wang, J. et al., "Screen-Printable Sol-Gel Enzyme-Containing Carbon Inks," Analytical Chemistry, 68(15):2705-2708 (Aug. 1, 1996).

Wang, J. et al., "Sol-Gel-Derived Metal-Dispersed Carbon Composite Amperometric Biosensors," Electroanalysis, 9(1):52-55 (1997).

Williams, D.L. et al., "Electrochemical-Enzymatic Analysis of Blood Glucose and Lactate", Anal. Chem., 42(1):118-121 (Jan. 1970).

Wilson, G. S. et al., "Progress toward the Development of an Implantable Sensor for Glucose," Clinical Chemistry, 38(9):1613-1617 (1992).

Yabuki, S. et al., "Electro-conductive Enzyme Membrane," J. Chem. Soc. Chem. Commun, 945-946 (1989).

Yang et al., "Application of "Wired" Peroxidase Electrodes for Peroxide Determination in Liquid Chromatography Coupled to Oxidase Immobilized Enzyme Reactors" Anal. Chem. 1995, 67, 1326-1331 Apr.

Yang et al., "Continuous Monitoring of Subcutaneous Glucose and Lactate Using Microdialysis With On-Line Enzyme Electrodes" Current Separations 14:1(1995) pp. 31-35, month unknown.

Yang, L. et al., "Determination of Oxidase Enzyme Substrates Using Cross-Flow Thin-Layer Amperometry," Electroanalysis, 8(8-9):716-721 (1996).

Yao, S.J. et al., "The Interference of Ascorbate and Urea in Low-Potential Electrochemical Glucose Sensing", Proceedings of the Twelfth Annual International Conference of the IEEE Engineering in Medicine and Biology Society, 12(2):487-489 (Nov. 1-4, 1990).

Ye, L. et al., "High Current Density "Wired" Quinoprotein Glucose Dehydrogenase Electrode," Anal. Chem., 65(3):238-241 (Feb. 1, 1993).

Yildiz, A., "Evaluation of an Improved Thin-Layer Electrode", Analytical Chemistry, 40(7):1018-1024 (Jun. 1968).

Zamzow, K. et al., New Wearable Continuous Blood Glucose Monitor (BGM) and Artificial Pancreas (AP), Diabetes, 39:5A(20) (May 1990).

Zhang, Y. et al. "Application of cell culture toxicity tests to the development of implantable biosensors," Biosensors & Bioelectronics, 6:653-661(1991).

Abruna, H. D. et al., "Rectifying Interfaces Using Two-Layer Films of Electrochemically Polymerized Vinylpyridine and Vinylbipyridine Complexes of Ruthenium and Iron on Electrodes," J. Am. Chem. Soc., 103(1):1-5 (Jan. 14, 1981).

Albery, W. J. et al., "Amperometric enzyme electrodes. Part II. Conducting salts as electrode materials for the oxidation of glucose oxidase," J. Electroanal. Chem. Interfacial Electrochem., 194(2) pp. 223-235 (1985).

Albery, W. J. et al., "Amperometric Enzyme Electrodes," Phil. Trans. R. Soc. Lond. B316:107-119 (1987).

Alcock, S. J. et al., "Continuous Analyte Monitoring to Aid Clinical Practice," IEEE Engineering in Medicine and Biology, 319-325 (1994).

Anderson, L. B. et al., "Thin-Layer Electrochemistry: Steady-State Methods of Studying Rate Processes," J. Electroanal. Chem., 10:295-305 (1965).

Anderson, C. W. et al., "A Small-Volume Thin-Layer Spectroelectrochemical Cell for the Study of Biological Components", Analytical Biochemistry, 93(2):366-372 (1979).

Bard and Faulkner, "Electrochemical Methods: Fundamentals and Applications", pp. 2-3, 23-24 (1980).

Bartlett, P. N. et al., "Covalent Binding of Electron Relays to Glucose Oxidation," J. Chem. Soc. Chem. Commun., 1603-1604 (1987).

Bartlett, P. N. et al., "Strategies for the Development of Amperometric Enzyme Electrodes," Biosensors, 3:359-379 (1987/1988).

Bartlett, P. N. et al., "Modification of glucose oxidase by tetrathiafulvalene," J. Chem. Soc., Chem. Commun., 16:1135-1136 (1990).

Bayer Corporation, Glucometer DEX blood glucose monitoring system, User guide. Bayer Corporation, (Rev. Jul. 1997).

Bayer Corporation, Glucometer elite diabetes care system, User guide for use with Glucometer Elite blood glucose meter. Bayer Corporation, (Rev. Jun. 1998).

Bayer's Invalidity Contentions of '745 and '551 Patents as of Jun. 18, 2007, and references.

Caglar and Wnek, "Glucose-Sensitive Polyphyrrole/poly (Styrenesulfonate) Films Containing Co-Immobilized Glucose Oxidase and (Ferrocenylmethyl) Trimethylammonium Bromide," J. of Macromolecular Sc.—Pure Appl. Chem., A32(2), pp. 349-359 (1995).

Chen, C.Y. et al., "Amperometric Needle-Type Glucose Sensor based on a Modified Platinum Electrode with Diminished Response to Interfering Materials", Analytica Chimica Acta, 265:5-14 (1992).

Chen, C.Y. et al., "A Biocompatible Needle-Type Glucose Sensor Based on Platinum-Electroplated Carbon Electrode", Applied Biochemistry and Biotechnology, 36:211-226 (1992).

Gernet, S. et al., "Fabrication and Characterization of a Planar Electrochemical Cell and Its Application as a Glucose Sensor", Biosensors & Actuators, 18:59-70 (1989).

Hubbard, A. et al., "Electrochemistry in Thin Layers of Solution", CRC Critical Reviews in Analytical Chemistry, 3(2):201-242 (Mar. 1973).

Johnson K. W. et al., "In Vivo Evaluation of an Electroenzymatic Glucose Sensor Implanted in Subcutaneous Tissue", Biosensors & bioelectronics 7:709-714 (1992).

Kondo, T. et al., "A Miniature Glucose Sensor, Implantable in the Blood Stream", Diabetes Care, 5(3):218-221 (May-Jun. 1982).

Kuhn L. S., "Biosensors: blockbuster or bomb? Electrochemical biosensors for diabetes monitoring," The Electrochemical Society Interface, 26-31 (1998).

Lee, J. et al., "A New Glucose Sensor using Microporous Enzyme Membrane", Sensors and Actuators, B3:215-219 (1991).

Lewandowski, J.J. et al., "Evaluation of a Miniature Blood Glucose Sensor", Trans Am Soc Artif Intern Organs, XXXIV: 255-258 (1988).

Mastrototaro, J.J. et al., "An Electroenzymatic Glucose Sensor Fabricated on a Flexible Substrate", Sensors and Biosensors B Chemical, B5:139-144 (1991).

Matthews, D.R., et al., "An Amperometric Needle-Type Glucose Sensor Tested in Rats and Man", Original Articles, pp. 248-252 (1988).

McDuffie et al., "Twin Electrode Thin Layer Electrochemistry: Determination of Chemical Reaction Rates by Decay of Steady-State Current", Analytical Chemistry, vol. 38, No. 7, pp. 883-890 (Jun. 1966).

Miyawaki, O. et al., "Electrochemical and Glucose Oxidase Coenzyme Activity of Flavin Adenine Dinucleotide Covalently Attached to Glassy Carbon at the Adenine Amino Group", Biochimica et Biophysica Acta, 838:60-68 (1985).

Nagy, G. et al., "A New Type of Enzyme Electrode: The Ascorbic Acid Eliminator Electrode," Life Sciences, 31(23):2611-2616 (1982).

Niwa, O. et al., "Highly Sensitive Small Volume Voltammetry of Reversible Redox Species with and IDA Electrochemical Cell and its Application to Selective Detection of Catecholamine", Sensors and Actuators B, 13-14, pp. 558-560 (1993).

Ohara, T. J. et al., "Glucose Electrodes Based on Cross-Linked [Os(bpy)$_2$ Cl]$^{+/2+}$Complexed Poly(1-vinylimadazole) Films," Analytical Chemistry, 65(23):3512-3516 (Dec. 1, 1993).

Pathak, C. P. et al., "Rapid Photopolymerization of Immunoprotective Gels in Contact with Cells and Tissue," J. Am. Chem. Soc., 114(21):8311-8312 (1992).

Pons, B. S. et al., "Application of Deposited Thin Metal Films as Optically Transparent Electrodes for Internal Reflection Spectrometric Observation of Electrode Solution Interfaces", Analytical Chemistry, 39(6):685-688, (May 1967).

Reach, G. et al., "A Method for Evaluating in vivo the Functional Characteristics of Glucose Sensors", Biosensors 2:211-220 (1986).

Reilley, "Electrochemistry Using Thin-Layer Cells", Rev. Pure and Appl. Chem., 18, pp. 137-151 (1968).

Schalkhammer, T. et al., "Electrochemical Glucose Sensors on Permselective Non-conducting Substituted Pyrrole Polymers", Sensors and Actuators, B4:273-281 (1991).

Turner, "Research: A new approach to blood glucose tests", Balance, (Aug. 1983).

Turner, A.P.F., "Redox Mediators and their Application in Amperometric Sensors," Proc. NATO Advanced Research Workshop on Analytical Uses of Immobilized Biological Compounds for Detection, Medical and Industrial Uses, Florence, Italy, (May 4-8, 1987), Ed. Guilbault et al., D. Reidel Publishing Company, pp. 131-140.

Vidal, J.C. et al., "A chronoamperometric sensor for hydrogen peroxide based on electron transfer between immobilized horseradish peroxidase on a glassy carbon electrode and a diffusing ferrocene mediator", Sensors and Actuators B 21, pp. 135-141 (1994).

Wingard, "Immobilized enzyme electrode for glucose determination for the artificial pancreas", Federation Proceedings from symposiums for Drugs and Enzymes Attached to Solid Supports, pp. 288-291 (1983).

Woodard and Reilley, Comprehensive Treatise of Electrochemistry, Chapter 6 "Thin Layer Cell Techniques", pp. 353-392 (1984).

Yamasaki, Y., "The Development of a Needle-Type Glucose Sensor for Wearable Artificial Endocrine Pancreas", Medical Journal of Osaka University, vol. 35, No. 1-2, pp. 24-34 (Sep. 1994).

Yao, T. et al., "A Chemically-Modified Enzyme Membrane Electrode As an Amperometric Glucose Sensor," Analytica Chimica Acta., 148:27-33 (1983).

Zhang, Y. et al., "Elimination of the Acetaminophen Interference in an Implantable Glucose Sensor," Anal. Chem. 66:1183-1188 (1994).

Batchelor et al., "Amperometric Assay for the Ketone body 3-Hydroxybutyrate," Analytica Chimica Acta, 221:289-294 (1989).

Choleau et al., "Calibration of a subcutaneous amperometric glucose sensor Part 1. Effect of measurement uncertainties on the determination of sensor sensitivity and background current," Biosensors and Bioelectronics, 17:641-646 (2002).

Kerner et al., "The function of a hydrogen peroxide-detecting electroenzymatic glucose electrode is markedly impaired in human Sub-cutaneous tissue and plasma," Biosensors & Bioelectronics, 8:473-482 (1993).

Linke et al., "Prevention of the Decrease in Sensitivity of an Amperometric Glucose Sensor in Undiluted Human Serum," Clinical Chemistry, 45( 2):283-285 (1999).

Pickup et al., "Responses and calibration of amperometric glucose sensors implanted in the Subcutaneous tissue of man," Acta. Diabetol., 30:143-148 (1993).

Pravda, M. et al., "Evaluation of amperometric glucose biosensors based on co-immobilisation of glucose oxidase with an osmium redox polymer in electrochemically generated polyphenol films," Analytica Chimica Acta, 304:127-138 (1995).

Thomé-Duret et al., "Modification of the Sensitivity of Glucose Sensor Implanted into Subcutaneous Tissue," Diabetes & Metabolism (Paris), 22:174-1 78 (1996).

Ward et al., "A new amperometric glucose microsensor: in vitro and short-term in vivo evaluation," Biosensors & Bioelectronics, 17:181-189 (2002).

Unwin et al., "A Generally Applicable Method for the Measurement of Heterogeneous Rate Constants of Reactions Occurring at the Solid/Liquid Interface," Journal of Colloid and Interface Science, 128(1):208-222 (Mar. 1989).

Diffusion coefficient of glucose in water—*Homo sapiens* from the Catalog of useful Biological Numbers at harvard.edu downloaded from http://bionumbers.hms.harvard.edu/ on Nov. 30, 2011.

* cited by examiner

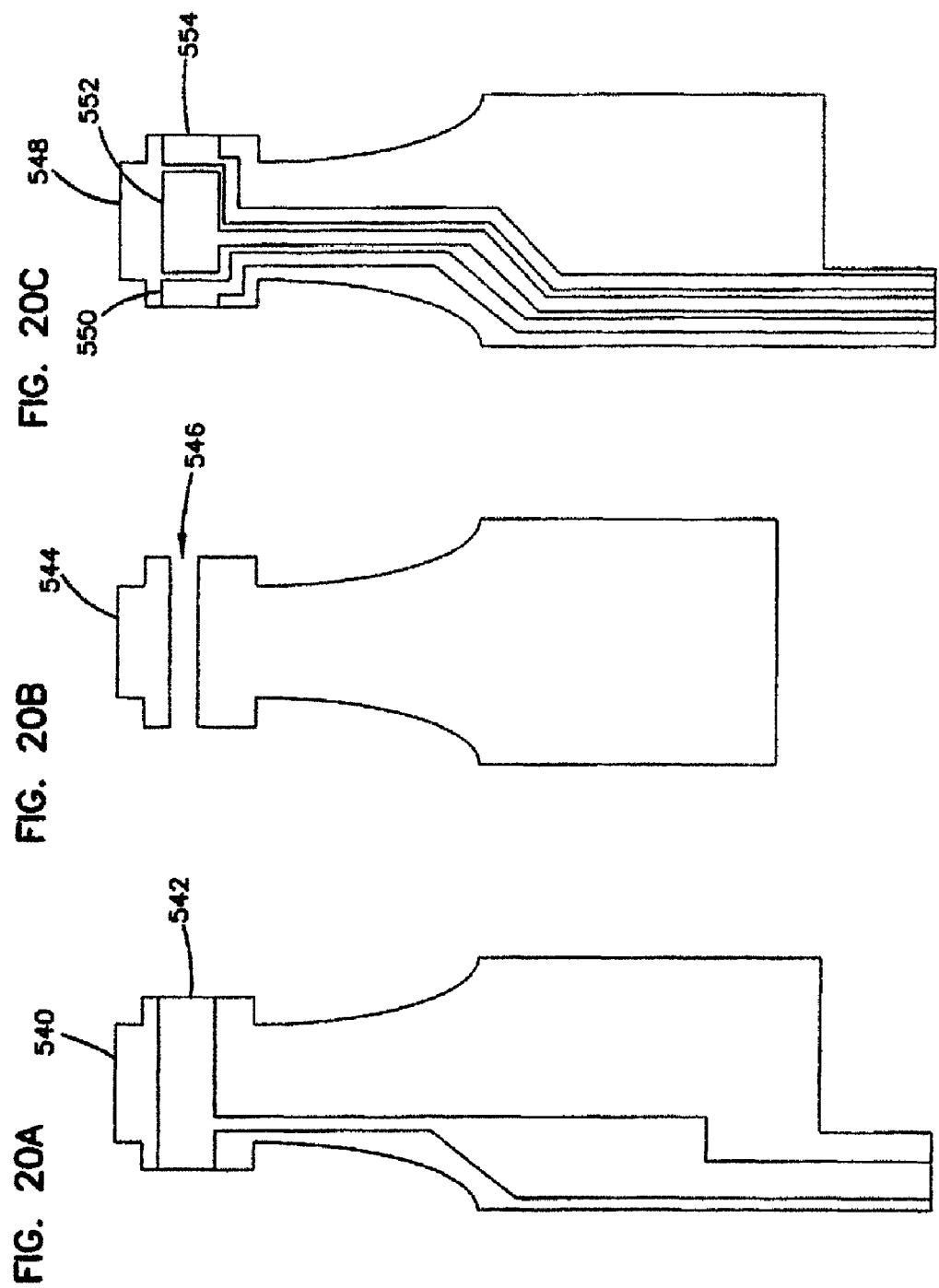

FIG. 21A  FIG. 21B  FIG. 21C
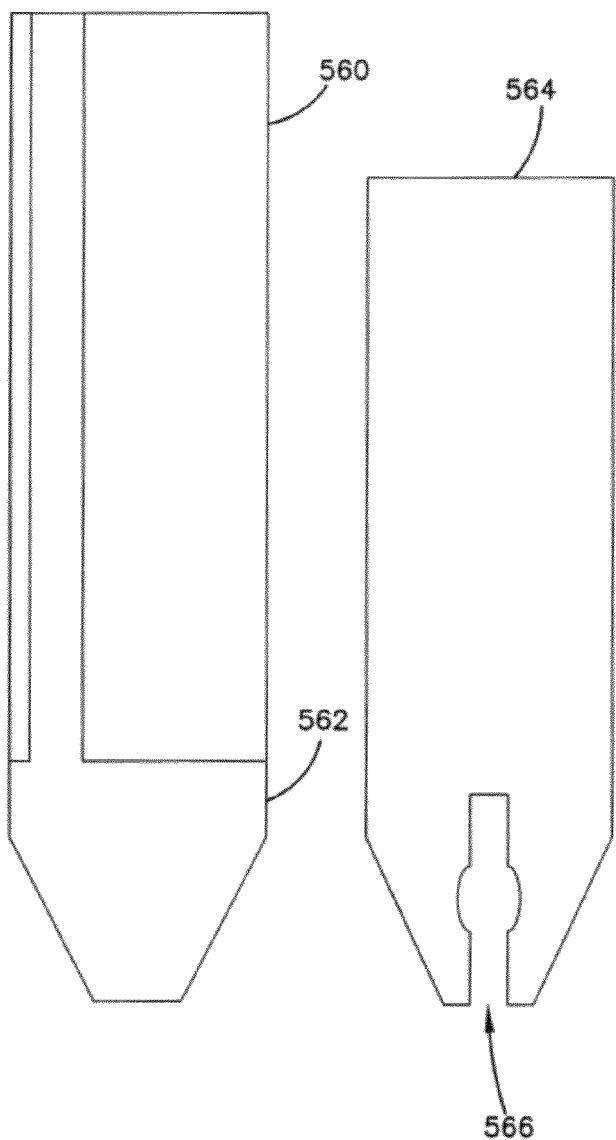
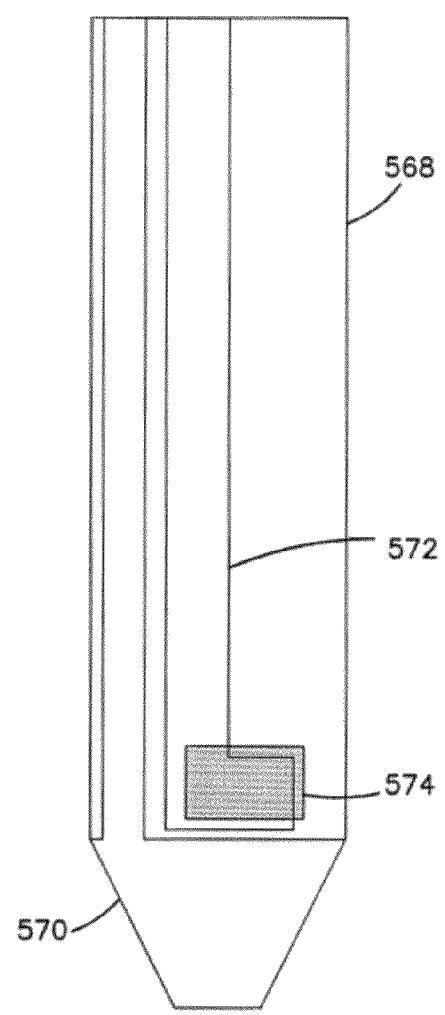

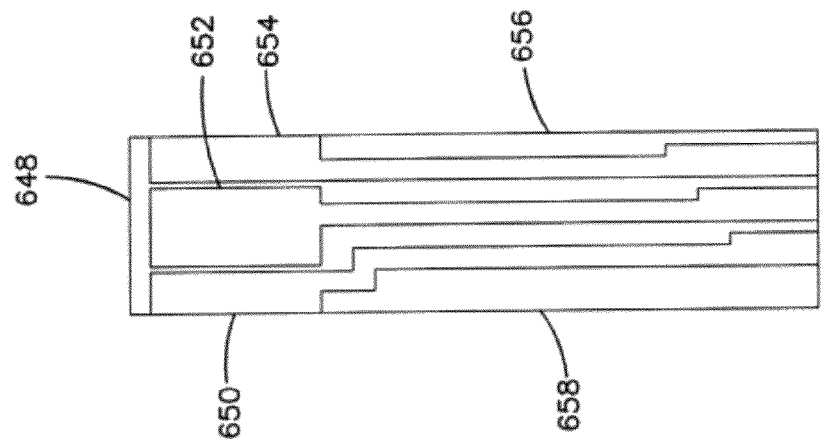
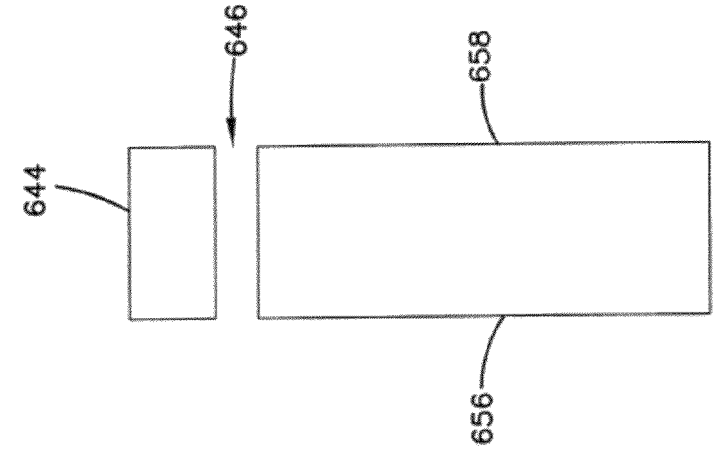
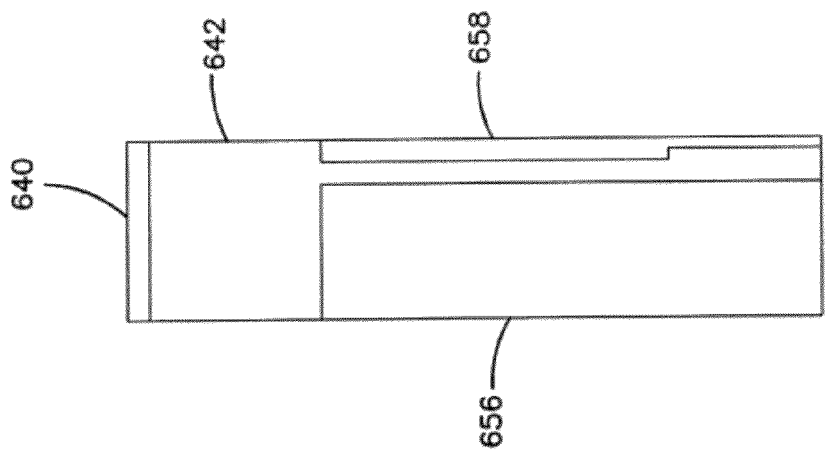

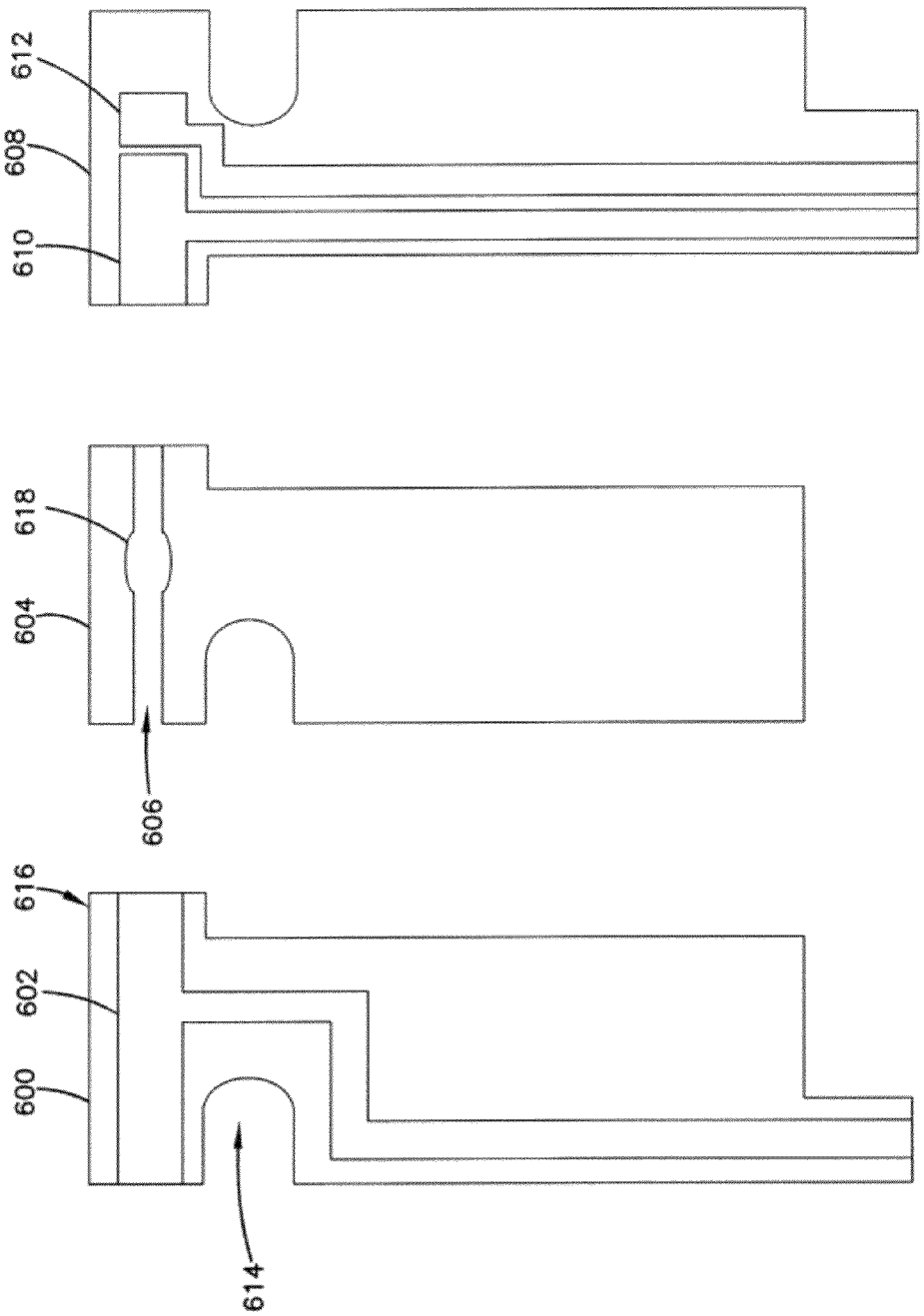

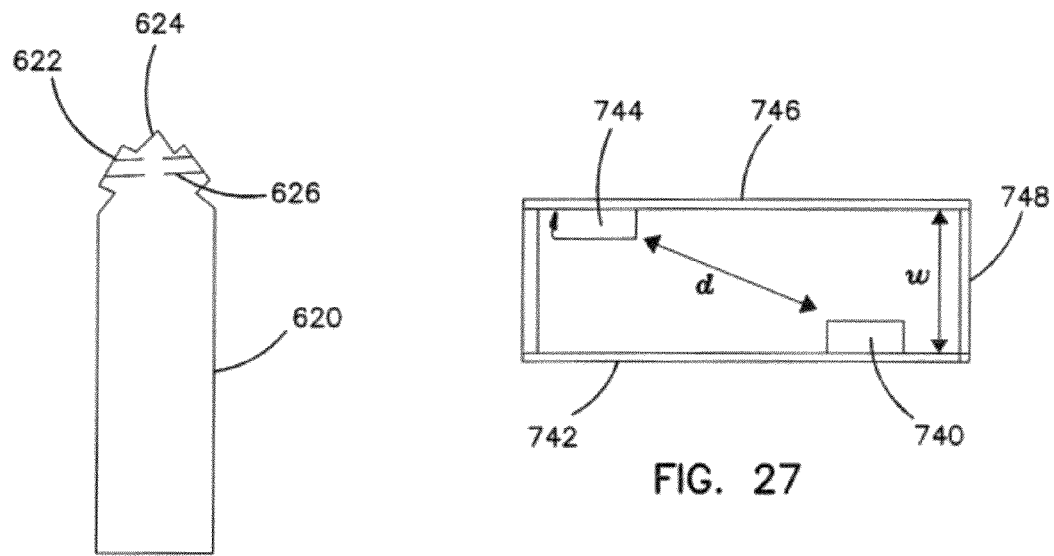
FIG. 25
FIG. 27
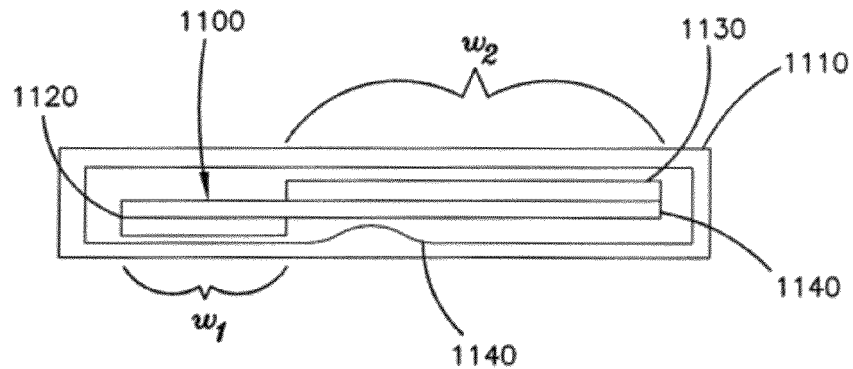
FIG. 32

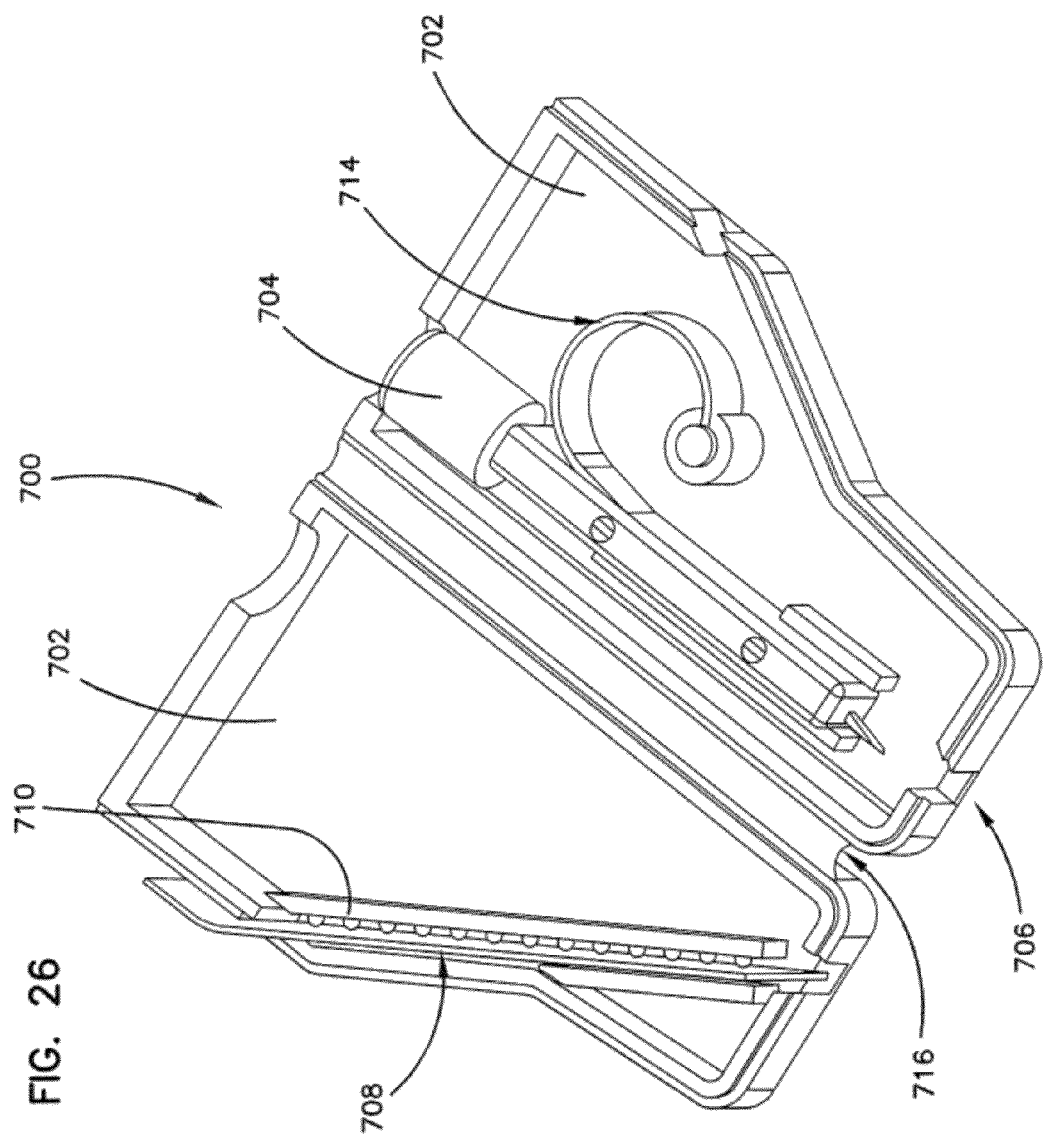

SMALL VOLUME IN VITRO ANALYTE SENSOR AND METHODS OF MAKING

This application is a continuation of Ser. No. 11/734,979, filed on Apr. 13, 2007, which is a divisional of U.S. application Ser. No. 10/662,081, filed Sep. 12, 2003, now issued as U.S. Pat. No. 7,225,535, which is a divisional application of U.S. application Ser. No. 09/594,285, filed Jun. 15, 2000, now issued as U.S. Pat. No. 6,618,934, which is a continuation of U.S. application Ser. No. 09/295,962, filed Apr. 21, 1999, now issued as U.S. Pat. No. 6,338,790, which claims the benefit of U.S. Provisional Application Ser. No. 60/103,627, filed Oct. 8, 1998 and U.S. Provisional Application Ser. No. 60/105,773, filed Oct. 8, 1998.

FIELD OF THE INVENTION

This invention relates to analytical sensors for the detection of bioanalytes in a small volume sample.

BACKGROUND OF THE INVENTION

Analytical sensors are useful in chemistry and medicine to determine the presence and concentration of a biological analyte. Such sensors are needed, for example, to monitor glucose in diabetic patients and lactate during critical care events.

Currently available technology measures bioanalytes in relatively large sample volumes, e.g., generally requiring 3 microliters or more of blood or other biological fluid. These fluid samples are obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have a lower nerve ending density. However, lancing the body in the preferred regions typically produces submicroliter samples of blood, because these regions are not heavily supplied with near-surface capillary vessels.

It would therefore be desirable and very useful to develop a relatively painless, easy to use blood analyte sensor, capable of performing an accurate and sensitive analysis of the concentration of analytes in a small volume of sample.

Sensors capable of electrochemically measuring an analyte in a sample are known in the art. Some sensors known in the art use at least two electrodes and may contain a redox mediator to aid in the electrochemical reaction. However, the use of an electrochemical sensor for measuring analyte in a small volume introduces error into the measurements. One type of inaccuracy arises from the use of a diffusible redox mediator. Because the electrodes are so close together in a small volume sensor, diffusible redox mediator may shuttle between the working and counter electrode and add to the signal measured for analyte. Another source of inaccuracy in a small volume sensor is the difficulty in determining the volume of the small sample or in determining whether the sample chamber is filled. It would therefore be desirable to develop a small volume electrochemical sensor capable of decreasing the errors that arise from the size of the sensor and the sample.

SUMMARY OF THE INVENTION

The sensors of the present invention provide a method for the detection and quantification of an analyte in submicroliter samples. In general, the invention includes a method and sensor for analysis of an analyte in a small volume of sample by, for example, coulometry, amperometry and/or potentiometry. A sensor of the invention utilizes a non-leachable or diffusible redox mediator. The sensor also includes a sample chamber to hold the sample in electrolytic contact with the working electrode. In many instances, the sensor also contains a non-leachable or diffusible second electron transfer agent.

In a preferred embodiment, the working electrode faces a counter electrode, forming a measurement zone within the sample chamber, between the two electrodes, that is sized to contain no more than about 1 µL of sample, preferably no more than about 0.5 µL, more preferably no more than about 0.25 µL, and most preferably no more than about 0.1 µL of sample. A sorbent material is optionally positioned in the sample chamber and measurement zone to reduce the volume of sample needed to fill the sample chamber and measurement zone.

In one embodiment of the invention, a biosensor is provided which combines coulometric electrochemical sensing with a non-leachable or diffusible redox mediator to accurately and efficiently measure a bioanalyte in a submicroliter volume of sample. The preferred sensor includes an electrode, a non-leachable or diffusible redox mediator on the electrode, a sample chamber for holding the sample in electrical contact with the electrode and, preferably, sorbent material disposed within the sample chamber to reduce the volume of the chamber. The sample chamber, together with any sorbent material, is sized to provide for analysis of a sample volume that is typically no more than about 1 µL, preferably no more than about 0.5 more preferably no more than about 0.25 µL, and most preferably no more than about 0.1 µL. In some instances, the sensor also contains a non-leachable or diffusible second electron transfer agent.

One embodiment of the invention includes a method for determining the concentration of an analyte in a sample by, first, contacting the sample with an electrochemical sensor and then determining the concentration of the analyte. The electrochemical sensor includes a facing electrode pair with a working electrode and a counter electrode and a sample chamber, including a measurement zone, positioned between the two electrodes. The measurement zone is sized to contain no more than about 1 µL of sample.

The invention also includes an electrochemical sensor with two or more facing electrode pairs. Each electrode pair has a working electrode, a counter electrode, and a measurement zone between the two electrodes, the measurement zone being sized to hold no more than about 1 µL of sample. In addition, the sensor also includes a non-leachable redox mediator on the working electrode of at least one of the electrode pairs or a diffusible redox mediator on a surface in the sample chamber or in the sample.

One aspect of the invention is a method of determining the concentration of an analyte in a sample by contacting the sample with an electrochemical sensor and determining the concentration of the analyte by coulometry. The electrochemical sensor includes an electrode pair with a working electrode and a counter electrode. The sensor also includes a sample chamber for holding a sample in electrolytic contact with the working electrode. Within the sample chamber is sorbent material to reduce the volume sample needed to fill the sample chamber so that the sample chamber is sized to contain no more than about 1 µL of sample. The sample chamber also contains a non-leachable or diffusible redox mediator and optionally contains a non-leachable or diffusible second electron transfer agent.

The sensors may also include a fill indicator, such as an indicator electrode or a second electrode pair, that can be used to determine when the measurement zone or sample chamber has been filled. An indicator electrode or a second electrode pair may also be used to increase accuracy of the measurement of analyte concentration. The sensors may also include a heating element to heat the measurement zone or sample chamber to increase the rate of oxidation or reduction of the analyte.

Sensors can be configured for side-filling or tip-filling. In addition, in some embodiments, the sensor may be part of an integrated sample acquisition and analyte measurement device. The integrated sample acquisition and analyte measurement device may include the sensor and a skin piercing member, so that the device can be used to pierce the skin of a user to cause flow of a fluid sample, such as blood, that can then be collected by the sensor. In at least some embodiments, the fluid sample can be collected without moving the integrated sample acquisition and analyte measurement device.

One method of forming a sensor, as described above, includes forming at least one working electrode on a first substrate and forming at least one counter or counter/reference electrode on a second substrate. A spacer layer is disposed on either the first or second substrates. The spacer layer defines a channel into which a sample can be drawn and held when the sensor is completed. A redox mediator and/or second electron transfer agent are disposed on the first or second substrate in a region that will be exposed within the channel when the sensor is completed. The first and second substrates are then brought together and spaced apart by the spacer layer with the channel providing access to the at least one working electrode and the at least one counter or counter/reference electrode. In some embodiments, the first and second substrates are portions of a single sheet or continuous web of material.

These and various other features which characterize the invention are pointed out with particularity in the attached claims. For a better understanding of the invention, its advantages, and objectives obtained by its use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 20A illustrates a top view of a first film with a working electrode for use in a seventh embodiment of a sensor according to the invention;

FIG. 20B illustrates a top view of a spacer for placement on the first film of FIG. 20A;

FIG. 20C illustrates a bottom view of a second film (inverted with respect to FIGS. 20A and 20B) with counter electrodes placement over the spacer of FIG. 20B and first film of FIG. 20A;

FIG. 21A illustrates a top view of a first film with a working electrode for use in a eighth embodiment of a sensor according to the invention;

FIG. 21B illustrates a top view of a spacer for placement on the first film of FIG. 21A;

FIG. 21C illustrates a bottom view of a second film (inverted with respect to FIGS. 21A and 21B) with counter electrodes placement over the spacer of FIG. 21B and first film of FIG. 21A;

FIG. 23A illustrates a top view of a first film with a working electrode for use in a tenth embodiment of a sensor according to the invention;

FIG. 23B illustrates a top view of a spacer for placement on the first film of FIG. 23A;

FIG. 23C illustrates a bottom view of a second film (inverted with respect to FIGS. 23A and 23B) with counter electrodes placement over the spacer of FIG. 23B and first film of FIG. 23A;

FIG. 24A illustrates a top view of a first film with a working electrode for use in an eleventh embodiment of a sensor according to the invention;

FIG. 24B illustrates a top view of a spacer for placement on the first film of FIG. 24A;

FIG. 24C illustrates a bottom view of a second film (inverted with respect to FIGS. 24A and 24B) with counter electrodes placement over the spacer of FIG. 24B and first film of FIG. 24A;

FIG. 25 illustrates a top view of a twelfth embodiment of an electrochemical sensor, according to the invention;

FIG. 26 illustrates a perspective view of one embodiment of an integrated analyte acquisition and sensor device;

FIG. 27 illustrates a cross-sectional view of a thirteenth embodiment of a sensor, according to the invention;

FIG. 32 illustrates a cross-sectional view looking from inside the meter to a sensor of the invention disposed in a meter.

DETAILED DESCRIPTION OF THE PREFERRED EMBODIMENT

Figure 1:
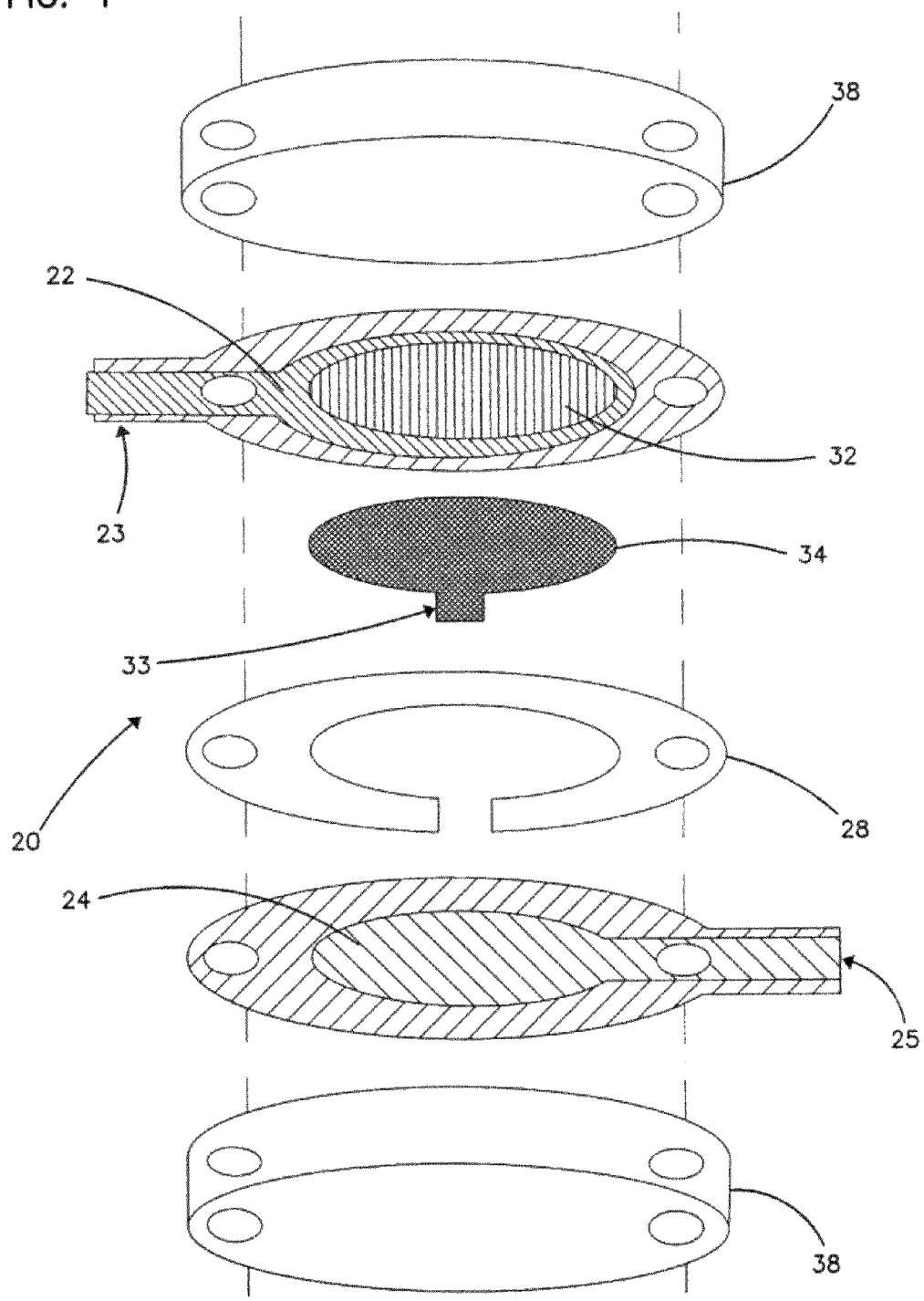
FIG. 1 is a schematic view of a first embodiment of an electrochemical sensor in accordance with the principles of the present invention having a working electrode and a counter electrode facing each other.

When used herein, the following definitions define the stated term:

An "air-oxidizable mediator" is a redox mediator that is oxidized by air, preferably so that at least 90% of the mediator is in an oxidized state upon storage in air either as a solid or as a liquid during a period of time, for example, one month or less, and, preferably, one week or less, and, more preferably, one day or less.

"Amperometry" includes steady-state amperometry, chronoamperometry, and Cottrell-type measurements.

A "biological fluid" is any body fluid in which the analyte can be measured, for example, blood, interstitial fluid, dermal fluid, sweat, and tears.

The term "blood" in the context of the invention includes whole blood and its cell-free components, such as, plasma and serum.

"Coulometry" is the determination of charge passed or projected to pass during complete or nearly complete electrolysis of the analyte, either directly on the electrode or through one or more electron transfer agents. The charge is determined by measurement of charge passed during partial or nearly complete electrolysis of the analyte or, more often, by multiple measurements during the electrolysis of a decaying current and elapsed time. The decaying current results from the decline in the concentration of the electrolyzed species caused by the electrolysis.

A "counter electrode" refers to one or more electrodes paired with the working electrode, through which passes an electrochemical current equal in magnitude and opposite in sign to the current passed through the working electrode. The term "counter electrode" is meant to include counter electrodes which also function as reference electrodes (i.e. a counter/reference electrode) unless the description provides that a "counter electrode" excludes a reference or counter/reference electrode.

An "effective diffusion coefficient" is the diffusion coefficient characterizing transport of a substance, for example, an analyte, an enzyme, or a redox mediator, in the volume between the electrodes of the electrochemical cell. In at least some instances, the cell volume may be occupied by more than one medium (e.g., the sample fluid and a polymer film). Diffusion of a substance through each medium may occur at a different rate. The effective diffusion coefficient corresponds to a diffusion rate through this multiple-media volume and is typically different than the diffusion coefficient for the substance in a cell filled solely with sample fluid.

An "electrochemical sensor" is a device configured to detect the presence of and/or measure the concentration of an analyte via electrochemical oxidation and reduction reactions. These reactions are transduced to an electrical signal that can be correlated to an amount or concentration of analyte.

"Electrolysis" is the electrooxidation or electroreduction of a compound either directly at an electrode or via one or more electron transfer agents (e.g., redox mediators and/or enzymes).

The term "facing electrodes" refers to a configuration of the working and counter electrodes in which the working surface of the working electrode is disposed in approximate opposition to a surface of the counter electrode. In at least some instances, the distance between the working and counter electrodes is less than the width of the working surface of the working electrode.

A compound is "immobilized" on a surface when it is entrapped on or chemically bound to the surface.

An "indicator electrode" includes one or more electrodes that detect partial or complete filling of a sample chamber and/or measurement zone.

A "layer" includes one or more layers.

The "measurement zone" is defined herein as a region of the sample chamber sized to contain only that portion of the sample that is to be interrogated during an analyte assay.

A "non-diffusible," "non-leachable," or "non-releasable" compound is a compound which does not substantially diffuse away from the working surface of the working electrode for the duration of the analyte assay.

The "potential of the counter/reference electrode" is the half cell potential of the reference electrode or counter/reference electrode of the cell when the solution in the cell is 0.1 M NaCl solution at pH7.

"Potentiometry" and "chronopotentiometry" refer to taking a potentiometric measurement at one or more points in time.

A "redox mediator" is an electron transfer agent for carrying electrons between the analyte and the working electrode, either directly, or via a second electron transfer agent.

A "reference electrode" includes a reference electrode that also functions as a counter electrode (i.e., a counter/reference electrode) unless the description provides that a "reference electrode" excludes a counter/reference electrode.

A "second electron transfer agent" is a molecule that carries electrons between a redox mediator and the analyte.

"Sorbent material" is material that wicks, retains, and/or is wetted by a fluid sample and which typically does not substantially prevent diffusion of the analyte to the electrode.

A "surface in the sample chamber" includes a surface of a working electrode, counter electrode, counter/reference electrode, reference electrode, indicator electrode, a spacer, or any other surface bounding the sample chamber.

A "working electrode" is an electrode at which analyte is electrooxidized or electroreduced with or without the agency of a redox mediator.

A "working surface" is the portion of a working electrode that is covered with non-leachable redox mediator and exposed to the sample, or, if the redox mediator is diffusible, a "working surface" is the portion of the working electrode that is exposed to the sample.

The small volume, in vitro analyte sensors of the present invention are designed to measure the concentration of an analyte in a portion of a sample having a volume no more than about 1 µL, preferably no more than about 0.5 µL, more preferably no more than about 0.25 µL, and most preferably no more than about 0.1 µL. The analyte of interest is typically provided in a solution or biological fluid, such as blood or serum. Referring to the Drawings in general and FIGS. 1-4 in particular, a small volume, in vitro electrochemical sensor 20 of the invention generally includes a working electrode 22, a counter (or counter/reference) electrode 24, and a sample chamber 26 (see FIG. 4). The sample chamber 26 is configured so that when a sample is provided in the chamber the sample is in electrolytic contact with both the working electrode 22 and the counter electrode 24. This allows electrical current to flow between the electrodes to effect the electrolysis (electrooxidation or electroreduction) of the analyte.

Working Electrode

The working electrode 22 may be formed from a molded carbon fiber composite or it may consist of an inert non-conducting base material, such as polyester, upon which a suitable conducting layer is deposited. The conducting layer typically has relatively low electrical resistance and is typically electrochemically inert over the potential range of the sensor during operation. Suitable conducting layers include gold; carbon, platinum, ruthenium dioxide, palladium, and conductive epoxies, such as, for example, ECCOCOAT CT5079-3 Carbon-Filled Conductive Epoxy Coating (available from W.R. Grace Company, Woburn, Mass.), as well as other non-corroding materials known to those skilled in the art. The electrode (e.g., the conducting layer) is deposited on the surface of the inert material by methods such as vapor deposition or printing.

A tab 23 may be provided on the end of the working electrode 22 for easy connection of the electrode to external electronics (not shown) such as a voltage source or current measuring equipment. Other known methods or structures (such as contact pads) may be used to connect the working electrode 22 to the external electronics.

Figure 4:
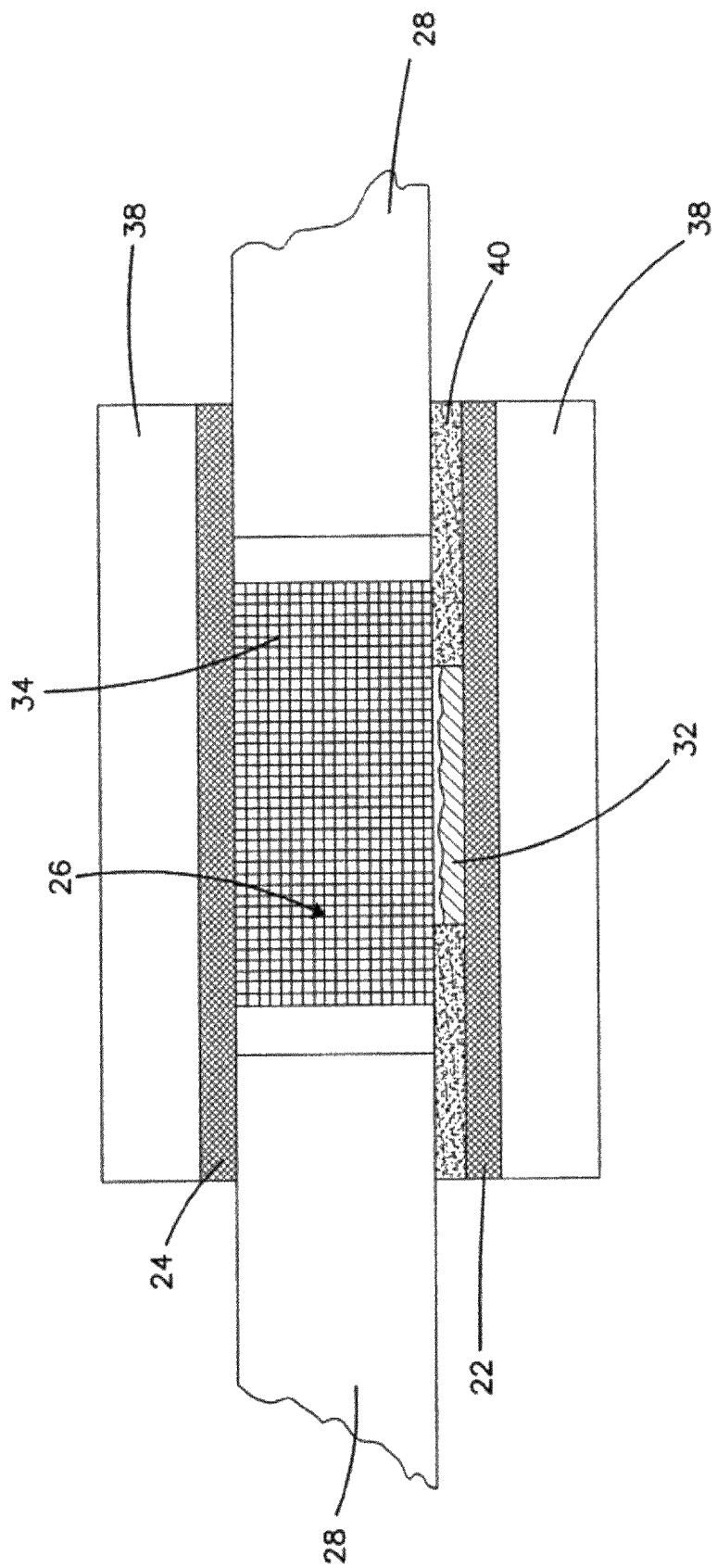
FIG. 4 is a not-to-scale side-sectional drawing of a portion of the sensor of FIG. 1 or 3 showing the relative positions of the redox mediator, the sample chamber, and the electrodes.

To prevent electrochemical reactions from occurring on portions of the working electrode not coated by the mediator, when a non-leachable mediator is used, a dielectric 40 may be deposited on the electrode over, under, or surrounding the region with the redox mediator, as shown in FIG. 4. Suitable dielectric materials include waxes and non-conducting organic polymers such as polyethylene. Dielectric 40 may also cover a portion of the redox mediator on the electrode. The covered portion of the redox mediator will not contact the sample, and, therefore, will not be a part of the electrode's working surface.

Sensing Chemistry

In addition to the working electrode 22, sensing chemistry materials are provided in the sample chamber 26 for the analysis of the analyte. This sensing chemistry preferably includes a redox mediator and a second electron transfer mediator, although in some instances, one or the other may be used alone. The redox mediator and second electron transfer agent can be independently diffusible or non-leachable (i.e., non-diffusible) such that either or both may be diffusible or non-leachable. Placement of sensor chemistry components may depend on whether they are diffusible or non-leachable. For example, non-leachable and/or diffusible component(s) typically form a sensing layer on the working electrode. Alternatively, one or more diffusible components may be disposed on any surface in the sample chamber prior to the introduction of the sample. As another example, one or more diffusible component(s) may be placed in the sample prior to introduction of the sample into the sensor.

If the redox mediator is non-leachable, then the non-leachable redox mediator is typically disposed on the working electrode 22 as a sensing layer 32. In an embodiment having a redox mediator and a second electron transfer agent, if the redox mediator and second electron transfer agent are both non-leachable, then both of the non-leachable components are disposed on the working electrode 22 as a sensing layer 32.

If, for example, the second electron transfer agent is diffusible and the redox mediator is non-leachable, then at least the redox mediator is disposed on the working electrode 22 as a sensing layer 32. The diffusible second electron transfer agent need not be disposed on a sensing layer of the working electrode, but may be disposed on any surface of the sample chamber, including within the redox mediator sensing layer, or may be placed in the sample. If the redox mediator is diffusible, then the redox mediator may be disposed on any surface of the sample chamber or may be placed in the sample.

If both the redox mediator and second electron transfer agent are diffusible, then the diffusible components may be independently or jointly disposed on any surface of the sample chamber and/or placed in the sample (i.e., each diffusible component need not be disposed on the same surface of the sample chamber or placed in the sample).

The redox mediator, whether it is diffusible or non-leachable, mediates a current between the working electrode 22 and the analyte and enables the electrochemical analysis of molecules which may not be suited for direct electrochemical reaction on an electrode. The mediator functions as an electron transfer agent between the electrode and the analyte.

In one embodiment, the redox mediator and second electron transfer agent are diffusible and disposed on the same surface of the sample chamber, such as, for example, on the working electrode. In this same vein, both can be disposed on, for example, the counter electrode, counter/reference electrode, reference electrode, or indicator electrode. In other instances, the redox mediator and second electron transfer agent are both diffusible and independently placed on a surface of the sample chamber and/or in the sample. For example, the redox mediator may be placed on the working electrode while the second electron transfer agent is placed on any surface, except for the working electrode, or is placed in the sample. Similarly, the reverse situation in which the second electron transfer agent is disposed on the working electrode and the redox mediator is disposed on any surface, except for the working electrode, or is placed in the sample is also a suitable embodiment. As another example, the redox mediator may be disposed on the counter electrode and the second electron transfer agent is placed on any surface except for the counter electrode or is placed in the sample. The reverse situation is also suitable.

The diffusible redox mediator and/or second electron transfer agent may diffuse rapidly into the sample or diffusion may occur over a period of time. Similarly, the diffusible redox mediator and/or second electron transfer agent may first dissolve from the surface on which it was placed as a solid and then the diffusible redox mediator and/or second electron transfer agent may diffuse into the sample, either rapidly or over a period of time. If the redox mediator and/or second electron transfer agent diffuse over a period of time, a user may be directed to wait a period of time before measuring the analyte concentration to allow for diffusion of the redox mediator and/or second electron transfer agent.

Background Signal

In at least some instances, a diffusible redox mediator may shuttle back and forth from the working electrode to the counter electrode even in the absence of analyte. This typically creates a background signal. For coulometric measurements, this background signal is referred to herein as "$Q_{Back}$." The background signal corresponds to the charge passed in an electrochemical assay in the absence of the analyte. The background signal typically has both a transient component and a steady-state component. At least a portion of the transient component may result, for example, from the establishment of a concentration gradient of the mediator in a particular oxidation state. At least a portion of the steady-state component may result, for example, from the redox mediator shuttling between the working electrode and counter or counter/reference electrode. Shuttling refers to the redox mediator being electrooxidized (or electroreduced) at the working electrode and then being electroreduced (or electrooxidized) at the counter or counter/reference electrode, thereby making the redox mediator available to be electrooxidized (or electroreduced) again at the working electrode so that the redox mediator is cycling between electrooxidation and electroreduction.

The amount of shuttling of the redox mediator, and therefore, the steady-state component of the background signal varies with, for example, the effective diffusion coefficient of the redox mediator, the viscosity of the sample, the temperature of the sample, the dimensions of the electrochemical cell, the distance between the working electrode and the counter or counter/reference electrode, and the angle between the working electrode and the counter or counter/reference electrode.

In some instances, the steady-state component of the background signal may contain noise associated with (a) variability in, for example, the temperature of the sample, the sample viscosity, or any other parameter on which the background signal depends during the duration of the assay, or (b) imperfections in the electrochemical cell, such as, for example, non-uniform separation between the working electrode and the counter or counter/reference electrode, variations in electrode geometry, or protrusions from the working electrode, the counter electrode, and/or the counter/reference electrode.

Although the steady-state component of the background signal may be reproducible, any noise inherently is not reproducible. As a result, the noise adversely affects accuracy. In some cases, the background signal and noise are related. As a result, the noise, and the error it introduces, can be reduced by reducing the background signal. For example, reducing the shuttling of the mediator between the working electrode and counter electrode or counter/reference electrode will likely reduce the noise associated with changes in sample temperature and viscosity which affect diffusion of the redox mediator.

Thus, to increase the accuracy of the measurements or to decrease error in the measurements in those instances when reducing a background signal also reduces noise, a moderate to near-zero level of background signal is desirable. In at least some instances, the sensor is constructed so that the background signal is at most five times the size of a signal generated by electrolysis of an amount of analyte. Preferably, the background signal is at most 200%, 100%, 50%, 25%, 10%, or 5% of the signal generated by electrolysis of the analyte. In the case of amperometry, this comparison may be made by determining the ratio of the current from the shuttling of the redox mediator to the current generated by the electrolysis of the analyte. In the case of potentiometry, this comparison may be made by determining the potential measurement from the shuttling of the redox mediator and the potential measurement generated by electrolysis of the analyte. In the case of coulometry, this comparison may be made by determining the charge transferred at the working electrode by the shuttling of the redox mediator and the charge transferred at the working electrode by the electrolysis of the analyte.

The size of the background signal may be compared to a predetermined amount of analyte. The predetermined amount of analyte in a sample may be, for example, an expected or average molar amount of analyte. The expected or average molar amount of analyte may be determined as, for example, the average value for users or individuals; an average value for a population; a maximum, minimum, or average of a normal physiological range; a maximum or minimum physiological value for a population; a maximum or minimum physiological value for users or individuals; an average, maximum, or minimum deviation outside a normal physiological range value for users, individuals, or a population; a deviation above or below an average value for a population; or an average, maximum, or minimum deviation above or below an average normal physiological value for users or individuals. A population may be defined by, for example, health, sex, or age, such as, for example, a normal adult, child, or newborn population. If a population is defined by health, the population may include people lacking a particular condition or alternatively, having a particular condition, such as, for example, diabetes. Reference intervals pertaining to average or expected values, such as, for example, those provided in *Tietz Textbook of Clinical Chemistry*, Appendix (pp. 2175-2217) (2nd Ed., Carl A. Burtis and Edward R. Ashwood, eds., W.D. Saunders Co., Philadelphia 1994) (incorporated herein by reference) may be used as guidelines, but a physical examination or blood chemistry determination by a skilled physician may also be used to determine an average or expected value for an individual. For example, an adult may have glucose in a concentration of 65 to 95 mg/dL in whole blood or L-lactate in a concentration of 8.1 to 15.3 mg/dL in venous whole blood after fasting, according to *Tietz Textbook of Clinical Chemistry*. An average normal physiological concentration for an adult, for example, may then correspond to 80 mg/dL for glucose or 12.7 mg/dL for lactate. Other examples include a person having juvenile onset diabetes, yet good glycemic control, and a glucose concentration between about 50 mg/dL and 400 mg/dL, thereby having an average molar amount of 225 mg/dL. In another instance, a non-diabetic adult may have a glucose concentration between about 80 mg/dL (after fasting) and 140 mg/dL (after consuming food), thereby having an average molar amount of 110 mg/dL.

Additional analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006, U.S. patent application having Ser. No. 09/145,776 and described in U.S. Provisional Patent Application Ser. Nos. 60/090,517, 60/093,100, and 60/114,919, incorporated herein by reference.

To construct a sensor having a particular ratio of background signal to analyte signal from electrolysis, several parameters relating to current and/or charge from the redox mediator shuttling background signal and/or from the signal generated by electrolysis of the analyte may be considered and chosen to obtain a desired ratio. Typically, the signal determined for a coulometric assay is the charge; whereas the signal determined for an amperometric assay is the current at the time when the measurement is taken. Because the current and charge depend on several parameters, the desired ratio for background signal generated by shuttling of the redox mediator to signal generated by electrolysis of the analyte may be accomplished by a variety of sensor configurations and methods for operating a sensor.

Controlling Background Signal

One method of controlling background signal includes using a redox mediator that a) oxidizes the analyte at a half wave potential, as measured by cyclic voltammetry in 0.1 M NaCl at pH 7, of no more than about +100 mV relative to the potential of a reference or counter/reference electrode or b) reduces the analyte at a half wave potential, as measured by cyclic voltammetry in 0.1 M NaCl at pH 7, of no less than about −100 mV relative to the potential of a reference or counter/reference electrode. A suitable reference or counter/reference electrode (e.g., a silver/silver chloride electrode) may be chosen. Preferably, the redox mediator a) oxidizes the analyte at a half wave potential, as measured by cyclic voltammetry in 0.1 M NaCl at pH 7, of no more than about +50 mV, +25 mV, 0 mV, −25 mV, −50 mV, −100 mV, or −150 mV relative to the potential of the reference or counter/reference electrode or b) reduces the analyte at a half wave potential, as measured by cyclic voltammetry in 0.1 M NaCl at pH 7, of no less than about −50 mV, −25 mV, 0 mV, +25 mV, +50 mV, +100 mV, +150 mV, or +200 mV relative to the potential of the reference or counter/reference electrode. Alternatively, in the case of reduction of the redox mediator by the counter electrode, the sensor is operated at an applied potential of no more than about +100 mV, +50 mV, +25 mV, 0 mV, −25 mV, −50 mV, −100 mV, or −150 mV between the working electrode and the counter or counter/reference electrode. In the case of oxidation of the redox mediator at the counter electrode, the sensor is operated at an applied potential of no less than about −100 mV, −50 mV, −25 mV, 0 mV, +25 mV, +50 mV, +100 mV, +150 mV, or +200 mV between the working electrode and the counter or counter/reference electrode.

Another method includes controlling the applied potential such that for an electrooxidative assay the redox mediator is not readily reduced at the counter or counter/reference electrode or for an electroreductive assay the redox mediator is not readily oxidized at the counter or counter/reference electrode. This can be accomplished, for example, in an electrooxidative assay by using a sensor having a diffusible redox mediator with a potential, relative to a reference or counter/reference electrode, that is negative with respect to the potential of the counter electrode (relative to a reference electrode) or the counter/reference electrode. The potential (relative to a reference or counter/reference electrode) of the working electrode is chosen to be positive with respect to the redox mediator and may be negative with respect to the counter or counter/reference electrode, so that the redox mediator is oxidized at the working electrode. For example, when the electrooxidation of an analyte is mediated by a diffusible redox mediator with a potential of −200 mV versus the reference or counter/reference electrode, and the potential at which the working electrode is poised is −150 mV relative to the reference or counter/reference electrode, then the redox mediator is substantially oxidized at the working electrode and will oxidize the analyte. Further, if some of the oxidized redox mediator reaches the counter or counter/reference electrode, the redox mediator will not be readily reduced at the counter or counter/reference electrode because the counter or counter/reference electrode is poised well positive (i.e., 150 mV) of the potential of the redox mediator.

In an electroreductive assay, a sensor is provided having a diffusible redox mediator with a formal potential, relative to a reference or counter/reference electrode, that is positive with respect to the potential of the counter or counter/reference electrode. The potential, relative to the reference or counter/reference electrode, of the working electrode is chosen to be negative with respect to the redox mediator and may be poised positive with respect to the counter or counter/reference electrode, so that the redox mediator is reduced at the working electrode.

Still another method of limiting background current includes having the redox mediator become immobilized when reacted on the counter electrode or counter/reference electrode by, for example, precipitation or polymerization. For example, the mediator may be cationic in the oxidized state, but neutral and much less soluble in the reduced state. Reduction at the counter/reference electrode leads to precipitation of the reduced, neutral mediator on the counter/reference electrode.

Another sensor configuration suitable for controlling background signal includes a sensor having a molar amount of redox mediator that is stoichiometrically the same as or less than an expected or average molar amount of analyte. The expected or average molar amount of analyte may be determined as already explained above. The expected or average molar amount of analyte may be determined as, for example, the average value for users or individuals; an average value for a population; a maximum, minimum, or average of a normal physiological range; a maximum or minimum physiological value for a population; a maximum or minimum physiological value for users or individuals; an average, maximum, or minimum deviation outside a normal physiological range value for users, individuals, or a population; a deviation above or below an average value for a population; or an average, maximum, or minimum deviation above or below an average normal physiological value for users or individuals. A population may be defined by, for example, health, sex, or age, such as, for example, a normal adult, child, or newborn population. If a population is defined by health, the population may include people lacking a particular condition or alternatively, having a particular condition, such as, for example, diabetes. Reference intervals pertaining to average or expected values, such as, for example, those provided in *Tietz Textbook of Clinical Chemistry*, supra, may be used as guidelines, but a physical examination or blood chemistry determination may also determine an average or expected value. For example, the physiological average molar amount of analyte may depend on the health or age of the person from whom the sample is obtained. This determination is within the knowledge of a skilled physician.

By reducing the concentration of the redox mediator relative to the concentration of the analyte, the signal attributable to the analyte relative to the signal attributable to the shuttling of the redox mediator is increased. In implementation of this method, the molar amount of redox mediator may be no more than 50%, 20%, 10%, or 5%, on a stoichiometric basis, of the expected or average molar amount of analyte.

The amount of redox mediator used in such a sensor configuration should fall within a range. The upper limit of the range may be determined based on, for example, the acceptable maximum signal due to shuttling of the redox mediator; the design of the electrochemical cell, including, for example, the dimensions of the cell and the position of the electrodes; the effective diffusion coefficient of the redox mediator; and the length of time needed for the assay. Moreover, the acceptable maximum signal due to redox mediator shuttling may vary from assay to assay as a result of one or more assay parameters, such as, for example, whether the assay is intended to be qualitative, semi-quantitative, or quantitative; whether small differences in analyte concentration serve as a basis to modify therapy; and the expected concentration of the analyte.

Although it is advantageous to minimize the amount of redox mediator used, the range for the acceptable amount of redox mediator does typically have a lower limit. The minimum amount of redox mediator that may be used is the concentration of redox mediator that is necessary to accomplish the assay within a desirable measurement time period, for example, no more than about 5 minutes or no more than about 1 minute. The time required to accomplish an assay depends on, for example, the distance between the working electrode and the counter or counter/reference electrode, the effective diffusion coefficient of the redox mediator, and the concentration of the analyte. In some instances, for example, when no kinetic limitations are present, i.e., shuttling of the redox mediator depends only on diffusion, the minimum concentration of redox mediator may be determined by the following formula:

$$C_m = (d^2 C_A)/D_m t$$

where $C_m$ is the minimum concentration of mediator required; d is the distance between a working electrode and a counter or counter/reference electrode in a facing arrangement; $C_A$ is the average analyte concentration in the sample; $D_m$ is the effective diffusion coefficient of the mediator in the sample; and t is the desired measurement time.

For example, when the distance between the facing electrode pair is 50 μm, the analyte being measured is 5 mM glucose, the redox mediator effective diffusion coefficient is $10^{-6}$ cm$^2$/sec and the desirable response time is no more than about 1 minute, then the minimum redox mediator concentration is 2.08 mM. Under these conditions the background signal will be less than the signal from the electrooxidation of the analyte.

Yet another sensor configuration for limiting the background current generated by a diffusible redox mediator includes having a barrier to the flow of the diffusible mediator to the counter electrode. The barrier can be, for example, a film through which the redox mediator can not diffuse or through which the redox mediator diffuses slowly. Examples of suitable films include polycarbonate, polyvinyl alcohol, and regenerated cellulose or cellulose ester membranes. Alternatively, the barrier can include charged or polar particles, compounds, or functional groups to prevent or reduce the flow of a charged redox mediator relative to the flow of a charge neutral or less charged analyte. If the redox mediator is positively charged, as are many of the osmium redox mediators described below, the barrier can be a positively charged or polar film, such as a methylated poly(1-vinyl imidazole). If the redox mediator is negatively charged, the barrier can be a negatively charged or polar film, such as Nafion®. Examples of suitable polar matrices include a bipolar membrane, a membrane having a cationic polymer cross-linked with an anionic polymer, and the like. In some instances, the barrier reduces the oxidation or reduction of the diffusible redox mediator at the counter electrode by at least 25%, 50%, or 90%.

Still another sensor configuration for limiting the background current includes a sensor having a redox mediator that is more readily oxidized or reduced on the working electrode than reduced or oxidized on the counter electrode. The rate of reaction of the redox mediator at an electrode can be a function of the material of the electrode. For example, some redox mediators may react faster at a carbon electrode than at a Ag/AgCl electrode. Appropriate selection of the electrodes may provide a reaction rate at one electrode that is significantly slower than the rate at the other electrode. In some instances, the rate of oxidation or reduction of the diffusible redox mediator at the counter electrode is reduced by at least 25%, 50%, or 90%, as compared to the working electrode. In some instances the rate of reaction for the redox mediator at the counter or counter/reference electrode is controlled by, for example, choosing a material for the counter or counter/reference electrode that would require an overpotential or a potential higher than the applied potential to increase the reaction rate at the counter or counter/reference electrode.

Another sensor configuration for limiting background current includes elements suitable for reducing the diffusion of the redox mediator. Diffusion can be reduced by, for example, using a redox mediator with a relatively low diffusion coefficient or increasing the viscosity of the sample in the measurement zone. In another embodiment, the diffusion of the redox mediator may be decreased by choosing a redox mediator with high molecular weight, such as, for example, greater than 5,000 daltons, preferably greater than 25,000 daltons, and more preferably greater than 100,000 daltons.

Redox Mediators

Although any organic or organometallic redox species can be used as a redox mediator, one type of suitable redox mediator is a transition metal compound or complex. Examples of suitable transition metal compounds or complexes include osmium, ruthenium, iron, and cobalt compounds or complexes. In these complexes, the transition metal is coordinatively bound to one or more ligands. The ligands are typically mono-, di-, tri-, or tetradentate. The most preferred ligands are heterocyclic nitrogen compounds, such as, for example, pyridine and/or imidazole derivatives. Multidentate ligands may include multiple pyridine and/or imidazole rings. Alternatively, metallocene derivatives, such as, for example, ferrocene, can be used.

Suitable redox mediators include osmium or ruthenium transition metal complexes with one or more ligands, each ligand having one or more nitrogen-containing heterocycles. Examples of such ligands include pyridine and imidazole rings and ligands having two or more pyridine and/or imidazole rings such as, for example, 2,2'-bipyridine; 2,2':6',2"-terpyridine; 1,10-phenanthroline; and ligands having the following structures:

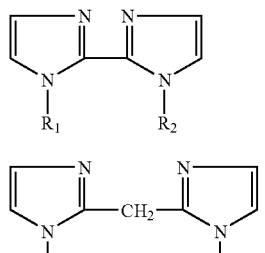
(I)

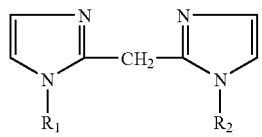
(II)

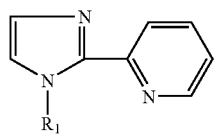
(III)

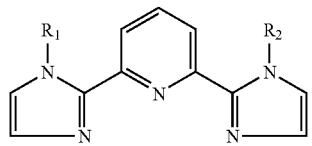
(IV)

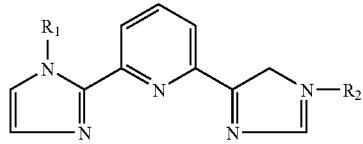
(V)

and derivatives thereof, wherein $R_1$ and $R_2$ are each independently hydrogen, hydroxy, alkyl, alkoxy, alkenyl, vinyl, allyl, amido, amino, vinylketone, keto, or sulfur-containing groups.

The term "alkyl" includes a straight or branched saturated aliphatic hydrocarbon chain having from 1 to 6 carbon atoms, such as for example, methyl, ethyl isopropyl (1-methylethyl), butyl, tert-butyl (1,1-dimethylethyl), and the like. Preferably the hydrocarbon chain has from 1 to 3 carbon atoms.

The term "alkoxy" includes an alkyl as defined above joined to the remainder of the structure by an oxygen atom, such as, for example, methoxy, ethoxy, propoxy, isopropoxy (1-methylethoxy), butoxy, tert-butoxy, and the like.

The term "alkenyl" includes an unsaturated aliphatic hydrocarbon chain having from 2 to 6 carbon atoms, such as, for example, ethenyl, 1-propenyl, 2-propenyl, 1-butenyl, 2-methyl-1-propenyl, and the like. Preferably the hydrocarbon chain has from 2 to 3 carbon atoms.

The term "amido" includes groups having a nitrogen atom bonded to the carbon atom of a carbonyl group and includes groups having the following formulas:

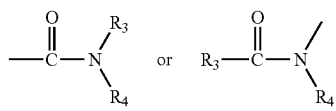

wherein $R_3$ and $R_4$ are each independently hydrogen, alkyl, alkoxy, or alkenyl.

The term "amino" as used herein includes alkylamino, such as methylamino, diethylamino, N,N-methylethylamino and the like; alkoxyalkylamino, such as N-(ethoxyethyl) amino, N,N-di(methoxyethyl)amino, N,N-(methoxyethyl) (ethoxyethyl)amino, and the like; and nitrogen-containing rings, such as piperidino, piperazino, morpholino, and the like.

The term "vinylketone" includes a group having the formula:

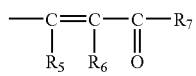

wherein $R_5$, $R_6$, and $R_7$ are each independently hydrogen, alkyl, alkoxy, or alkenyl.

The term "keto" includes a group having the formula:

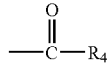

wherein $R_8$ is hydrogen, alkyl, alkoxy, or alkenyl.

The term "sulfur-containing group" includes mercapto, alkylmercapto (such as methylmercapto, ethylmercapto, and the like), alkoxyalkylmercapto (such as methoxyethylmercapto and the like), alkylsulfoxide (such as methylsulfoxide and propylsulfoxide and the like), alkoxyalkylsulfoxide (such as ethoxyethylsulfoxide and the like), alkylsulfone (such as methylsulfone and propylsulfone and the like), and alkoxyalkylsulfone (such as methoxyethylsulfone and the like). Preferably, the sulfur-containing group is a mercapto group.

Other suitable redox mediators include osmium or ruthenium transition metal complexes with one or more ligands, each ligand having one or more nitrogen-containing heterocycles and each nitrogen-containing heterocycle having a second heteroatom selected from the group consisting of nitrogen, oxygen, sulfur, and selenium.

Examples of ligands having one or more nitrogen-containing heterocycles and in which each heterocycle has a second heteroatom include ligands having the following structures:

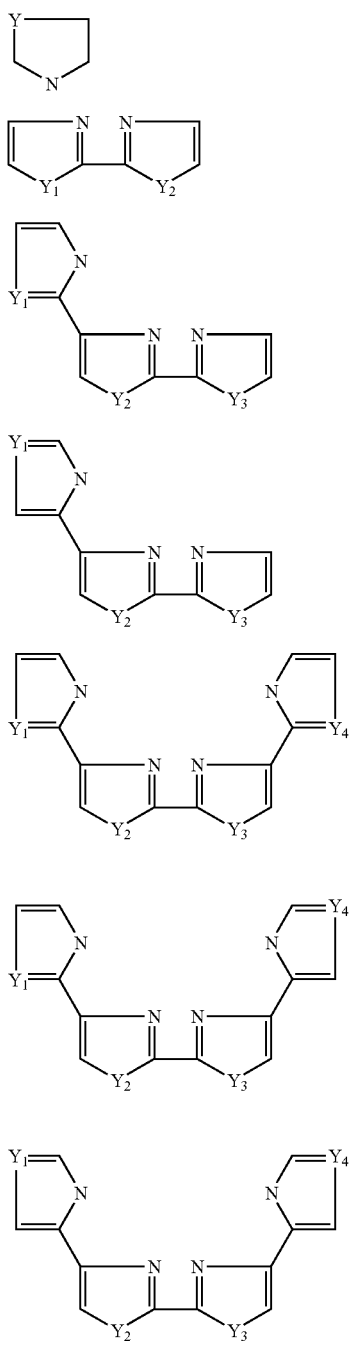

(VI)
(VII)
(VIII)
(IX)
(X)
(XI)
(XII)

wherein $Y_1$, $Y_2$, $Y_3$, and $Y_4$ are each independently an oxygen atom, a sulfur atom, a selenium atom, or a substituted nitrogen atom having the formula $NR_9$ wherein $R_9$ is hydrogen, hydroxy, alkyl, alkoxy, alkenyl, amido, amino, vinylketone, keto, or sulfur-containing group. The terms "alkyl," "alkoxy," "alkenyl," "amido," "amino," "vinylketone," "keto," and "sulfur-containing group" are as defined above.

Suitable derivatives of these ligands include, for example, the addition of alkyl, alkoxy, alkenyl, vinylester, and amido functional groups to any of the available sites on the heterocyclic ring, including, for example, on the 4-position (i.e., para to nitrogen) of the pyridine rings or on one of the nitrogen atoms of the imidazole ring.

Suitable derivatives of 2,2'-bipyridine for complexation with the osmium cation include, for example, mono-, di-, and polyalkyl-2,2'-bipyridines, such as 4,4'-dimethyl-2,2'-bipyridine; mono-, di-, and polyalkoxy-2,2'-bipyridines, such as 4,4'-dimethoxy-2,2'-bipyridine and 2,6'-dimethoxy-2,2'-bipyridine; mono-, di-, and polyacetamido-2,2'-bipyridines, such as 4,4'-di(acetamido)-2,2'-bipyridine; mono-, di-, and polyalkylaminoalkoxy-2,2'-bipyridines, such as 4,4'-di(N,N-dimethylaminoethoxy)-2,2'-bipyridine; and substituted mono-, di-, and polypyrazolyl-2,2'-bipyridines, such as 4,4'-dimethoxy-6-(N-pyrazolyl)-2,2'-bipyridine and 4,4'-dimethoxy-6-(N-pyrazolylmethyl)-2,2'-bipyridine.

Suitable derivatives of 1,10-phenanthroline for complexation with the osmium cation include, for example, mono-, di-, and polyalkyl-1,10-phenanthrolines, such as 4,7-dimethyl-1,10-phenanthroline, and mono, di-, and polyalkoxy-1,10-phenanthrolines, such as 4,7-dimethoxy-1,10-phenanthroline and 5-methoxy-1,10-phenanthroline.

Suitable derivatives for 2,2':6',2''-terpyridine include, for example, mono-, di-, tri-, and polyalkyl-2,2':6',2''-terpyridines, such as 4,4',4''-trimethyl-2,2':6',2''-terpyridine, 4,4',4''-triethyl-2,2':6',2''-terpyridine, and mono-, di-, tri-, and polyalkoxy-2,2':6',2''-terpyridines, such as 4,4',4''-trimethoxy-2,2':6',2''-terpyridine and 4'-methoxy-2,2':6',2''-terpyridine, and mono-, di-, tri-, and polyamino-2,2':6',2''-terpyridine, such as 4'-amino-2,2':6',2''-terpyridine, and mono-, di-, tri-, and polyalkylamino-2,2':6',2''-terpyridine, such as 4'-dimethylamino-2,2':6',2''-terpyridine, and mono-, di-, tri-, and polyalkylthio-2,2':6',2''-terpyridine such as 4'-methylthio-2,2':6',2''-terpyridine and 4-methylthio-4'-ethylthio-2,2':6',2''-terpyridine.

Suitable derivatives for pyridine include, for example, mono-, di-, tri-, and polysubstituted pyridines, such as 2,6-bis(N-pyrazolyl)pyridine, 2,6-bis(3-methyl-N-pyrazolyl)pyridine, 2,6-bis(2-imidazolyl)pyridine, 2,6-bis(1-methyl-2-imidazolyl)pyridine, and 2,6-bis(1-vinyl-2-imidazolyl) pyridine, and mono-, di-, tri-, and polyaminopridines, such as 4-aminopyridine, 4,4'-di(dimethylamino)bipyridine, and 4,4',4''-triamino terpyridine.

Other suitable derivatives include compounds comprising three heterocyclic rings. For example, one suitable derivative includes a compound of the formula:

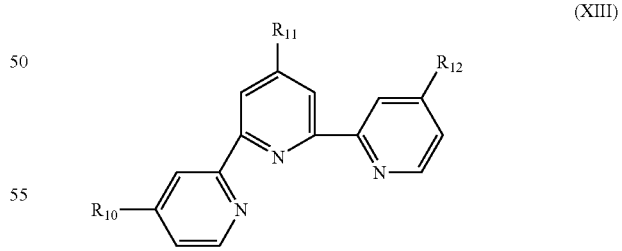

(XIII)

wherein $R_{10}$, $R_{11}$, and $R_{12}$ are each independently hydrogen, hydroxy, alkyl, alkoxy, alkenyl, vinyl, allyl, amido, amino, vinylketone, keto, or sulfur-containing group.

The terms "alkyl," "alkoxy," "alkenyl," "amido," "amino," "vinylketone," "keto," and "sulfur-containing group" are as defined above.

Other suitable redox mediator derivatives include compounds of the formula:

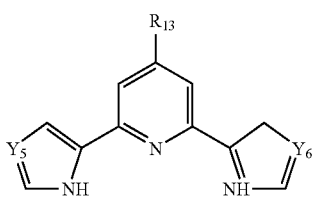

(XIV)

wherein $R_{13}$ is hydrogen, hydroxy, alkyl, alkoxy, alkenyl, vinyl, allyl, vinylketone, keto, amide, amino, or sulfur-containing group; and $Y_5$ and $Y_6$ are each independently a nitrogen or carbon atom.

The terms "alkyl," "alkoxy," "alkenyl," "amido," "amino," "vinylketone," "keto," and "sulfur-containing group" are as defined above.

Still other suitable derivatives include compounds of the formula:

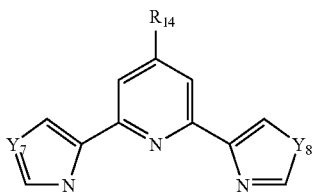

(XV)

wherein $R_{14}$ is as defined above and $Y_7$ and $Y_8$ are each independently a sulfur or oxygen atom.

Examples of suitable redox mediators also include, for example, osmium cations complexed with (a) two bidentate ligands, such as 2,2'-bipyridine, 1,10-phenanthroline, or derivatives thereof (the two ligands not necessarily being the same), (b) one tridentate ligand, such as 2,2',2''-terpyridine and 2,6-di(imidazol-2-yl)-pyridine, or (c) one bidentate ligand and one tridentate ligand. Suitable osmium transition metal complexes include, for example, $[(bpy)_2OsLX]^{+/2+}$, $[(dimet)_2OsLX]^{+/2+}$, $[(dmo)_2OsLX]^{+/2+}$, $[terOsLX_2]^{0/+}$, $[trimetOsLX_2]^{0/+}$, and $[(ter)(bpy)LOs]^{+2+/3+}$ where bpy is 2,2'-bipyridine, dimet is 4,4'-dimethyl-2,2'-bipyridine, dmo is 4,4'-dimethoxy-2,2'-bipyridine, ter is 2,2':6',2''-terpyridine, trimet is 4,4',4''-trimethyl-2,2':6',2''-terpyridine, L is a nitrogen-containing heterocyclic ligand, and X is a halogen, such as fluorine, chlorine, or bromine.

The redox mediators often exchange electrons rapidly with each other and with the electrode so that the complex can be rapidly oxidized and/or reduced. In general, iron complexes are more oxidizing than ruthenium complexes, which, in turn, are more oxidizing than osmium complexes. In addition, the redox potential generally increases with the number of coordinating heterocyclic rings; six-membered heterocyclic rings increase the potential more than five membered rings, except when the nitrogen coordinating the metal is formally an anion. This is the case only if the nitrogen in the ring is bound to both of its neighboring carbon atoms by single bonds. If the nitrogen is formally an anion then the redox potential generally increases more upon coordination of the metal ion.

At least some diffusible redox mediators include one or more pyridine or imidazole functional groups. The imidazole functional group can also include other substituents and can be, for example, vinyl imidazole, e.g., 1-vinyl imidazole, or methylimidazole, e.g., 1-methylimidazole. Examples of suitable diffusible mediators may include $[Os(dmo)_2(1\text{-vinyl}$ imidazole)X]X, $[Os(dmo)_2(1\text{-vinyl imidazole})X]X_2$, $[Os(dmo)_2(imidazole)X]X$, $[Os(dmo)_2(imidazole)X]X_2$, $[Os(dmo)_2(1\text{-methylimidazole})X]X_2$, and $[Os(dmo)_2(\text{methylimidazole})X]X_2$, where dmo is 4,4'-dimethoxy-2,2'-bipyridine, and X is halogen as described above.

Other osmium-containing redox mediators include $[Os((\text{methoxy})_2\text{phenanthroline})_2(\text{N-methylimidazole})X]^{+/2+}$; $[Os((\text{acetamido})_2\text{bipyridine})_2(L)X]^{+/2+}$, where L is a monodentate nitrogen-containing compound (including, but not limited to, an imidazole derivative) chosen to refine the potential; and $Os(\text{terpyridine})(L)_2Cl$, where L is an aminopyridine, such as a dialkylaminopyridine; an N-substituted imidazole, such as N-methyl imidazole; an oxazole; a thiazole; or an alkoxypyridine, such as methoxypyridine. X is halogen as described above.

Osmium-free diffusible redox mediators include, for example, phenoxazines, such as, 7-dimethylamino-1,2-benzophenoxazine (Meldola Blue), 1,2-benzophcnoxazine, and Nile Blue; 3-β-naphthoyl (Brilliant Cresyl Blue); tetramethylphenylenediamine (TMPD); dichlorophenolindophenol (DCIP); N-methyl phenazonium salts, for example, phenazine methosulfate (PMS), N-methylphenazine methosulfate and methoxyphenazine methosulfate; tetrazolium salts, for example, tetrazolium blue or nitrotetrazolium blue; and phenothiazines, for example, toluidine blue O.

Examples of other redox species include stable quinones and species that in their oxidized state have quinoid structures, such as Nile Blue and indophenol. Examples of suitable quinones include, for example, derivatives of naphthoquinone, phenoquinone, benzoquinone, naphthenequinone, and the like. Examples of naphthoquinone derivatives include juglone (i.e., 5-hydroxy-1,4-naphthoquinone) and derivatives thereof, such as, for example, 2,3-dichloro-5,8-dihydroxy-1,4-naphthoquinone, 2,3-dimethyl-5,8-dihydroxy-1,4-naphthoquinone, 2-chloro-5,8-dihydroxy-1,4-naphthoquinone, 2,3-methoxy-5-hydroxy-1,4-naphthoquinone, and the like. Other examples include aminonaphthoquinones, such as, for example, morpholino-naphthoquinones, such as 2-chloro-3-morpholino-1,4-naphthoquinone; piperidino-naphthoquinones, such as 2-methyl-3-peperidino-1,4-naphthoquinone; piperazino-naphthoquinones, such as 2-ethoxy-3-piperazino-1,4-naphthoquinone; and the like.

Suitable phenoquinone derivatives include, for example, coerulignone (i.e., 3,3',5,5'-tetramethoxydiphenoquinone) and derivatives thereof, such as, for example, 3,3',5,5'-tetramethyldiphenoquinone, 3,3',5,5'-tetrahydroxydiphenoquinone, and the like.

Suitable benzoquinone derivatives include, for example, coenzyme $Q_0$ (i.e., 2,3-dimethoxy-5-methyl-1,4-benzoquinone) and derivatives thereof, such as, for example, 2,3,5-trimethyl-1,4-benzoquinone, 2,3-dimethyl-5-methoxy-1,4-benzoquinone, 2,3-dimethyl-5-hydroxy-1,4-benzoquinone, and the like.

Other suitable quinone derivatives include, for example, acenaphthenequinone and ubiquinones, such as, for example, coenzyme Q, including $Q_1$, $Q_2$, $Q_6$, $Q_7$, $Q_9$, and $Q_{10}$.

Still other suitable osmium-free diffusible redox mediators include, for example, Taylor's blue (i.e., 1,9-dimethylmethylene blue), N,N'-diethylthiacyanine iodide, and thionine.

In another method, a sensing layer 32 contains a non-leachable (i.e., non-releasable) redox mediator and is disposed on a portion of the working electrode 22. The non-leachable redox mediator can be, for example, a redox polymer (i.e., a polymer having one or more redox species). Preferably, there is little or no leaching of the non-leachable redox mediator away from the working electrode 22 into the sample during the measurement period, which is typically less than about 5 minutes. The redox mediators of this embodiment can be bound or otherwise immobilized on the working electrode 22 to prevent leaching of the mediator into the sample. The redox mediator can be bound or otherwise immobilized on the working electrode by known methods, for example, formation of multiple ion bridges with a counter-charged polyelectrolyte, covalent attachment of the redox mediator to a polymer on the working electrode, entrapment of the redox mediator in a matrix that has a high affinity for the redox mediator, or bioconjugation of the redox mediator with a compound bound to the working electrode. In one embodiment, a cationic exchange membrane may be used to entrap an anionic redox compound. Similarly, in another embodiment, an anionic exchange membrane may be used to entrap a cationic redox compound. In still another embodiment involving bioconjugation, a biotin-bound redox mediator can conjugate with avidin or straptavidin in a matrix near or immobilized on the working electrode. Still another embodiment includes having a digoxin or digoxigenin redox mediator react with antidigoxin in a matrix near or immobilized on a working electrode.

Preferred non-leachable redox mediators are redox polymers, such as polymeric transition metal compounds or complexes. Typically, the polymers used to form a redox polymer have nitrogen-containing heterocycles, such as pyridine, imidazole, or derivatives thereof for binding as ligands to the redox species. Suitable polymers for complexation with redox species, such as the transition metal complexes, described above, include, for example, polymers and copolymers of poly(1-vinyl imidazole) (referred to as "PVI") and poly(4-vinyl pyridine) (referred to as "PVP"), as well as polymers and copolymers of poly(acrylic acid) or polyacrylamide that have been modified by the addition of pendant nitrogen-containing heterocycles, such as pyridine and imidazole. Modification of poly(acrylic acid) may be performed by reaction of at least a portion of the carboxylic acid functionalities with an aminoalkylpyridine or aminoalkylimidazole, such as 4-ethylaminopyridine, to form amides. Suitable copolymer substituents of PVI, PVP, and poly(acrylic acid) include acrylonitrile, acrylamide, acrylhydrazide, and substituted or quaternized 1-vinyl imidazole. The copolymers can be random or block copolymers.

The transition metal complexes of non-leachable redox polymers are typically covalently or coordinatively bound with the nitrogen-containing heterocycles (e.g., imidazole and/or pyridine rings) of the polymer. The transition metal complexes may have vinyl functional groups through which the complexes can be co-polymerized. Suitable vinyl functional groups include, for example, vinylic heterocycles, amides, nitriles, carboxylic acids, sulfonic acids, or other polar vinylic compounds. An example of a redox polymer of this type is poly(vinyl ferrocene) or a derivative of poly(vinyl ferrocene) functionalized to increase swelling of the redox polymer in water.

Another type of redox polymer contains an ionically-bound redox species, by forming multiple ion-bridges. Typically, this type of mediator includes a charged polymer coupled to an oppositely charged redox species. Examples of this type of redox polymer include a negatively charged polymer such as Nafion® (DuPont) coupled to multiple positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. The preferred ionically-bound redox species is a multiply charged, often polyanionic, redox species bound within an oppositely charged polymer.

Another suitable redox polymer includes a redox species coordinatively bound to a polymer. For example, the mediator may be formed by coordination of an osmium, ruthenium, or cobalt 2,2'-bipyridyl complex to poly(1-vinyl imidazole) or poly(4-vinyl pyridine) or by co-polymerization of, for example, a 4-vinyl-2,2'-bipyridyl osmium, ruthenium, or cobalt complex with 1-vinyl imidazole or 4-vinyl pyridine.

Typically, the ratio of osmium or ruthenium transition metal complexes to imidazole and/or pyridine groups of the non-leachable redox polymers ranges from 1:20 to 1:1, preferably from 1:15 to 1:2, and more preferably from 1:10 to 1:4. Generally, the redox potentials depend, at least in part, on the polymer with the order of redox potentials being poly(acrylic acid)<PVI<PVP.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking. The polymer of the redox polymer may contain functional groups, such as, for example, hydrazide, amine, alcohol, heterocyclic nitrogen, vinyl, allyl, and carboxylic acid groups, that can be crosslinked using a crosslinking agent. These functional groups may be provided on the polymer or one or more of the copolymers. Alternatively or additionally, the functional groups may be added by a reaction, such as, for example, quaternization. One example is the quaternization of PVP with bromoethylamine groups.

Suitable cross-linking agents include, for example, molecules having two or more epoxide (e.g., poly(ethylene glycol) diglycidyl ether (PEGDGE)), aldehyde, aziridine, alkyl halide, and azide functional groups or combinations thereof. When a polymer has multiple acrylate functions, it can be crosslinked with a di- or polythiol; when it has multiple thiol functions it can be crosslinked with a di- or polyacrylate. Other examples of cross-linking agents include compounds that activate carboxylic acid or other acid functional groups for condensation with amines or other nitrogen compounds. These cross-linking agents include carbodiimides or compounds with active N-hydroxysuccinimide or imidate functional groups. Yet other examples of cross-linking agents are quinones (e.g., tetrachlorobenzoquinone and tetracyanoquinodimethane) and cyanuric chloride. Other cross-linking agents may also be used. In some embodiments, an additional cross-linking agent is not required. Further discussion and examples of cross-linking and cross-linking agents are found in U.S. Pat. Nos. 5,262,035; 5,262,305; 5,320,725; 5,264,104; 5,264,105; 5,356,786; and 5,593,852, herein incorporated by reference.

In another embodiment, the redox polymer is immobilized by the functionalization of the electrode surface and then the chemical bonding, often covalently, of the redox polymer to the functional groups on the electrode surface. One example of this type of immobilization begins with a poly(4-vinyl pyridine). The polymer's pyridine rings are, in part, complexed with a reducible/oxidizable species, such as $[Os(bpy)_2 Cl]^{+/2+}$ where bpy is 2,2'-bipyridine. Part of the pyridine rings are quaternized by reaction with 2-bromoethylamine. The polymer is then crosslinked, for example, using a diepoxide, such as poly(ethylene glycol) diglycidyl ether.

Carbon surfaces can be modified for attachment of a redox polymer, for example, by electroreduction of a diazonium salt. As an illustration, reduction of a diazonium salt formed upon diazotization of p-aminobenzoic acid modifies a carbon surface with phenylcarboxylic acid functional groups. These functional groups can be activated by a carbodiimide, such as 1-ethyl-3-(3-dimethylaminopropyl)-carbodiimide hydrochloride (EDC). The activated functional groups are bound with an amine-functionalized redox couple, such as, for example, the quaternized osmium-containing redox polymer described above or 2-aminoethylferrocene, to form the redox couple.

Similarly, gold and other metal surfaces can be functionalized by, for example, an amine, such as cystamine, or by a carboxylic acid, such as thioctic acid. A redox couple, such as, for example, $[Os(bpy)_2(pyridine-4-carboxylate)Cl]^{0/+}$, is activated by 1-ethyl-3-(3-dimethylaminopropyl)-carbodiimide hydrochloride (EDC) to form a reactive O-acylisourea which reacts with the gold-bound amine to form an amide. The carboxylic acid functional group of thioctic acid can be activated with EDC to bind a polymer or protein amine to form an amide.

When the enzyme used is PQQ glucose dehydrogenase or glucose oxidase, the preferred non-leachable redox mediators have a redox potential between about −300 mV to about +400 mV versus the standard calomel electrode (SCE). The most preferred non-leachable redox mediators have osmium redox centers and a redox potential more negative than +100 mV versus SCE, more preferably the redox potential is more negative than 0 mV versus SCE, and most preferably is near −150 mV versus SCE.

In at least some instances, the redox mediators of the sensors are air-oxidizable. This means that the redox mediator is oxidized by air, preferably, so that at least 90% of the mediator is in an oxidized state prior to introduction of sample into the sensor. Air-oxidizable redox mediators include osmium cations complexed with two mono-, di-, or polyalkoxy-2,2'-bipyridine or mono-, di-, or polyalkoxy-1,10-phenanthroline ligands, the two ligands not necessarily being the same, and further complexed with polymers or other ligands having pyridine and imidazole functional groups. In particular, $Os[4,4'\text{-dimethoxy-2,2'-bipyridine}]_2Cl^{+/+2}$ complexed with poly (4-vinyl pyridine) or poly(1-vinyl imidazole) attains approximately 90% or more oxidation in air. The air oxidation of the redox mediator may take place while the redox mediator is a solid, such as, for example, when it is coated on the sensor in a dry state and stored. Alternatively, the air oxidation of the redox mediator may take place while the redox mediator is in solution, such as, for example, prior to the solution being applied onto the sensor and dried. In the case in which the redox mediator is air oxidized in solution, the solution containing the redox mediator may be kept in storage for a period of time sufficient to air oxidize the mediator prior to use of the solution in the manufacturing process.

Second Electron Transfer Agent

In a preferred embodiment of the invention, the sensor includes a redox mediator and a second electron transfer agent which is capable of transferring electrons to or from the redox mediator and the analyte. The second electron transfer agent may be diffusible or may be non-leachable (e.g., entrapped in or coordinatively, covalently, or ionically bound to the redox polymer). One example of a suitable second electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. A lactate oxidase fills this role when the analyte is lactate. Other enzymes can be used for other analytes. These enzymes catalyze the electrolysis of an analyte by transferring electrons between the analyte and the electrode via the redox mediator.

In some embodiments, the second electron transfer agent is non-leachable, and more preferably immobilized on the working electrode, to prevent unwanted leaching of the agent into the sample. This is accomplished, for example, by cross-linking the non-leachable second electron transfer agent with the non-leachable redox mediator, thereby providing a sensing layer with non-leachable components on the working electrode. In other embodiments, the second electron transfer agent is diffusible (and may be disposed on any surface of the sample chamber or placed in the sample).

Counter Electrode

Counter electrode 24, as illustrated in FIGS. 1-4, may be constructed in a manner similar to working electrode 22. Counter electrode 24 may also be a counter/reference electrode. Alternatively, a separate reference electrode may be provided in contact with the sample chamber. Suitable materials for the counter/reference or reference electrode include Ag/AgCl or Ag/AgBr printed on a non-conducting base material or silver chloride on a silver metal base. The same materials and methods may be used to make the counter electrode as are available for constructing the working electrode 22, although different materials and methods may also be used. A tab 25 may be provided on the electrode for convenient connection to the external electronics (not shown), such as a coulometer, potentiostat, or other measuring device.

Electrode Configuration

Figure 3:
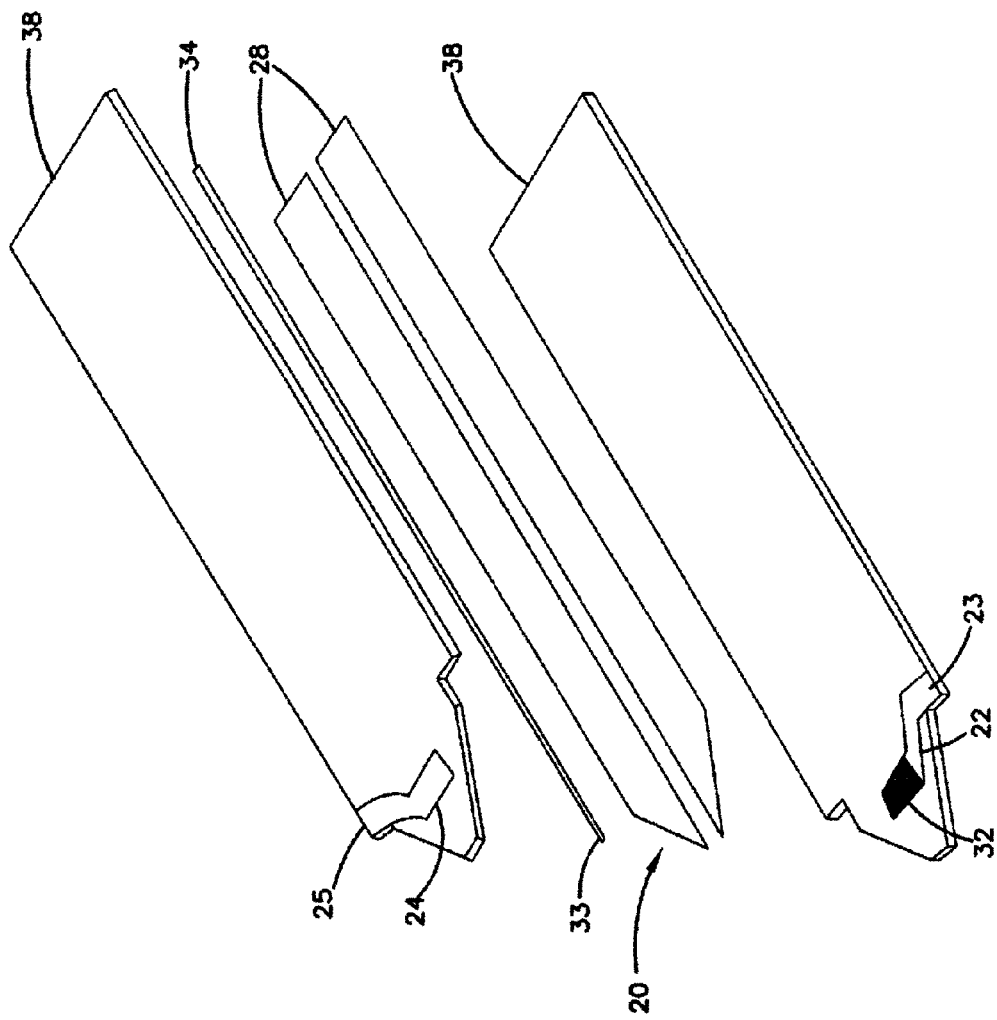
FIG. 3 is a schematic view of a third embodiment of an electrochemical sensor in accordance with the principles of the present invention having a working electrode and a counter electrode facing each other and having an extended sample chamber.

In one embodiment of the invention, working electrode 22 and counter electrode 24 are disposed opposite to and facing each other to form a facing electrode pair as depicted in FIGS. 1 and 3. In this preferred configuration, the sample chamber 26 is typically disposed between the two electrodes. For this facing electrode configuration; it is preferred that the electrodes are separated by a distance of no more than about 0.2 mm (i.e., at least one portion of the working electrode is separated from one portion of the counter electrode by no more than 200 μm), preferably no more than 100 μm, and most preferably no more than 50 μm.

The electrodes need not be directly opposing each other; they may be slightly offset. Furthermore, the two electrodes need not be the same size. Preferably, the counter electrode 24 is at least as large as the working surface of the working electrode 22. The counter electrode 22 can also be formed with tines in a comb shape. Other configurations of both the counter electrode and working electrode are within the scope of the invention. However, for this particular embodiment, the separation distance between at least one portion of the working electrode and some portion of the counter electrode preferably does not exceed the limits specified hereinabove.

Figure 11A:
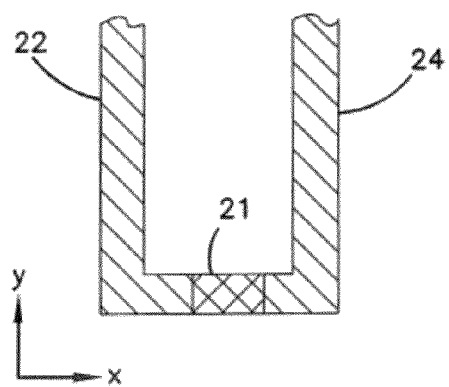
FIGS. 11A, 11B, and 11C are top views of three configurations for overlapping working and counter electrodes according to the present invention.
Figure 11B:
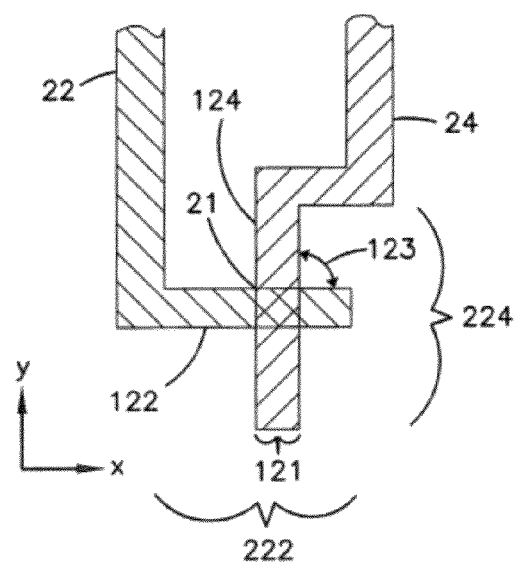
Figure 11C:
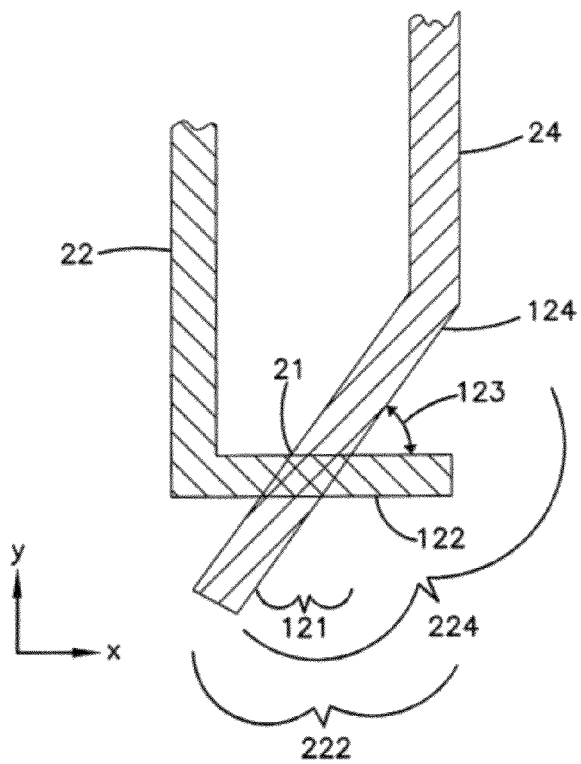

FIGS. 11A, 11B, and 11C illustrate different embodiments of pairs of facing electrodes 22, 24, as described above. A region 21 of overlap between the two electrodes 22, 24 typically corresponds to the measurement zone in which the sample will be interrogated. Each of the electrodes 22, 24 is a conducting surface and acts as a plate of a capacitor. The measurement zone between the electrodes 22, 24 acts as a dielectric layer between the plates. Thus, there is a capacitance between the two electrodes 22, 24. This capacitance is a function of the size of the overlapping electrodes 22, 24, the separation between the electrodes 22, 24, and the dielectric constant of the material between the electrodes 22, 24. Thus, if the size of the region 21 of the overlapping electrodes 22, 24 and the dielectric constant of the material between the electrodes (e.g., air or a sorbent material) are known, then the separation between the electrodes can be calculated to determine the volume of the measurement zone.

FIG. 11A illustrates one embodiment of the invention in which the electrodes 22, 24 are positioned in a facing arrangement. For the capacitance to be uniform among similarly constructed analyte sensors having this particular sensor configuration, the registration (i.e., the positioning of the two electrodes relative to one another) should be uniform. If the position of either of the electrodes is shifted in the x-y plane from the position shown in FIG. 11A, the size of the overlap, and therefore, of the capacitance, will change. The same principle holds for the volume of the measurement zone.

FIGS. 11B and 11C illustrate other embodiments of the invention with electrodes 22, 24 in a facing arrangement. In these particular arrangements, the position of either of the electrodes may be shifted, by at least some minimum distance, in the x-y plane relative to the other electrode without a change in the capacitance or the volume of the measurement zone. In these electrode arrangements, each electrode 22, 24 includes an arm 122, 124, respectively, which overlaps with the corresponding arm of the other electrode. The two arms 122, 124 are not parallel to each other (such as illustrated in FIG. 11A); rather, the arms 122, 124 are disposed at an angle 123, which is greater than zero, relative to each other. In addition, the two arms 122, 124 extend beyond the region 21 of overlap (i.e., each arm has extra length corresponding to the difference between the length of the arm 222, 224, respectively, and the width 121 of the overlap 21). With these electrode arrangements, there can be a certain amount of allowed imprecision in the registration of the electrodes 22, 24 which does not change the capacitance of the electrode arrangement. A desired amount of allowed imprecision in the registration can be designed into the electrode arrangement by varying the angle 123 at which the arms 122, 124 overlap and the size of the extra length of each arm 122, 124 relative to the width 121 of the region 21 of overlap. Typically, the closer that the arms 122, 124 are to being perpendicular (i.e., angle 123 is 90°), the greater the allowed imprecision. Also, the greater the extra length of each arm 122, 124 (which may both be the same length or different lengths) relative to the width 121 of the region 21 of overlap, the greater the allowed imprecision. Conversely, the greater the amount of allowed imprecision, the larger the size of the electrodes (for a given electrode width, thickness, and angle 123 of intersection with the other electrode). Thus, the minimum distance that one electrode can be shifted relative to the other is balanced against the amount of material needed for the electrodes. Typically, the angle 123 of intersection ranges from 5 to 90 degrees, preferably, 30 to 90 degrees, and more preferably 60 to 90 degrees. Typically, the ratio of the extra length of an arm 122, 124 (corresponding to the difference between the arm length 222, 224 and the width 121 of the region 21 of overlap) versus the width 121 of the region 21 of overlap ranges from 0.1:1 to 50:1, preferably 1:1 to 15:1, and more preferably 4:1 to 10:1.

Figure 2:
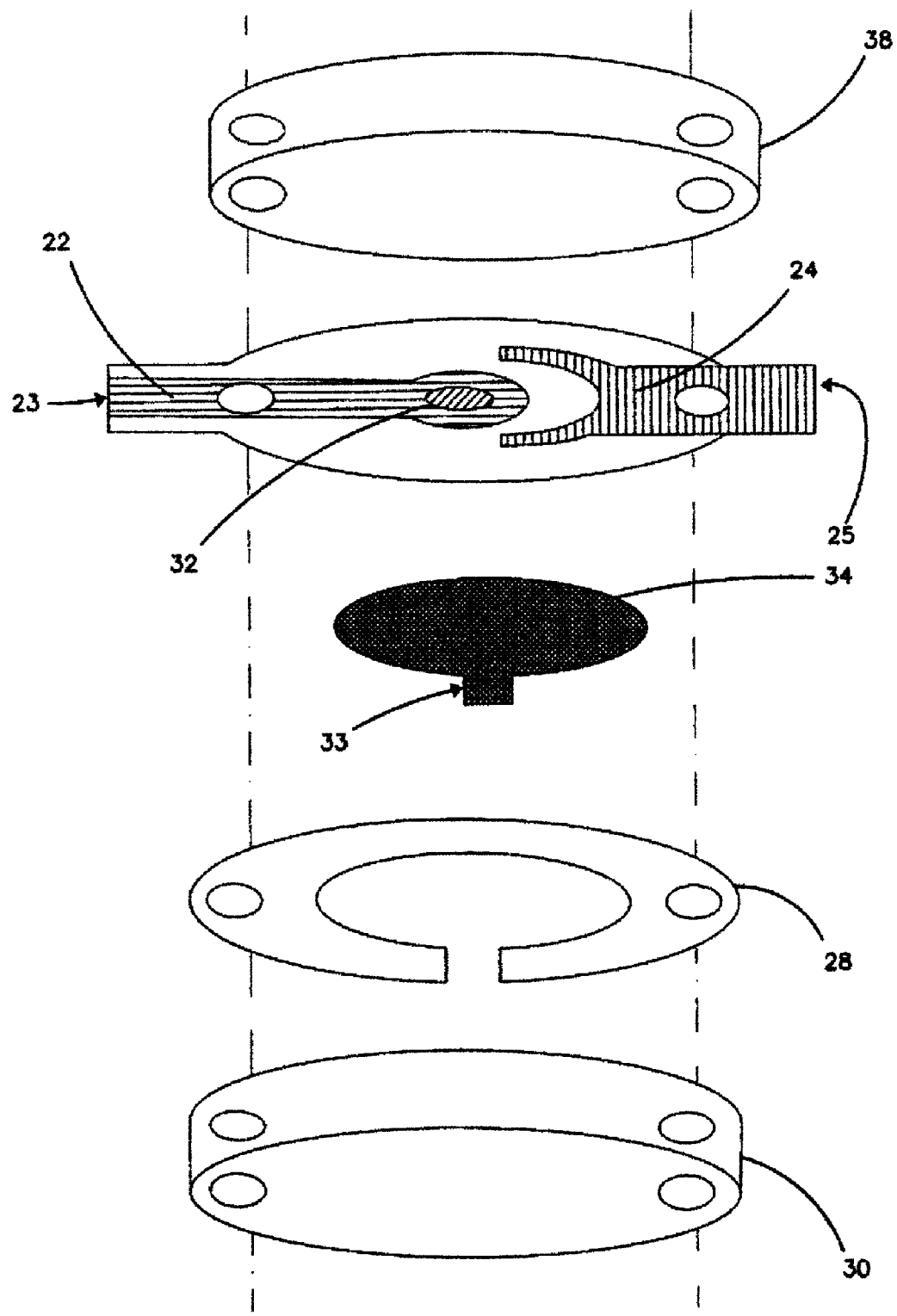
FIG. 2 is a schematic view of a second embodiment of an electrochemical sensor in accordance with the principles of the present invention having a working electrode and a counter electrode in a coplanar configuration.

In another embodiment of the invention, the two electrodes 22, 24 are coplanar as shown in FIG. 2. In this case, the sample chamber 26 is in contact with both electrodes and is bounded on the side opposite the electrodes by a non-conducting inert base 30. Suitable materials for the inert base include non-conducting materials such as polyester.

Other configurations of the inventive sensors are also possible. For example, the two electrodes may be formed on surfaces that make an angle to each other. One such configuration would have the electrodes on surfaces that form a right angle. Another possible configuration has the electrodes on a curved surface such as the interior of a tube. The working and counter electrodes may be arranged so that they face each other from opposite sides of the tube. This is another example of a facing electrode pair. Alternatively, the electrodes may be placed near each other on the tube wall (e.g., one on top of the other or side-by-side).

In any configuration, the two electrodes must be configured so that they do not make direct electrical contact with each other, to prevent shorting of the electrochemical sensor. This may be difficult to avoid when the facing electrodes are separated, over the average, by no more than about 100 μm.

A spacer 28 can be used to keep the electrodes apart when the electrodes face each other as depicted in FIGS. 1 and 3. The spacer is typically constructed from an inert non-conducting material such as pressure-sensitive adhesive, polyester, Mylar™, Kevlar™ or any other strong, thin polymer film, or, alternatively, a thin polymer film such as a Teflon™ film, chosen for its chemical inertness. In addition to preventing contact between the electrodes, the spacer 28 often functions as a portion of the boundary for the sample chamber 26 as shown in FIGS. 1-4. Other spacers include layers of adhesive and double-sided adhesive tape (e.g., a carrier film with adhesive on opposing sides of the film).

Sample Chamber

The sample chamber 26 is typically defined by a combination of the electrodes 22, 24, an inert base 30, and a spacer 28 as shown in FIGS. 1-4. A measurement zone is contained within this sample chamber and is the region of the sample chamber that contains only that portion of the sample that is interrogated during the analyte assay. In the embodiment of the invention illustrated in FIGS. 1 and 2, sample chamber 26 is the space between the two electrodes 22, 24 and/or the inert base 30. In this embodiment, the sample chamber has a volume that is preferably no more than about 1 μL, more preferably no more than about 0.5 μL, and most preferably no more than about 0.25 μL. In the embodiment of the invention depicted in FIGS. 1 and 2, the measurement zone has a volume that is approximately equal to the volume of the sample chamber. In a preferred embodiment the measurement zone includes 80% of the sample chamber, 90% in a more preferred embodiment, and about 100% in a most preferred embodiment.

Figure 5:
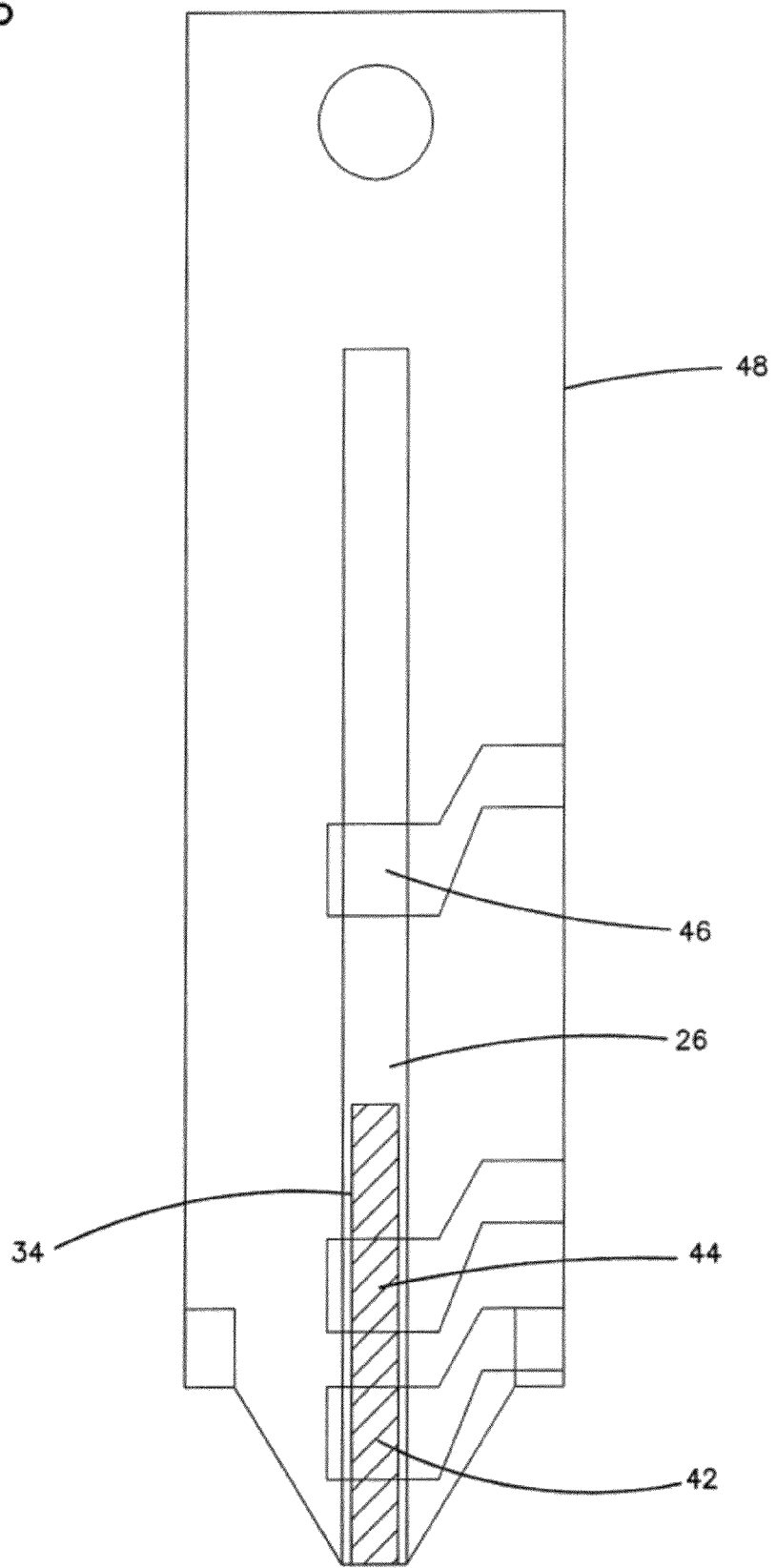
FIG. 5 is a top view of a fourth embodiment of an electrochemical sensor in accordance with the principles of the present invention, this sensor includes multiple working electrodes.

In another embodiment of the invention, shown in FIG. 3, sample chamber 26 includes much more space than the region proximate electrodes 22, 24. This configuration makes it possible to provide multiple electrodes in contact with one or more sample chambers, as shown in FIG. 5. In this embodiment, sample chamber 26 is preferably sized to contain a volume of no more than about 1 μL, more preferably no more than about 0.5 μL, and most preferably no more than about 0.25 μL. The measurement zone (i.e., the region containing the volume of sample to be interrogated) is generally sized to contain a volume of sample of no more than about 1 μL, preferably no more than about 0.5 μL, more preferably no more than about 0.25 μL, and most preferably no more than about 0.1 μL. One particularly useful configuration of this embodiment positions working electrode 22 and counter electrode 24 facing each other, as shown in FIG. 3. In this embodiment, the measurement zone, corresponding to the region containing the portion of the sample which will be interrogated, is the portion of sample chamber 26 bounded by the working surface of the working electrode and disposed between the two facing electrodes.

In both of the embodiments discussed above, the thickness of the sample chamber and of the measurement zone correspond typically to the thickness of spacer 28 (e.g., the distance between the electrodes in FIGS. 1 and 3, or the distance between the electrodes and the inert base in FIG. 2). The spacer may be, for example, an adhesive or double-sided adhesive tape or film. Preferably, this thickness is small to promote rapid electrolysis of the analyte, as more of the sample will be in contact with the electrode surface for a given sample volume. In addition, a thin sample chamber helps to reduce errors from diffusion of analyte into the measurement zone from other portions of the sample chamber during the analyte assay, because diffusion time is long relative to the measurement time. Typically, the thickness of the sample chamber is no more than about 0.2 mm. Preferably, the thickness of the sample chamber is no more than about 0.1 mm and, more preferably, the thickness of the sample chamber is about 0.05 mm or less.

Figure 12A:
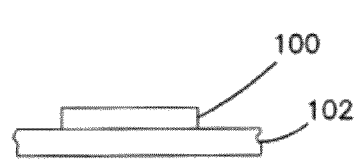
FIGS. 12A and 12B are cross-sectional views of one embodiment of an electrode pair formed using a recess of a base material, according to the invention.
Figure 12B:
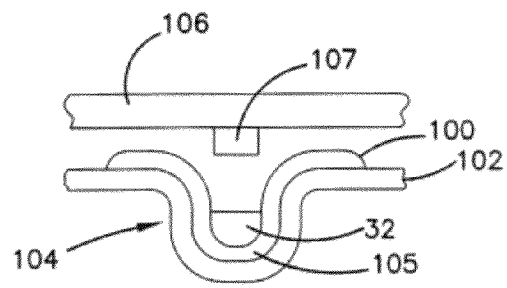

The sample chamber may be formed by other methods. Exemplary methods include embossing, indenting, or otherwise forming a recess in a substrate within which either the working electrode 22 or counter electrode 24 is formed. FIGS. 12A and 12B illustrate one embodiment of this structure. First, a conducting layer 100 is formed on an inert non-conducting base material 102. As described above, the conducting layer 100 can include gold, carbon, platinum, ruthenium dioxide, palladium, or other non-corroding materials. The inert non-conducting base material 102 can be made using a polyester, other polymers, or other non-conducting, deformable materials. A recess 104 is then formed in a region of the non-conducting base material 102 so that at least a portion of the conducting layer 100 is included in the recess 104. The recess 104 may be formed using a variety of techniques including indenting, deforming, or otherwise pushing in the base material 102. One additional exemplary method for forming the recess includes embossing the base material 102. For example, the base material 102 may be brought into contact with an embossing roll or stamp having raised portions, such as punch members or channels, to form the recess 104. In some embodiments, the base material 102 may be heated to soften the material.

The recess 104 may be circular, oval, rectangular, or any other regular or irregular shape. Alternatively, the recess 104 may be formed as a channel which extends along a portion of the base material 102. The conducting layer 100 may extend along the entire channel or only a portion of the channel. The measurement zone may be restricted to a particular region within the channel by, for example, depositing the sensing layer 32 on only that portion of the conducting layer 100 within the particular region of the channel. Alternatively, the measurement zone may be defined by placing a second electrode 107 over only the desired region of the first electrode 105.

At least a portion, and in some cases, all, of the conducting layer 100 is situated in the recess 104. This portion of the conducting layer 100 may act as a first electrode 105 (a counter electrode or a working electrode). If the conducting layer 100 forms the working electrode, then a sensing layer 32 may be formed over a portion of the conducting layer 100 by depositing a non-leachable redox mediator and/or second electron transfer agent in the recess 104, as shown in FIG. 12B. If a diffusible redox mediator or second electron transfer agent is used, then the diffusible material may be disposed on any surface in the sample chamber or in the sample.

A second electrode 107 is then formed by depositing a second conducting layer on a second base material 106. This second electrode 107 is then positioned over the first electrode 105 in a facing arrangement. Although not illustrated, if the redox mediator is non-leachable it will be understood that if the first electrode 105 were to function as a counter electrode, then the sensing layer 32 would be deposited on the second electrode 107 which would then function as the working electrode. If the redox mediator is diffusible, however, the redox mediator may be disposed on any surface of the sample chamber or may be placed in the sample.

In one embodiment, the second base material 106 rests on a portion of the first base material 102 and/or the conducting layer 100 which is not depressed, so that the second electrode 107 extends into the recess. In another embodiment, there is a spacer (not shown) between the first and second base materials 102, 106. In this embodiment, the second electrode 107 may or may not extend into the recess. In any case, the first and second electrodes 105, 107 do not make contact, otherwise the two electrodes would be shorted.

The depth of the recess 104 and the volume of the conductive layer 100, sensing layer 32, and the portion, if any, of the second electrode 107 in the recess 104 determines the volume of the measurement zone. Thus, the predictability of the volume of the measurement zone relies on the extent to which the formation of the recess 104 is uniform.

Figure 14A:
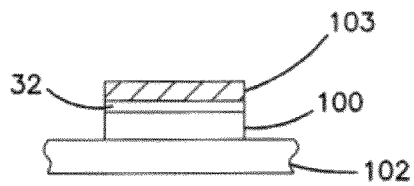
FIGS. 14A and 14B are cross-sectional views of a further embodiment of an electrode pair of the present invention formed using a recess of a base material and a sorbent material.
Figure 14B:
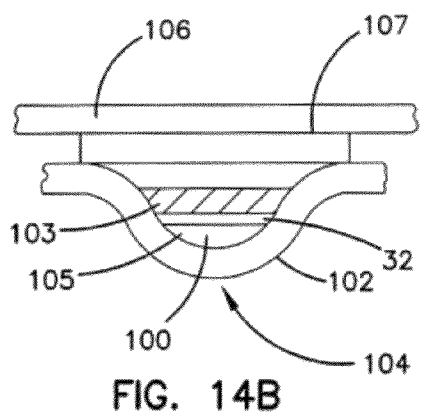

In addition to the conducting layer 100, a sorbent layer 103, described in detail below, may be deposited on the base material 102 prior to forming the recess 104, as shown in FIG. 14A. The sorbent material 103 may be indented, embossed, or otherwise deformed with the conducting layer 100 and base material 102, as shown in FIG. 14B. Alternatively, the sorbent material 103 may be deposited after the conducting layer 100 and base material 102 are indented, embossed, or otherwise deformed to make the recess 104.

Figure 13A:
FIGS. 13A and 13B are cross-sectional views of yet another embodiment of an electrode pair of the present invention formed in a recess of a base material.
Figure 13B:
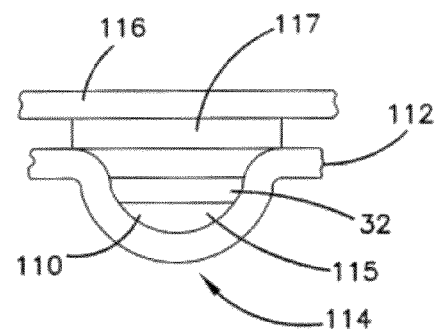

In another exemplary method for forming the analyte sensor, a recess 114 is formed in a first base material 112, as shown in FIGS. 13A and 13B. The recess may be formed by indenting, embossing, etching (e.g., using photolithographic methods or laser removal of a portion of the base material), or otherwise deforming or removing a portion of the base material 112. Then a first conducting layer 110 is formed in the recess 114. Any of the conductive materials discussed above may be used. A preferred material is a conductive ink, such as a conductive carbon ink available, for example, from Ercon, Inc. (Wareham, Mass.). The conductive ink typically contains metal or carbon dissolved or dispersed in a solvent or dispersant. When the solvent or dispersant is removed, the metal or carbon forms a conductive layer 110 that can then be used as a first electrode 115. A second electrode 117 can be formed on a second base material 116 and positioned over the recess 114, as described above. In embodiments having a non-leachable redox mediator, a sensing layer 32 is formed on the first electrode 115 to form a working electrode, as shown in FIG. 13B. In other embodiments having a non-leachable redox mediator, the sensing layer 32 may be formed on the second electrode 117 to form a working electrode. Alternatively, if a diffusible redox mediator is used, then the working electrode need not include the sensing layer disposed thereon. In fact, no sensing layer is required because the redox mediator may be placed in the sample and likewise for a diffusible second electron transfer agent, if one is present. Any diffusible components may be independently disposed on any surface of the sample chamber or placed in the sample. Furthermore, a sorbent material (not shown) may be formed within the recess, for example, on the first electrode 115.

A binder, such as a polyurethane resin, cellulose derivative, elastomer (e.g., silicones, polymeric dienes, or acrylonitrile-butadiene-styrene (ABS) resins), highly fluorinated polymer, or the like, may also be included in the conductive ink. Curing the binder may increase the conductivity of the conductive layer 110, however, curing is not necessary. The method of curing the binder may depend on the nature of the particular binder that is used. Some binders are cured by heat and/or ultraviolet light.

These structures allow for the formation of electrochemical sensors in which the volume of the measurement zone depends, at least in part, on the accuracy and reproducibility of the recess 104. Embossing, laser etching, photolithographic etching and other methods can be used to make reproducible recesses 104, even on the scale of 200 μm or less.

Sorbent Material

The sample chamber may be empty before the sample is placed in the chamber. Alternatively, the sample chamber may include a sorbent material 34 to sorb and hold a fluid sample during the measurement process. Suitable sorbent materials include polyester, nylon, cellulose, and cellulose derivatives such as nitrocellulose. The sorbent material facilitates the uptake of small volume samples by a wicking action which may complement or, preferably, replace any capillary action of the sample chamber. In addition or alternatively, a portion or the entirety of the wall of the sample chamber may be covered by a surfactant, such as, for example, Zonyl FSO.

In some embodiments, the sorbent material is deposited using a liquid or slurry in which the sorbent material is dissolved or dispersed. The solvent or dispersant in the liquid or slurry may then be driven off by heating or evaporation processes. Suitable sorbent materials include, for example, cellulose or nylon powders dissolved or dispersed in a suitable solvent or dispersant, such as water. The particular solvent or dispersant should also be compatible with the material of the working electrode 22 (e.g., the solvent or dispersant should not dissolve the electrode).

One of the most important functions of the sorbent material is to reduce the volume of fluid needed to fill the sample chamber and corresponding measurement zone of the sensor. The actual volume of sample within the measurement zone is partially determined by the amount of void space within the sorbent material. Typically, suitable sorbents consist of about 5% to about 50% void space. Preferably, the sorbent material consists of about 10% to about 25% void space.

The displacement of fluid by the sorbent material is advantageous. By addition of a sorbent, less sample is needed to fill sample chamber 26. This reduces the volume of sample that is required to obtain a measurement and also reduces the time required to electrolyze the sample.

The sorbent material 34 may include a tab 33 which is made of the same material as the sorbent and which extends from the sensor, or from an opening in the sensor, so that a sample may be brought into contact with tab 33, sorbed by the tab, and conveyed into the sample chamber 26 by the wicking action of the sorbent material 34.

This provides a preferred method for directing the sample into the sample chamber 26. For example, the sensor may be brought into contact with a region of an animal (including human) that has been pierced with a lancet to draw blood. The blood is brought in contact with tab 33 and drawn into sample chamber 26 by the wicking action of the sorbent 34. The direct transfer of the sample to the sensor is especially important when the sample is very small, such as when the lancet is used to pierce a portion of the animal that is not heavily supplied with near-surface capillary vessels and furnishes a blood sample volume of 1 μL or less.

Methods other than the wicking action of a sorbent may be used to transport the sample into the sample chamber or measurement zone. Examples of such methods for transport include the application of pressure on a sample to push it into the sample chamber, the creation of a vacuum by a pump or other vacuum-producing method in the sample chamber to pull the sample into the chamber, capillary action due to interfacial tension of the sample with the walls of a thin sample chamber, as well as the wicking action of a sorbent material.

The sensor can also be used in conjunction with a flowing sample stream. In this configuration, the sample stream is made to flow through a sample chamber. The flow is stopped periodically and the concentration of the analyte is determined by an electrochemical method, such as coulometry. After the measurement, the flow is resumed, thereby removing the sample from the sensor. Alternatively, sample may flow through the chamber at a very slow rate, such that all of the analyte is electrolyzed in transit, yielding a current dependent only upon analyte concentration and flow rate.

Other filler materials may be used to fill the measurement zone and reduce the sample volume. For example, glass beads can be deposited in the measurement zone to occupy space. Preferably, these filler materials are hydrophilic so that the body fluid can easily flow into the measurement zone. In some cases, such as glass beads with a high surface area, these filler materials may also wick the body fluid into the measurement zone due to their high surface area and hydrophilicity.

The entire sensor assembly is held firmly together to ensure that the sample remains in contact with the electrodes and that the sample chamber and measurement zone maintain the same volume. This is an important consideration in the coulometric analysis of a sample, where measurement of a defined sample volume is needed. One method of holding the sensor together is depicted in FIGS. 1 and 2. Two plates 38 are provided at opposite ends of the sensor. These plates are typically constructed of non-conducting materials such as plastics. The plates are designed so that they can be held together with the sensor between the two plates. Suitable holding devices include adhesives, clamps, nuts and bolts, screws, and the like.

Alternative Sensor Designs

Figure 18A:
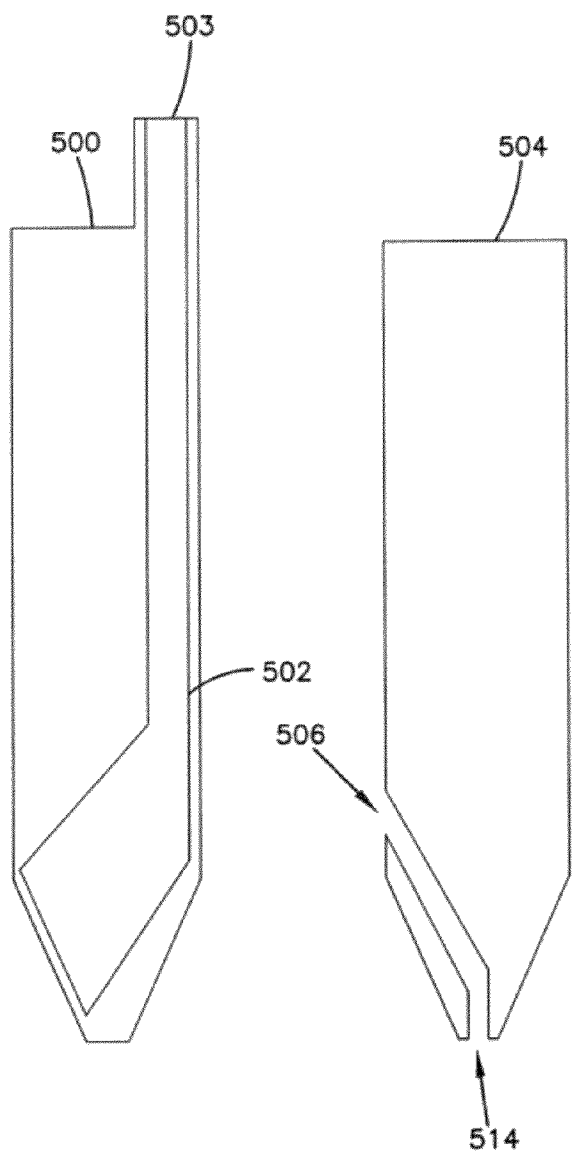
FIG. 18A illustrates a top view of a first film with a working electrode for use in a fifth embodiment of a sensor according to the invention.
Figure 18B:
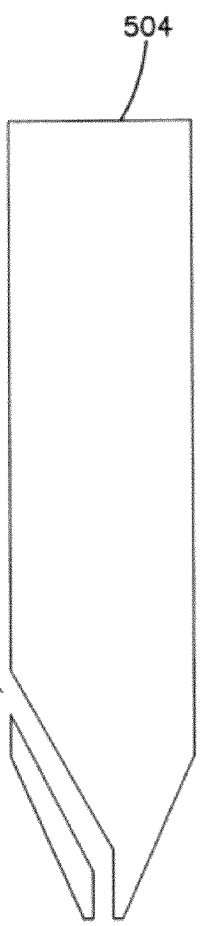
FIG. 18B illustrates a top view of a spacer for placement on the first film of FIG. 18A.
Figure 18C:
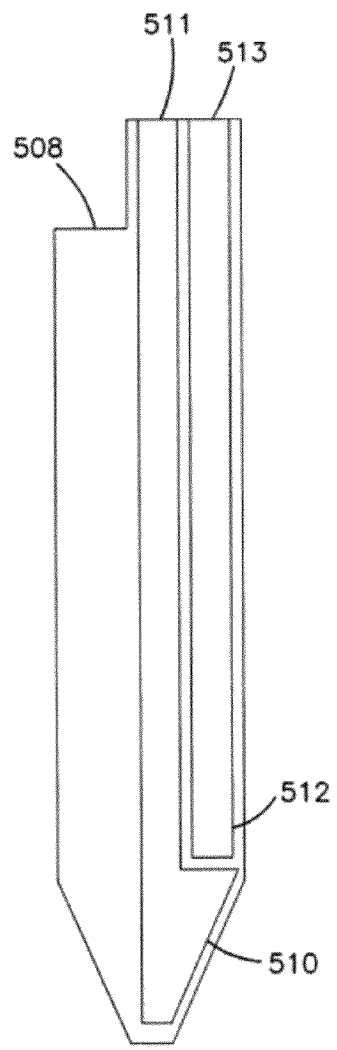
FIG. 18C illustrates a bottom view of a second film (inverted with respect to FIGS. 18A and 18B) with counter electrodes placement over the spacer of FIG. 18B and first film of FIG. 18A.

FIGS. 18A to 18C illustrate one alternative sensor design for formation of thin film sensors. The sensor includes a first substrate 500 upon which a working electrode 502 is formed. The working electrode 502 includes a contact region 503 for connection with external electronics. A spacer 504 (FIG. 18B), such as, for example, a layer of adhesive or a double-sided tape defines a channel 506 to produce a sample chamber for the sensor. Two counter (or counter/reference) electrodes 510, 512 are formed on a second substrate 508, as shown in FIG. 18C (inverted with respect to FIGS. 18A and 18B to show the electrode side up). This multiple counter electrode arrangement may provide a fill indicator function, as described below. Each counter electrode 510, 512 has a contact region 511, 513 for connection with external electronics. The second substrate 508 is inverted and placed over the first substrate 500, with the spacer 504 between, so that the working electrode 502 and the two counter electrodes 510, 512 are facing in the region of the channel 506.

In some instances, the counter electrode 510 nearest an entrance 514 of the channel 506 has a surface area within the sample chamber that is at least two times larger than the other counter electrode 512, and may be at least five or ten times larger. The non-leachable or diffusible redox mediator and/or second electron transfer agent can be provided on either the first or second substrates 500, 508 in a region corresponding to the channel 506, as described above.

The working electrode and counter electrodes can be formed to cover the entire channel region (except for a small space between the two counter electrodes). In this embodiment, the sample chamber and measurement zone are effectively the same and have the same volume. In other embodiments, the measurement zone has, for example, 80% or 90% of the volume of the sample chamber. It will be understood that similar sensors could be made using one counter electrode or three or more counter electrodes. It will also be understood that multiple working electrodes may also be provided on the sensor.

Figure 31A:
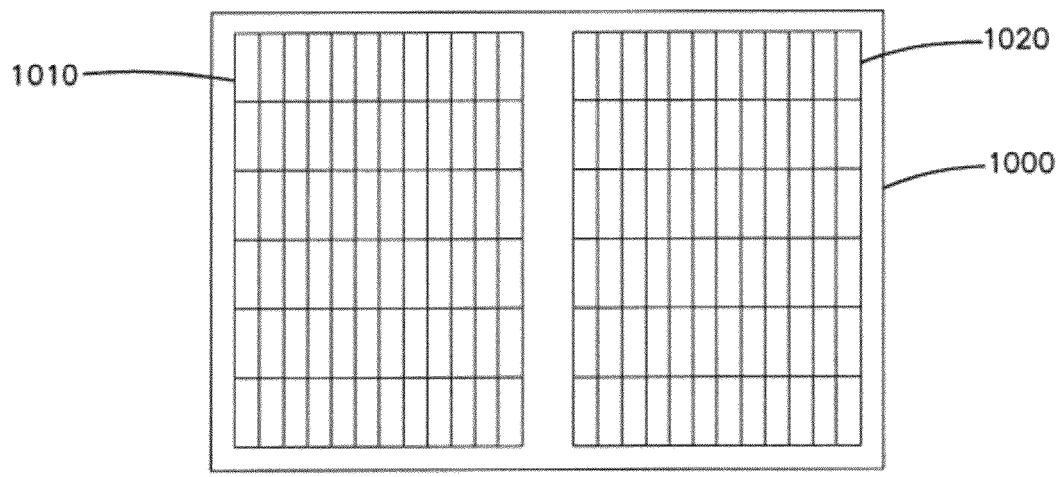
FIG. 31A illustrates a top view of one embodiment of a sheet of sensor components, according to the invention.
Figure 31B:
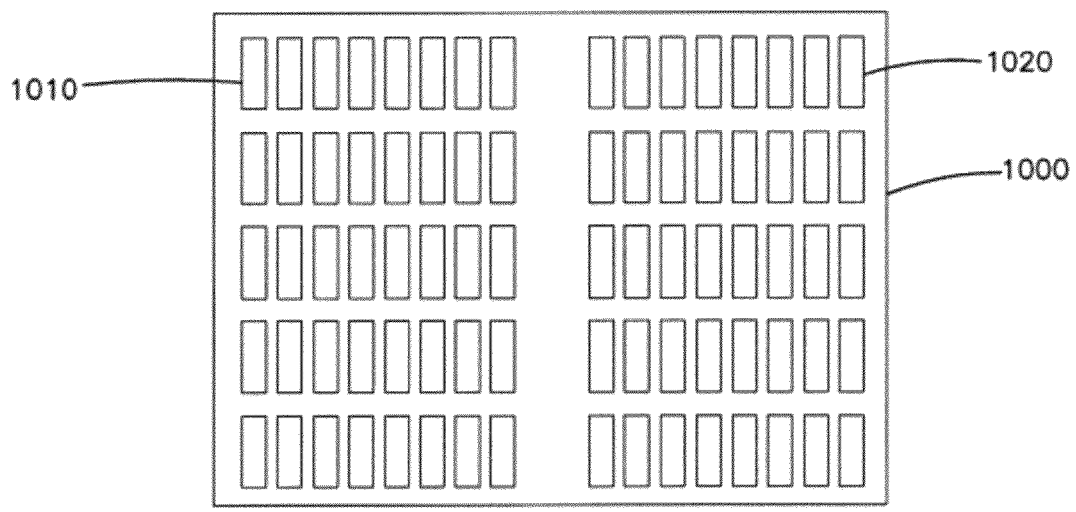
FIG. 31B illustrates a top view of another embodiment of a sheet of sensor components, according to the invention.

One example of a method for making the thin film sensors is described with respect to the sensor arrangement displayed in FIGS. 18A to 18C and can be used to make a variety of other sensor arrangements, including those described before. A substrate, such as a plastic substrate, is provided. The substrate can be an individual sheet or a continuous roll on a web. This substrate can be used to make a single sensor or to make multiple sensors. The multiple sensors can be formed on a substrate 1000 as working electrodes 1010 and counter electrode(s) 1020. In some embodiments, the substrate can be scored and folded to bring the working electrodes 1010 and counter electrodes 1020 together to form the sensor. In some embodiments, as illustrated in FIG. 31A, the individual working electrodes 1010 (and, in a separate section, the counter electrode(s) 1020) can be formed next to each other on the substrate 1000, to reduce waste material, as illustrated in FIG. 31A. In other embodiments, the individual working electrodes 1010 (and, in a separate section, the counter electrode(s) 1020) can be spaced apart, as illustrated in FIG. 31B. The remainder of the process is described for the manufacture of multiple sensors, but can be readily modified to form individual sensors.

Carbon or other electrode material (e.g., metal, such as gold or platinum) is formed on the substrate to provide a working electrode for each sensor. The carbon or other electrode material can be deposited by a variety of methods including printing a carbon or metal ink, vapor deposition, and other methods.

Optionally, a non-conductive material, such as a non-conductive ink, can be formed adjacent the working electrode to provide a planar surface along the path of travel of the sample fluid. The non-conductive material is suitable for creating a smooth surface to facilitate filling by capillary action and/or for reducing the likelihood that air bubbles will become entrapped near the working electrode. This non-conductive material can be colored or colorless and may be formed on the substrate by printing or other techniques. The non-conductive material may be deposited prior to or subsequent to the formation of the working electrode.

The counter electrode or counter electrodes are formed on the substrate. The counter electrode(s) are formed by depositing carbon or other electrode material onto the substrate. In one embodiment, the material of the counter electrode(s) is a Ag/AgCl ink. The material of the counter electrode(s) may be deposited by a variety of methods including printing or vapor deposition. In some embodiments, the counter electrodes are formed using different materials and/or one electrode is a counter or counter/reference electrode and the other electrode is a reference or counter/reference electrode. In one embodiment, the working electrodes are formed on a first half of a polymer sheet or web and the counter electrodes are formed on a second half of the polymer sheet or web so that the sheet or web can be folded to superimpose the working and counter electrodes in a facing arrangement.

A second non-conductive material may be deposited adjacent and/or between the counter electrode(s) to provide a planar surface along the path of travel of the sample fluid. This may be particularly desirable in the region between the counter electrodes that will be part of the sample chamber to planarize the surface of the sample chamber. The non-conductive material is suitable for creating a smooth surface to faciliate filling by capillary action and/or for reducing the likelihood that air bubbles will become entrapped between or near the counter electrode(s). This non-conductive material can be colored or colorless and may be formed on the by printing or other techniques. The non-conductive material may be deposited prior to or subsequent to the formation of the counter electrode(s).

An adhesive spacer is formed over at least one of the substrate/working electrode and substrate/counter electrode(s). The adhesive spacer may be a single layer of adhesive or a double-sided adhesive tape (e.g., a polymer carrier film with adhesive disposed on opposing surfaces). To form the channel, the spacer, optionally provided with one or more release liners, may be cut (e.g., die-cut) to remove the portion of the adhesive corresponding to the channel prior to disposing the spacer on the substrate. Alternatively, the adhesive may be printed or otherwise disposed on the substrate according to a pattern which defines the channel region. The thickness of the spacer typically determines the spacing between the working and counter electrodes. When the uniformity of this spacing among sensors is necessary (e.g., for coulometric measurements), uniformity in the thickness of the spacer is important. Preferably, the thickness does not vary more than ±5% over the individual sensor and/or among individual sensors in a batch.

The non-leachable or diffusible redox mediator and/or second electron transfer agent are disposed onto the substrate in at least the sample chamber region. If either or both of these components is non-leachable, that component or components must be disposed on the working electrode. If either or both of these components is diffusible, that component or components can be disposed on any surface of the substrate in the channel region. The redox mediator and/or second electrode transfer agent can be disposed independently or together on the substrate prior to or after disposition of the spacer. The redox mediator and/or second electrode transfer agent may be disposed by a variety of methods including, for example, screen printing, ink jet printing, spraying, painting, striping along a row or column of aligned and/or adjacent electrodes, and the like. Other components may be deposited separately or with the redox mediator and/or second electrode transfer agent including, for example, surfactants, polymers, polymer films, preservatives, binders, buffers, and cross-linkers.

After disposing the spacer, redox mediator, and second electron transfer agent, the substrate can be folded to form the sensor. The faces of the substrate are joined by the adhesive of the spacer. After bringing the faces together, the sensor can be cut out using a variety of methods including, for example, die cutting, slitting, or otherwise cutting away the excess substrate material and separating the individual sensors. In some embodiments, a combination of methods may be used. For example, some features may be die cut, while the remainder of the sensor is cut by slitting. As another alternative, the sensor components (e.g., the components illustrated in FIGS. 18A and 18C) may first be cut out of the substrates and then brought together to form the sensor by adhesively joining the two components using the spacer adhesive.

Figure 19C:
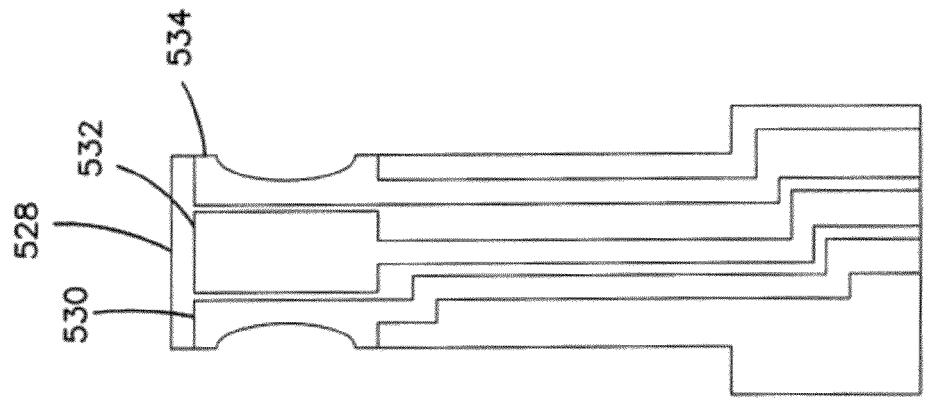
FIG. 19C illustrates a bottom view of a second film (inverted with respect to FIGS. 19A and 19B) with counter electrodes placement over the spacer of FIG. 19B and first film of FIG. 19A.
Figure 19B:
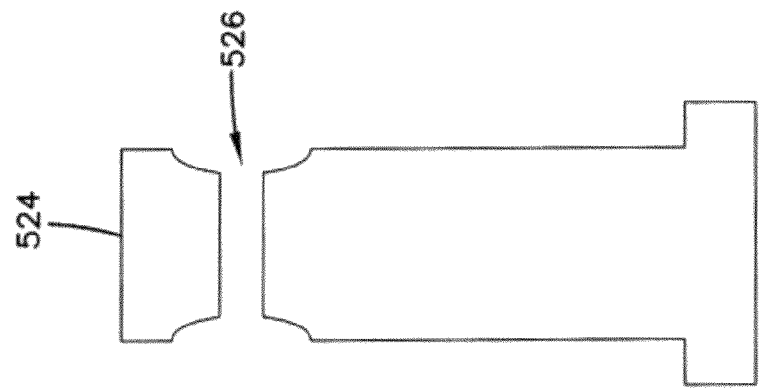
FIG. 19B illustrates a top view of a spacer for placement on the first film of FIG. 19A.
Figure 19A:
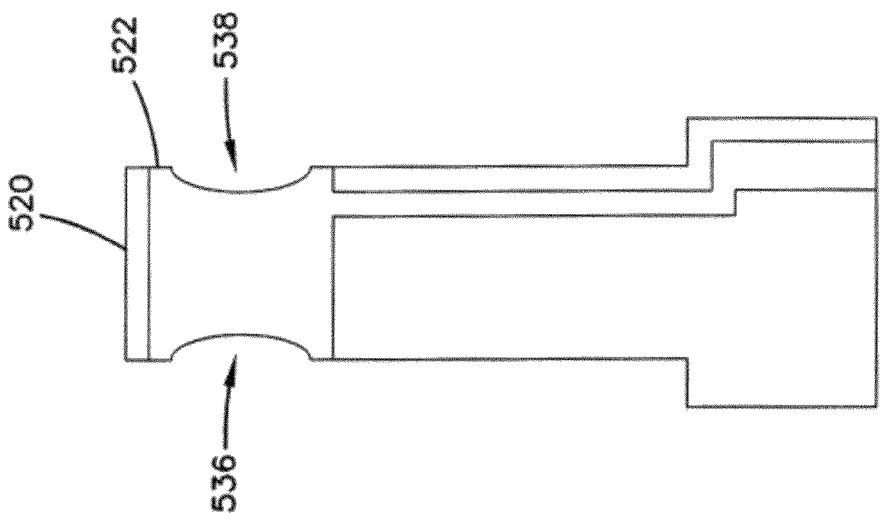
FIG. 19A illustrates a top view of a first film with a working electrode for use in a sixth embodiment of a sensor according to the invention.

The embodiment of a sensor illustrated in FIGS. 18A to 18C is an example of a tip-fill sensor. An alternative sensor construction is illustrated in FIGS. 19A to 19C. This is a side-fill sensor. FIG. 19A illustrates a first substrate 520 with a working electrode 522. FIG. 19B illustrates a spacer 524 defining a channel 526. FIG. 19C (inverted with respect to FIGS. 19A and 19B to illustrate the electrodes) illustrates a second substrate 528 with three counter (or counter/reference) electrodes 530, 532, 534.

This sensor can be manufactured as described above. The symmetric disposition of the counter electrodes allow the sensor to be filled from either the left or right side for convenience of left-handed and right-handed people. It will be understood, however, that similar sensor arrangements can be formed using one, two, or four or more counter electrode(s) and/or two or more working electrodes. The scalloped regions 536, 538 may be formed, for example, by die cutting and may, at least in some instances, be precisely controlled to provide a reproducible channel length. As an alternative arrangement, the sides of the sensor may be straight to allow the sensor to be cut out from the remainder of the substrate and/or from other sensors by slitting the substrate in parallel directions using, for example, a gang arbor blade system. As illustrated in FIGS. 19A, 19B, and 19C, the edges of the sensor can define edges of the sample chamber and/or measurement zone. By accurately controlling the distance between cuts, variability in sample chamber volume can often be reduced. In some instances, these cuts are preferably parallel to each other, as parallel cuts may be the easiest to make reproducibly.

FIGS. 20A, 20B, and 20C illustrate another example of a side-filling sensor arrangement. FIG. 20A illustrates a first substrate 540 with a working electrode 542. FIG. 20B illustrates a spacer 544 defining a channel 546. FIG. 20C (inverted with respect to FIGS. 20A and 20B) illustrates a second substrate 548 with three counter (or counter/reference) electrodes 550, 552, 554.

FIGS. 21A, 21B, and 21C illustrate another example of a tip-filling sensor arrangement. FIG. 21A illustrates a first substrate 560 with a working electrode 562. FIG. 21B illustrates a spacer 564 defining a channel 566. FIG. 21C (inverted with respect to FIGS. 21A and 21B) illustrates a second thin film substrate 568 with two counter (or counter/reference) electrodes 570, 572. A vent hole 574 (indicated as a shaded region in FIG. 21C) is provided through the second substrate. In the illustrated embodiment, this vent hole 574 is made through only the substrate 568 that carries the counter electrode(s) and, optionally, the spacer 564. In this embodiment, the vent hole may be formed by, for example, die cutting a portion of the substrate. This die cut may remove a portion of at least one counter electrode, but a sufficient amount of the counter electrode should remain for contact with the sample in the channel and for electrical connection to a contact at the other end of the sensor. In another embodiment, the vent hole 574 may be made through all of the layers or through the first substrate and not the second substrate.

Figure 22A:
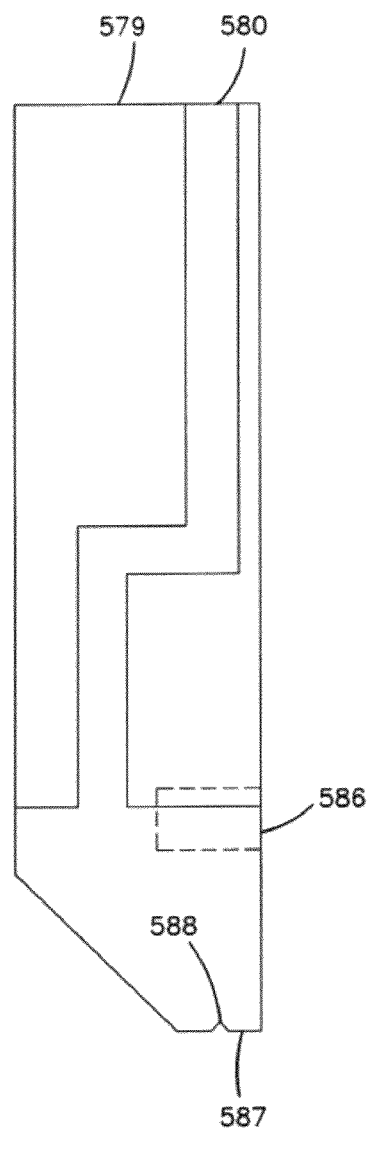
FIG. 22A illustrates a top view of a first film with a working electrode for use in a ninth embodiment of a sensor according to the invention.
Figure 22B:
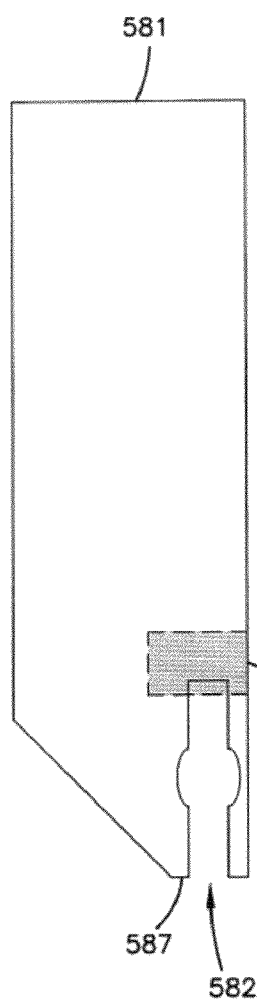
FIG. 22B illustrates a top view of a spacer for placement on the first film of FIG. 22A.
Figure 22C:
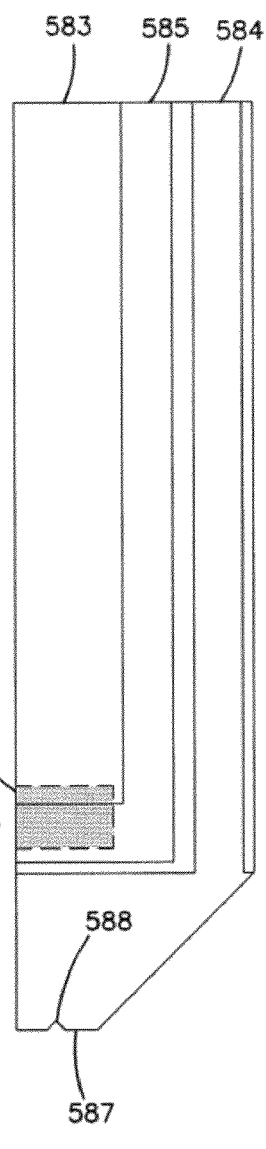
FIG. 22C illustrates a bottom view of a second film (inverted with respect to FIGS. 22A and 22B) with counter electrodes placement over the spacer of FIG. 22B and first film of FIG. 22A.

Another embodiment is illustrated in FIGS. 22A, 22B, and 22C, with a different shape. This sensor includes a first substrate 579 with at least one working electrode 580, as illustrated in FIG. 22A. The sensor also includes a spacer 581 with a channel 582 formed in the spacer 581, as shown in FIG. 22B. The sensor further includes a second substrate 583 with two counter electrodes 584, 585, as shown in FIG. 22C (inverted with respect to FIGS. 22A and 22B). A venting aperture 586 is cut typically through all of the layers and extends from a side of the sensor. In some embodiments, the venting aperture and the front portion 587 of the sensor are simultaneously cut with a reproducible distance between the venting aperture and the front portion 587 of the sensor to provide a reproducible length for the channel 582 and the working electrode 580. FIGS. 22A, 22B, and 22C also illustrate another feature that can be used with any sensor arrangement. An indentation 588 may be formed at the filling opening of the channel 582 to facilitate the drawing of fluid into the sensor. In this configuration, the fluid is not provided with a flat face, but rather an indented face that may aid in wicking or capillary filling of the channel (i.e., sample chamber). This configuration may also reduce the likelihood that the user of the sensor will block the channel during collection of the sample. A flat faced sensor might be blocked by pressing the tip of the sensor edgewise against the skin.

FIGS. 23A, 23B, and 23C illustrate another example of a side-filling sensor arrangement. FIG. 23A illustrates a first substrate 640 with a working electrode 642. FIG. 23B illustrates a spacer 644 defining a channel 646. FIG. 23C (inverted with respect to FIGS. 23A and 23B) illustrates a second substrate 648 with three counter (or counter/reference) electrodes 650, 652, 654. This sensor can be formed by making straight cuts of the substrates. The sensors can be made adjacent to one another, as illustrated in FIG. 31A, which may produce less waste material. The length of the channel 646 is typically defined by the two parallel cuts along the sides 656, 658 of the sensors. Another optional processing advantage, particularly if the sensor are formed adjacent to each other, is that the redox mediator and/or second electron transfer agent can be disposed in the channel by striping a continuous stream of these components along a row or column of adjacent sensors. This may result in better efficiency and less waste of the redox mediator and/or second electron transfer agent, as compared to other techniques, such as individually placing these components within the individual channels.

FIGS. 24A, 24B, and 24C illustrate another sensor configuration. This sensor includes a first substrate 600 with at least one working electrode 602, as illustrated in FIG. 24A. The sensor also includes a spacer 604 with a channel 606 formed in the spacer 604, as shown in FIG. 24B. The sensor further includes a second substrate 608 with two counter electrodes 610, 612, as shown in FIG. 24C (inverted with respect to FIGS. 24A and 24B). The sensor may also include, for example, an indicator, such as a slot 614 or an extension 616 from the body of the sensor that indicates to the user which side should be placed adjacent to the sample. This may be particularly important where the sensor reading is only correct when sample enters from a particular side.

FIG. 24B also illustrates another optional feature that may be used in any of the sensor configurations. In this illustration, the sample chamber 606 is not formed using straight lines, but there is an expanded region 618 within the sample chamber. This permits larger sample chambers without forming larger openings. This expanded region can be formed as any shape including circular, square, rectangular, and other regular and irregular shapes.

FIG. 25 is an example of an assembled sensor illustrating another alternative sensor arrangement for a side-fill sensor 620. This sensor includes extensions 622 from the sensor body 624 to indicate to a user where the openings for the sample chamber 626 are provided.

One optional feature is illustrated in FIG. 32 which is an edge-on view of the sensor from the inside of the meter. FIG. 32 illustrates a first substrate 1120 and a second substrate 1130 that extend into the meter from the remainder of the sensor 1100 (i.e., portion 1140 is recessed with respect to substrates 1120 and 1130 in FIG. 32). Examples of this configuration are illustrated in FIGS. 18A-18C and 24A-24C. Typically, the sensor 1100 is coupled to a meter 1110 that includes contact pads (not shown) that contact the contact regions (e.g., regions 503, 511, and 513 in FIGS. 18A and 18C) of the electrodes of the sensor 1100. The end of the sensor 1100 which contains the contact regions can be slid into the meter 1110. It is typically important that the contact pads of the meter 1110 make contact with the correct contact regions of the sensor so that the working electrode and counter electrode(s) are correctly coupled to the meter. In some instances, the sensor is configured so that the contact region for the working electrode on the first substrate 1120 has a different width, $w_1$, than width, $w_2$, for the contact region of the second substrate 1130 carrying the counter electrode(s). Examples of electrode configurations with this structure are provided in FIGS. 18A-18C and 24A-24C. To ensure proper insertion of the sensor 1100 into the meter 1110, the meter 1110 may include a raised area 1140 that prevents or hinders the insertion of the sensor in an improper direction. For example, the width, w2, of the contact region of the second substrate 1130 may be wider than the width, w1, of the contact region of the first substrate 1120, as illustrated in FIG. 32. In this instance, the raised area 1140 is positioned to allow sensor 1100 to be slid into the meter so that the first substrate 1120 is next to the surface 1150 from which the raised area 1140 protrudes, but would prevent or hinder having the second substrate 1130 next to the surface 1150 from which the raised area 1140 protrudes. Objects other than a raised area can also be used to guide the user in correct introduction of the sensor into the meter.

Integrated Sample Acquisition and Analyte Measurement Device

Many approaches are known in the art for acquiring and/or transporting a small sample from the body to a sensor. These include, for example, U.S. Pat. Nos. 5,746,217; 5,820,570; 5,857,983; and 5,879,311, incorporated herein by reference. Any of these sample acquisition and/or transporting methods may be employed with the sensor of the current invention.

Figure 6:
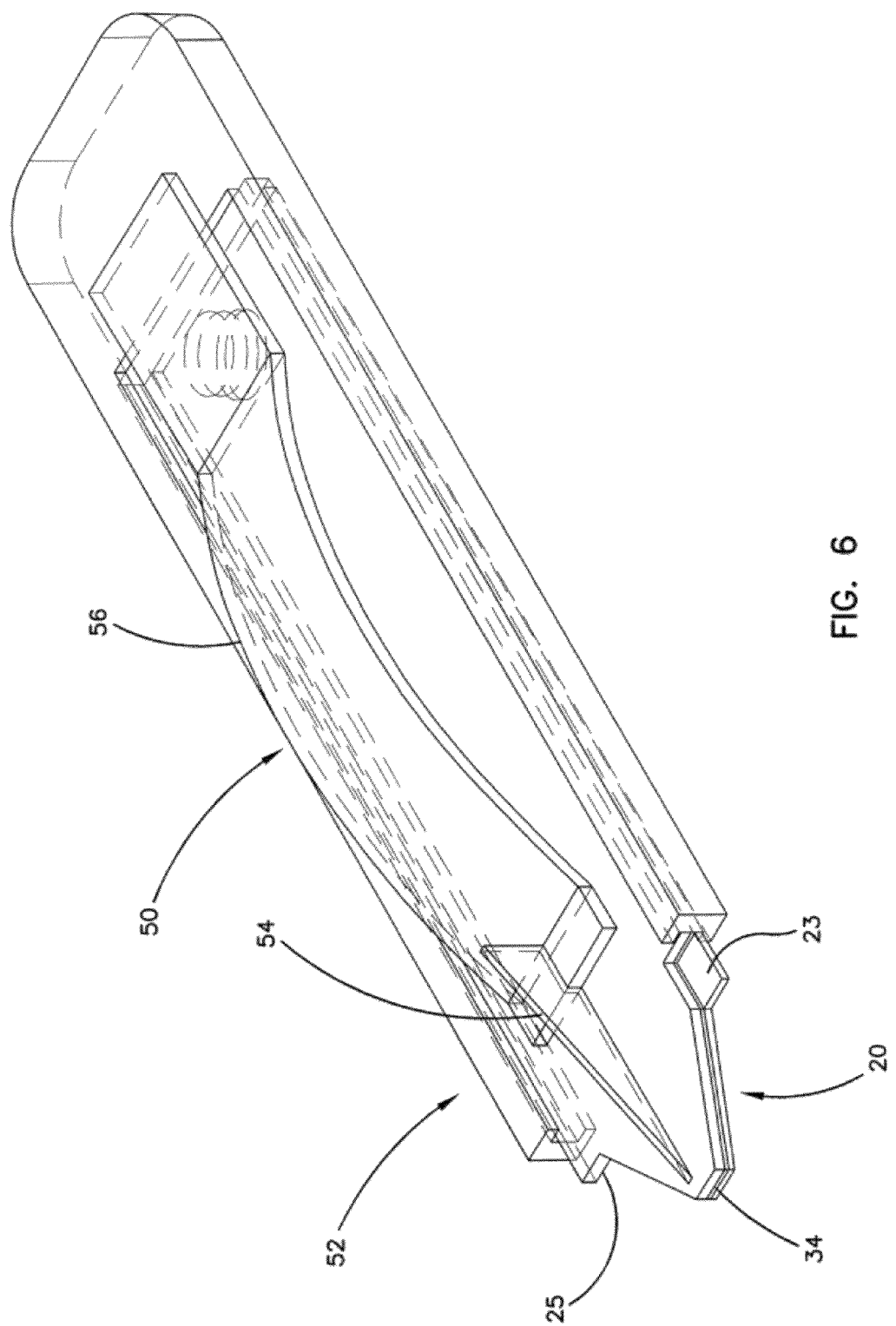
FIG. 6 is a perspective view of an embodiment of an analyte measurement device, in accordance with the principles of the present invention, having a sample acquisition means and the sensor of FIG. 4.

In a preferred embodiment of the invention, an analyte measurement device 52 constructed according to the principles of the present invention includes a sensor 20, as described hereinabove, combined with a sample acquisition apparatus 50 to provide an integrated sampling and measurement device. The sample acquisition apparatus 50 illustrated in FIG. 6, includes, for example, a skin piercing member 54, such as a lancet, attached to a resilient deflectable strip 56 (or other similar device, such as a spring) which may be pushed to inject the lancet into a patient's skin to cause blood flow.

The resilient strip 56 is then released and the skin piercing member 54 retracts. Blood flowing from the area of skin pierced by member 54 can then be transported, for example, by the wicking action of sorbent material 34, into sensor 20 for analysis of the analyte. The analyte measurement device 52 may then be placed in a reader, not shown, which connects a coulometer or other electrochemical analysis equipment to the electrode tabs 23, 25 to determine the concentration of the analyte by electroanalytical means. Preferably, the analyte measurement device is enclosed within the reader when connected to the coulometer or other electrochemical analysis equipment.

In a preferred embodiment, the integrated sample acquisition and analyte measurement device comprises a lancing instrument that holds a lancet and measurement strip. The lancing instrument preferably requires active cocking. By requiring the user to cock the device prior to use, the risk of inadvertently triggering the lancet is minimized.

Preferably, the lancing instrument is automatically triggered when the lancing instrument is pressed firmly against the skin with an adequate amount of pressure. As is already known in the art, a larger sample of body fluid such as blood or interstitial fluid is expressed when pressure is applied around a site where a hole has been created the skin. For example, see the above-mentioned U.S. patents to Integ and Amira as well as the tip design of the lancing instruments sold by Becton Dickenson. All of these lancing devices have a protruding ring that surrounds the lancing site to create pressure that forces sample out of the wound. However, all of these devices require the user to apply adequate pressure to the wound site to express the sample, and all of the lancing instruments are triggered by a button push by the user. Design of an appropriate pressure trigger is well-known to one skilled in the art.

Preferably, the lancing instrument will also permit the user to adjust the depth of penetration of the lancet into the skin. Such devices are already commercially available from companies such as Boehringer Mannheim and Palco. This feature allows users to adjust the lancing device for differences in skin thickness, skin durability, and pain sensitivity across different sites on the body and across different users.

In a more preferred embodiment, the lancing instrument and the test reader are integrated into a single device. To operate the device the user need only insert a disposable cartridge containing a measurement strip and lancing device into the integrated device, cock the lancing instrument, press it against the skin to activate it, and read the result of the measurement. Such an integrated lancing instrument and test reader simplifies the testing procedure for the user and minimizes the handling of body fluids.

FIG. 26 illustrates another example of an integrated sample acquisition and sensor device 700. The integrated sample acquisition and sensor device 700 includes a housing 702, a skin piercing member (e.g., a lancet) 704, a piercing/collecting aperture 706, an optionally removable sensor 708, a sensor guide 710, and a retraction mechanism 714 for the skin piercing member. This device 700 can be designed for reuse (e.g., by making the skin piercing member 704 and sensor 708 removable) or for single use.

The housing 702 may be formed of a variety of materials including metal and plastic. The housing 702 may include a hinge 716 or other configuration (e.g., adhesive or interlocking parts) for holding portions of the housing together.

The piercing/collecting aperture 706 is provided in the housing 702 to allow the skin piercing member 704 to extend through the aperture 706 and pierce the skin of a user, thereby causing blood (or other body fluid) flow. The sensor 708 also extends to the edge or out of the aperture 706 to collect the blood (or other body fluid) through an opening (not shown) in the tip of the sensor. This may allow the user to pierce the skin and collect the fluid sample without moving the device 700. Alternatively, separate apertures may be provided for the skin piercing member 704 and sensor 708. The sensor guide may be formed in the housing 702 or added to the housing to guide the sensor 708 into place if the sensor is inserted into and through the housing and/or to support the sensor within the housing and during sample collection.

The skin piercing member 704 may include an actuator (not shown) that includes a mechanism that allows for cocking and releasing the skin piercing member 704 or the skin piercing member may be actuated externally. For example, a sensor reader (not shown) or other device may be coupled to the sample acquisition and sensor device, the sensor reader or other device including a mechanism that cocks and/or releases the skin piercing member 704.

The retraction mechanism 714 of the device 700 may be, for example, a spring or resilient metal strip that retracts the skin piercing member 704 back into the housing after piercing the skin of the user. This may allow for unobstructed collection of the sample and/or prevent further piercing of the skin of the user or others to reduce or prevent contamination or infection caused by transfer of body fluids or other harmful agents. Alternatively, retraction of the skin piercing member may be accomplished using an external device or apparatus.

One example of operation includes cocking the skin piercing member 704 and then releasing the skin piercing member 704 so that it extends out of the housing 702 through the piercing/collecting aperture 706 and pierces the skin of the user. The skin piercing element 704 optionally pushes the sensor out of the way while extending out of the housing. The skin piercing element 704 is retracted back within the housing 702 using the retraction mechanism 714. Upon retraction of the skin piercing element, the sensor collects a sample fluid from the pierced skin through an opening in the sensor 708.

If a sensor reader is used, the sensor reader may also be configured to couple with a contact end of the sensor. The sensor reader may include a potentiostat or other component to provide a potential and/or current for the electrodes of the sensor. The sensor reader may also include a processor (e.g., a microprocessor or hardware) for determining analyte concentration from the sensor signals. The sensor reader may include a display or a port for coupling a display to the sensor. The display may display the sensor signals and/or results determined from the sensor signals including, for example, analyte concentration, rate of change of analyte concentration, and/or the exceeding of a threshold analyte concentration (indicating, for example, hypo- or hyperglycemia). This sensor reader may be used in conjunction with the integrated sample acquisition and sensor device or the sensor reader may be used with the sensor alone, the contacts of the sensor making connection with contacts in the sensor reader.

Operation of the Sensor

An electrochemical sensor of the invention may be operated with or without applying a potential. In one embodiment, the electrochemical reaction occurs spontaneously and a potential need not be applied between the working and counter electrodes.

In another embodiment, a potential is applied between the working and counter electrodes. Yet the potential does not need to remain constant. The magnitude of the required potential is dependent on the redox mediator. The potential at which the electrode poises itself, or where it is poised by applying an external bias, and where the analyte is electrolyzed is typically such that the electrochemical reaction is driven to or near completion, but it is, preferably, not oxidizing enough to result in significant electrochemical reaction of interferents; such as urate, ascorbate, and acetaminophen, that may affect the signal measured. For non-leachable redox mediators, the potential is typically between about −350 mV and about +400 mV versus the standard calomel electrode (SCE). Preferably, the potential of the redox mediator is more negative than +100 mV, more preferably the potential is more negative than 0 mV, and most preferably the potential is about −150 mV versus SCE.

When an external potential is applied, it may be applied either before or after the sample has been placed in the sample chamber. If the measurement zone comprises only a portion of the sample chamber then the potential is preferably applied after the sample has come to rest in the sample chamber to prevent electrolysis of sample passing through the measurement zone as the sample chamber is filling. Alternatively, in the case where the measurement zone comprises most or all of the sample chamber, the potential, optionally, may be applied before or during the filling of the sample chamber without affecting the accuracy of the assay. When the potential is applied and the sample is in the measurement zone, an electrical current will flow between the working electrode and the counter electrode. The current is a result, at least in part, of the electrolysis of the analyte in the sample. This electrochemical reaction occurs via the redox mediator and the optional second electron transfer agent. For many biomolecules, B, the process is described by the following reaction equations:

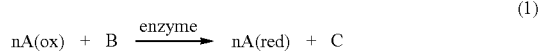

(1)

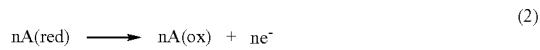

(2)

Biochemical B is oxidized to C by redox mediator species A in the presence of an appropriate enzyme. Then the redox mediator A is oxidized at the electrode. Electrons are collected by the electrode and the resulting current is measured. The measured current may also include a background current resulting in a measured background charge, due, at least in part, to the shuttling of a diffusible redox mediator between the working electrode and the counter electrode. This background current can be minimized or accounted for, as described above.

As an example, one sensor of the present invention is based on the reaction of a glucose molecule with two $[Os(dmo\text{-}phen)_2(NMI)Cl]^{2+}$ cations, where dmo-phen is 4,8-dimethoxy phenanthroline and NMI is N-methyl-imidazole, in the presence of glucose oxidase to produce two $[Os(dmo\text{-}phen)_2(NMI)Cl]^{+}$ cations, two protons, and an oxidation product of glucose, for example, gluconolactone or another ketone. The amount of glucose present is assayed by electrooxidizing the $[Os(dmo\text{-}phen)_2(NMI)Cl]^{+}$ cations to $[Os(dmo\text{-}phen)_2(NMI)Cl]^{2+}$ cations and measuring the total charge passed.

Those skilled in the art will recognize that there are many different reactions that will provide the same result; namely the electrolysis of an analyte through a reaction pathway incorporating a redox mediator. Equations (1) and (2) are a non-limiting example of such a reaction.

Coulometry

In a preferred embodiment of the invention, coulometry is used to determine the concentration of the analyte. This measurement technique utilizes current measurements obtained at intervals over the course of the assay, to determine analyte concentration. These current measurements are integrated over time to obtain the amount of charge, Q, passed to or from the electrode. Q is then used to calculate the concentration of the analyte ($C_A$) by the following equation (when the redox mediator is non-leachable):

$$C_A = Q/nFV \tag{3a}$$

where n is the number of electron equivalents required to electrolyze the analyte, F is Faraday's constant (approximately 96,500 coulombs per equivalent), and V is the volume of sample in the measurement zone. When using a diffusible mediator, the concentration of the analyte can be obtained from the following equation:

$$C_A + (Q_{tot} - Q_{back})/nFV \tag{3b}$$

where $Q_{tot}$ is the total charge transferred during the measurement and $Q_{back}$ is the amount of charge transferred that was not due to the analyte, e.g., charge transferred by the shuttling of the diffusible mediator between the working electrode and the counter electrode. In at least some instances, the sensor is constructed so that the background to charge is at most 5 times the size of the charge generated by electrolysis of an amount of analyte. Preferably, the background signal is at most 200%, 100%, 50%, 25%, 10%, or 5% of the charge generated by electrolysis of the analyte.

One example of a method for determining the ratio of background signal to signal generated by electrolysis of the analyte is described as follows for the facing electrode pairs. If the shuttling of the redox mediator is not disabled by the applied potential, the charge that results from the shuttling of the redox mediator may be represented by the following formula:

$$Q_{back} = (AFD_M C_M/d)(tm_M)$$

where A is the area of the working electrode; F is Faraday's constant (96,500 coulombs/equivalent); $D_M$ is the effective diffusion coefficient of the redox mediator; $C_M$ is the concentration of the redox mediator in the measurement zone; d is the distance separating facing electrodes; t is the amount of time for the measurement; and $n_M$ is the number of electrons gained or lost by the redox mediator.

Additionally, the charge of the analyte, for example, glucose, when the analyte is electrooxidized to about 90% completion in the measurement period may be represented by the following formula:

$$Q_G = Ad(0.90)C_G n_G F$$

where A is the area of the working electrode; d is the distance separating facing electrodes; $C_G$ is the concentration of glucose; n is the number of electrons needed to electrolyze the analyte (e.g., 2 electrons per glucose molecule); and F is Faraday's constant. When $C_G$ is 5 mM (or $5 \times 10^{-6}$ moles/cm$^3$), t is 60 seconds, $n_G$ is 2, and $n_M$ is 1, the ratio of charge from the redox mediator to the charge from electrooxidation of the analyte may be represented by the following formula:

$$Q_{Back}/Q_G = (D_M C_M/d^2)(tn_M/(0.9n_G C_G)) = (D_M C_M/d^2) \times (6.7 \times 10^6)$$

For example, if the ratio of $Q_{Back}/Q_G$ is 5, then $(D_M C_M)/d^2$ is $7.5 \times 10^{-7}$ moles/(cm$^3$ sec). Also for example, if the ratio of $Q_{Back}/Q_G$ is 1, then $(D_M C_M)/d^2$ is $1.5 \times 10^{-7}$ moles/(cm$^3$ sec). Still another example, if the ratio is 0.1, then $(D_M C_M)/d^2$ is $1.5 \times 10^{-8}$ moles/(cm$^3$ sec). Thus, depending on the ratio desired, a sensor may be configured to have the desired ratio by choosing $D_M$, $C_M$, and d accordingly. For example, the concentration of the redox mediator may be reduced (i.e., $C_M$ may be reduced). Alternatively, or additionally, the diffusion of the redox mediator may be reduced by, for example, having a barrier to the flow of the diffusible mediator to the counter electrode (i.e., reduce the effective diffusion coefficient of the redox mediator—$D_M$). Other sensor configurations are also suitable for controlling the ratio of background signal to signal generated by the analyte and will be described below.

The background charge, (back) can be accounted for in a variety of ways. $Q_{back}$ can be made small, for example, by using only limited amounts of diffusible redox mediator; by providing a membrane over the counter electrode that limits diffusion of the redox mediator to the counter electrode; or by having a relatively small potential difference between the working electrode and the counter electrode. Other examples of sensor configurations and methods suitable for reducing $Q_{back}$ include those already described such as sensors having a redox mediator reaction rate at the working electrode that is significantly faster than that at the counter electrode; immobilizing the redox mediator on the working electrode; having the redox mediator become immobilized on the counter or counter/reference electrode upon its reaction at the counter or counter/reference electrode; or slowing the diffusion of the redox mediator.

Alternatively, the sensor may be calibrated individually or by batch to determine a calibration curve or a value for $Q_{back}$. Another option is to include a second electrode pair that is missing an item necessary for electrolysis of the analyte, such as, for example, the second electron transfer agent, so that the entire signal from this second electrode pair corresponds to $Q_{back}$.

For coulometric measurements, at least 20% of the analyte is electrolyzed. Preferably at least 50%, more preferably at least 80%, and even more preferably at least 90% of the analyte is electrolyzed. In one embodiment of the invention, the analyte is completely or nearly completely electrolyzed. The charge can then be calculated from current measurements made during the electrochemical reaction, and the concentration of the analyte is determined using equation (3a) or (3b).

The completion of the electrochemical reaction is typically signaled when the current reaches a steady-state value. This indicates that all or nearly all of the analyte has been electrolyzed. For this type of measurement, at least 90% of the analyte is typically electrolyzed, preferably, at least 95% of the analyte is electrolyzed and, more preferably, at least 99% of the analyte is electrolyzed.

For coulometry, it is typically desirable that the analyte be electrolyzed quickly. The speed of the electrochemical reaction depends on several factors, including the potential that is applied between the electrodes and the kinetics of reactions (1) and (2). (Other significant factors include the size of the measurement zone and the presence of sorbent in the measurement zone.) In general, the larger the potential, the larger the current through the cell (up to a transport limited maximum) and therefore, the faster the reaction will typically occur. However, if the potential is too large, other electrochemical reactions may introduce significant error in the measurement. Typically, the potential between the electrodes as well as the specific redox mediator and optional second electron transfer agent are chosen so that the analyte will be almost completely electrolyzed in less than 5 minutes, based on the expected concentration of the analyte in the sample. Preferably, the analyte will be almost completely electrolyzed within about 2 minutes and, more preferably, within about 1 minute.

In another embodiment of the invention, the analyte is only partially electrolyzed. The current is measured during the partial reaction and then extrapolated using mathematical techniques known to those skilled in the art to determine the current curve for the complete or nearly complete electrolysis of the analyte. Integration of this curve yields the amount of charge that would be passed if the analyte were completely or nearly completely electrolyzed and, using equation (3a) or (3b), the concentration of the analyte is calculated.

Although coulometry has the disadvantage of requiring the volume of the measured sample be known, coulometry is a preferred technique for the analysis of the small sample because it has the advantages of, for example, no temperature dependence for the measurement, no enzyme activity dependence for the measurement, no redox-mediator activity dependence for the measurement, and no error in the measurement from depletion of analyte in the sample. As already described above, coulometry is a method for determining the amount of charge passed or projected to pass during complete or nearly complete electrolysis of the analyte. One coulometric technique involves electrolyzing the analyte on a working electrode and measuring the resulting current between the working electrode and a counter electrode at two or more times during the electrolysis. The electrolysis is complete when the current reaches a steady state. The charge used to electrolyze the sample is then calculated by integrating the measured currents over time and accounting for any background signal. Because the charge is directly related to the amount of analyte in the sample there is no temperature dependence of the measurement. In addition, the activity of the enzyme does not affect the value of the measurement, but only the time required to obtain the measurement (i.e., less active enzyme requires a longer time to achieve complete electrolysis of the sample) so that decay of the enzyme over time will not render the analyte concentration determination inaccurate. And finally, the depletion of the analyte in the sample by electrolysis is not a source of error, but rather the objective of the technique. (However, the analyte need not be completely electrolyzed if the electrolysis curve is extrapolated from the partial electrolysis curve based on well-known electrochemical principles.)

Non-Coulometric Assays

Although coulometric assays are useful, those skilled in the art will recognize that a sensor of the invention may also utilize potentiometric, amperometric, voltammetric, and other electrochemical techniques to determine the concentration of an analyte in a sample. The measurements obtained by these non-coulometric methods may not be temperature independent as are coulometric measurements.

In addition, the measurements obtained by these non-coulometric electrochemical techniques may be sensitive to the amount of active enzyme provided in the sensor. If the enzyme deactivates or decays over time, the resulting measurements may be affected. This may limit the shelf life of such sensors unless the enzyme is very stable.

Finally, the measurements obtained by non-coulometric electrochemical techniques, such as steady-state amperometry, may be negatively affected if a to substantial portion of the analyte and/or redox mediator is electrolyzed during the measurement period. An accurate steady-state measurement may not be obtainable unless there is sufficient analyte and/or redox mediator so that only a relatively small portion of the analyte and/or redox mediator is electrolyzed during the measurement process. This may be challenging in a sample size of no more than 1 μl.

It may be desirable in some instances to utilize non-coulometric assays, such as amperometric or potentiometric measurement techniques. For example, coulometry requires that the volume of the measured sample be known. And, the volume of the sample in the measurement zone of a small volume sensor (i.e., no more than one microliter) may be difficult to accurately reproduce if the manufacturing tolerances of one or more dimensions of the measurement zone have significant variances.

As described for coulometric measurements, the background signal resulting from the shuttling of the redox mediator between the electrodes can be a source of measurement error in amperometric or potentiometric assays of samples of no more than 1 μL in thin layer electrochemical cells. In general, it is desirable that the mediator does not shuttle between a pair of electrodes more than ten times in the period of the measurement, preferably not more than once, and more preferably not more than 0.1 times, on average. To decrease error arising from background signal, methods and sensor configurations similar to, and in some cases identical to, those used for coulometric measurements may be used. Examples include all of the methods and structures described above, such as performing the electrochemical assay at relatively low applied potential, electrooxidizing the analyte at negative applied potentials or electroreducing the analyte at positive applied potentials, using a counter electrode at which the redox mediator reacts relatively slowly (particularly as compared to the reaction of the redox mediator at the working electrode), and/or using a redox mediator that undergoes an irreversible reaction at the counter electrode. Other examples are discussed below.

As described for coulometric measurements, it is preferred that the sensor be designed and operated so that the background signal is at most five times the size of the signal generated by electrolysis of the analyte. Preferably, the background signal is at most 200%, 100%, 50%, 25%, 10%, or 5% of the signal generated by electrolysis of an amount of analyte. The amount of analyte against which the background signal is compared is described above in the section entitled "Background Signal." In the case of amperometry, the signal generated by electrolysis of an amount of analyte is the current at the time or times at which the measurement is taken. In the case of potentiometry, the signal generated by electrolysis of an amount of analyte is the potential at the time or times at which the measurement is taken.

Under a given set of operating conditions, for example, temperature, cell geometry, and electrode size, the magnitude of the background current, $I_{back}$, is given by the following expression:

$$i_{back} = K C_M D_M / d$$

where: K is a proportionality constant; $C_M$ is the concentration of the mediator in the measurement zone; $D_m$ is the effective diffusion coefficient of the mediator in the measurement zone under normal operating conditions; and d is the distance between the electrodes.

It is desirable to reduce background current for non-coulometric assays. The sensor configurations and methods described above are generally useful and include, for example, using low concentrations of the redox mediator and/or the second electron transfer agent (e.g., enzyme) relative to the concentration of the analyte and/or using a large redox mediator having a relatively low effective diffusion constant. Other useful methods described above include methods for reducing the diffusion of the redox mediator by, for example, having a barrier (e.g., a charged or polar barrier) to the flow of the diffusible mediator or using a redox mediator having a relatively low effective diffusion constant.

In some instances, the effective diffusion coefficient is no more than about $1 \times 10^{-6}$ cm$^2$/sec, no more than about $1 \times 10^{-7}$ cm$^2$/sec, or no more than about $1 \times 10^{-8}$ cm$^2$/sec. Moreover, in some cases, the product of $C_M D_M$ (the concentration of redox mediator times the effective diffusion coefficient) is no more than about $1 \times 10^{-12}$ moles/cm·sec, no more than about $1 \times 10^{-13}$ moles/cm·sec, or no more than about $1 \times 10^{-14}$ moles/cm·sec.

The following provides a specific example for the case of an amperometric measurement of glucose carried out for 60 seconds during which time 10% of the glucose is electrolyzed in a 1 microliter cell with facing electrodes separated by a distance of d=0.01 cm. If the measurement was carried out under the following conditions: a glucose concentration of, $C_G$=5 mM (or $5 \times 10^{-6}$ moles/cm$^3$), an area of A=0.1 cm$^2$, a number of electrons from the redox mediator of $n_M$=1, and a number of electrons from glucose $n_G$=2, then the background current generated by the redox mediator and by the glucose is determined as follows.

$$i_{back} = AFn_M D_M C_M / d = (0.1)(96,500)(1) D_M C_M / (0.01) = 9.65 \times 10^5 C_M D_M$$

$$i_G = n_G A d(0.1) F C_G / t = (2)(0.01)(0.1)(96,500)(5 \times 10^{-6})/60 = 1.61 \; \mu\text{amps}$$

Thus if $i_{back}/i_G$=5, the value of $C_M D_M$ equal $8.34 \times 10^{-12}$ moles/cm$^2$ sec. As another example, $i_{back}/i_G$=0.5, the value of $C_M D_M$ equal $8.34 \times 10^{-13}$ moles/cm$^2$ sec. Additionally if $i_{back}/i_G$=0.05, the value of $C_M D_M$ equal $8.34 \times 10^{-14}$ moles/cm$^2$ sec.

In some amperometric or potentiometric embodiments, the redox mediator circulation is decreased by separating the working electrode from the counter or counter/reference electrode such that the distance through which the redox mediator would diffuse during the measurement period is no greater than, for example, the distance between the electrodes. A redox mediator can diffuse a distance equal to $(D_m t)^{1/2}$, where $D_m$ is the effective diffusion coefficient for the medium between the electrodes and t is time. For a measurement time period of 30 seconds and a redox mediator with effective diffusion coefficient between $10^{-5}$ and $10^{-6}$ cm$^2$/second, the electrodes should be separated by at least 100 µm, preferably at least 200 µm, and even more preferably at least 400 µm.

One method of separating the working and counter electrodes is to use a thicker spacer between the electrodes. One alternative method is illustrated in FIG. 27. In this embodiment, the working electrode 740 is disposed on a first substrate 742 and the counter electrode 744 is disposed on a second substrate 746 (alternatively, the electrodes may be disposed on the same substrate). The working electrode 742 and the counter electrode 744 are offset so that the effective distance, d, between the two electrodes is greater than the thickness, w, of the spacer layer 748. In one embodiment, the distance between the electrodes, d, is selected to be in the range of 25 to 1000 µm, 50 to 500 µm, or 100 to 250 µm.

Additionally or alternatively, in the case of steady-state amperometry and potentiometry, background signal may be controlled by limiting the rate of electrolysis such that the rate is slow enough to prevent the analyte concentration from decreasing by more than about 20%, 10%, or 5% or less, during a measurement period, e.g., 30 second, 1 minute, 5 minutes, or 10 minutes. In some instances, to control the rate of electrolysis the concentration or activity of the second electron transfer agent may be reduced and/or the working electrode area may be reduced.

For example, the second electron transfer agent can be an enzyme and the enzyme activity can be a limiting factor for the electrolysis rate. If, for example, the analyte concentration is 5 mM glucose (i.e., $5 \times 10^{-9}$ moles of glucose in 1 µl) and no more than 10% of the glucose ($5 \times 10^{-10}$ moles) is to be electrooxidized during a 30-second measurement period, the current should not exceed $3.3 \times 10^{-6}$ amperes for 1 µL. One unit of an enzyme is that amount of the enzyme which catalyzes electrolysis of 1 µmole of its substrate in 60 seconds at pH of 7.4 at 37° C. in HEPES buffer. Accordingly, for glucose, a current of up to $3.3 \times 10^{-3}$ amperes in 1 cm$^3$ (i.e., 1 mL) can be generated. Therefore, the maximum amount of enzyme used in a sensor that limits the amount of electrolysis by controlling the amount of enzyme should be 1 unit/cm$^3$ or less.

The rate of electrolysis may also be limited by using a relatively small working electrode area. When the working electrode area is sufficiently small (e.g., no more than about 0.01 cm$^2$, no more than about 0.0025 cm$^2$, or no more than about 0.001 cm$^2$), then radial diffusion of analyte to the electrode may result in a steady-state current, at a constant applied potential, that is representative of the analyte concentration. For circular electrodes, the appropriate surface area may be achieved using an electrode with a radius of no more than 60 µm, no more than 30 µm, or no more than 20 µm. Radial diffusion of the analyte includes transport of analyte from all directions and not just from the direction normal to the electrode surface and can, therefore, reduce or prevent depletion of analyte near the electrode surface. A small electrode on a planar surface permits radial diffusion. In a sensor having a larger surface area electrodes, the transport of analyte to the electrode may be modeled as semi-infinite linear diffusion instead of radial diffusion. Thus, the transport of the analyte to the electrode is dominated by diffusion from the direction normal to the electrode surface. As a result, the reduced transport rate is typically unable to overcome the depletion of analyte near the electrode surface, and at constant applied potential the current decreases with time, t, according to $t^{-1/2}$.

For a potentiometric assay of the type proposed by Yarnitzky and Heller, *J. Phys. Chem.*, 102:10057-61 (1998), in which the potential varies linearly with the analyte concentration, the concentration of the analyte and/or redox mediator in a particular oxidation state should vary no more than about 20% during the assay. If the concentration varies by more than 20%, then the diffusion of the analyte or redox mediator should be controlled by, for example, controlling temperature and/or volume of the sample chamber and/or measurement zone.

While this description has described electrolysis of an analyte, one skilled in the art would recognize that the same devices and techniques would also be suitable for measurements of the average oxidation state of the mediator, such as, for example, in Cottrell types of reactions.

Air-Oxidizable Redox Mediators

In a sensor having a redox mediator, a potential source of measurement error is the presence of redox mediator in an unknown mixed oxidation state (i.e., mediator not reproducibly in a known oxidation state). The charge passed when the redox mediator is electrooxidized or electroreduced at the working electrode is affected by its initial oxidation state. Referring to equations (1) and (2) discussed above under the section entitled "Operation of the Sensor," the current not attributable to the oxidation of biochemical B will flow because of electrooxidation of that portion of the redox mediator, A, that is in its reduced form prior to the addition of the sample. Thus, it may be important to know the oxidation state of the analyte prior to introduction of the sample into the sensor. Furthermore, it is desirable that all or nearly all of the redox mediator have the same state or extent of oxidation prior to the introduction of the sample into the sensor.

Each redox mediator has a reduced form or state and an oxidized form or state. It is preferred that the amount of redox mediator in the reduced form prior to the introduction of sample be significantly smaller than the expected amount of analyte in a sample in order to avoid a significant background contribution to the measured current. In this embodiment of the invention, the molar amount of redox mediator in the reduced form prior to the introduction of the analyte is preferably no more than, on a stoichiometric basis, about 10%, and more preferably no more than about 5%, and most preferably no more than 1%, of the molar amount of analyte for expected analyte concentrations. (The relative molar amounts of analyte and redox mediator are compared based on the stoichiometry of the applicable redox reaction. If, for example, two moles of redox mediator are needed to electrolyze one mole of analyte, then the molar amount of redox mediator in the reduced form prior to introduction of the analyte is preferably no more than 20% and more preferably no more than about 10% and most preferably no more than about 2% of the molar amount of analyte for expected analyte concentrations.) Methods for controlling the amount of reduced mediator are discussed below.

In another aspect of the invention, it is preferred that the ratio of the amounts of oxidized redox mediator to reduced redox mediator, prior to introduction of the sample in the sensor, be relatively constant between similarly constructed sensors. Any deviation from holding the ratio relatively constant may increase the scatter of the results obtained for the same sample with multiple similarly made sensors. For this aspect of the invention, the percentage of the redox mediator in the reduced form prior to introduction of the sample in the sensor varies by no more than about 20% and preferably no more than about 10% between similarly constructed sensors.

One method of controlling the amount of reduced redox mediator prior to the introduction of the sample in the sensor is to provide an oxidizer to oxidize the reduced form of the mediator. One of the most convenient oxidizers is $O_2$. Oxygen is usually readily available to perform this oxidizing function. Oxygen can be supplied by exposing the sensor to air. In addition, most polymers and fluids absorb $O_2$ from the air unless special precautions are taken. Typically, at least 90% of an air-oxidizable (i.e., $O_2$ oxidizable) mediator in the solid state is in the oxidized state upon storage or exposure to air for a useful period of time, e.g., one month or less, and preferably, one week or less, and, more preferably, one day or less. The air oxidation may take place in either the solid state or as a solution stored for a time period sufficient to air oxidize the mediator before deposition on the sensor. In the case of air oxidizable redox mediators in solution, it is desirable that the time required to achieve at least 80%, preferably at least 90%, oxidation of the redox mediator is at least 10 times the expected duration of the assay and is also less than the pot life of the solution. Preferably, at least 80%, more preferably at least 90%, of the redox mediator is air oxidized in less than 1 week, preferably, in less than 1 day, more preferably, in less than 8 hours, and even more preferably, in less than 1 hour.

While it is desirable to bring the mediators of the sensors manufactured in a single batch to the same state or extent of oxidation, it is not necessary that the mediator be completely oxidized to the higher-valent state. Additionally, it is desirable that the air oxidation of the dissolved redox mediator should not be so fast that air-oxidation during the assay can interfere with or introduce error into the measurements.

Suitable mediators which are both air-oxidizable (i.e., $O_2$-oxidizable) and have electron transfer capabilities have been described hereinabove. One particular family of useful mediators are osmium complexes which are bound to electron-rich nitrogen-containing heterocycles or a combination of electron-rich nitrogen-containing heterocycles and halides. Electron-rich nitrogen-containing heterocycles include, but are not limited to, imidazole derivatives and pyridine or phenanthroline derivatives that contain electron-donating substituents such as alkyl, alkoxy, amino, alkylamino, amido and mercapto groups. Preferably, the osmium complexes have no more than one halide coordinated to the metal, so that the mediators are overall positively charged and thus are water soluble. An example is osmium complexed with mono-, di-, and polyalkoxy-2,2'-bipyridine. Other examples include mono-, di-, and polyalkoxy-1,10-phenanthroline, where the alkoxy groups have a carbon to oxygen ratio sufficient to retain solubility in water, are air-oxidizable. These osmium complexes typically have two substituted bipyridine or substituted phenanthroline ligands, the two ligands not necessarily being identical. These osmium complexes are further complexed with a monomeric or polymeric ligand with one or more nitrogen-containing heterocycles, such as pyridine and imidazole. Preferred polymeric ligands include poly(4-vinyl pyridine) and, more preferably, poly(1-vinyl imidazole) or copolymers thereof. [Os[4,4'-dimethoxy-2,2'-bipyridine]$_2$Cl]$^{+/+2}$ complexed with a poly(1-vinyl imidazole) or poly(4-vinyl pyridine) has been shown to be particularly useful as the $Os^{+2}$ cation is oxidizable by $O_2$ to $Os^{+3}$. Similar results are expected for complexes of [Os(4,7-dimethoxy-1,10-phenanthroline)$_2$Cl]$^{+/+2}$, and other mono-, di-, and polyalkoxy bipyridines and phenanthrolines, with the same polymers. Other halogen groups such as bromine may be substituted for chlorine. Similar results are also expected for complexes comprising the following structures, as specified above:

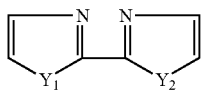

A complication associated with air-oxidizable mediators arises if the air oxidation of the redox mediator is so fast that a substantial portion of the analyte-reduced redox mediator is oxidized by $O_2$ during an analyte assay. This will result in an inaccurate assay as the amount of analyte will be underestimated because the mediator will be oxidized by air rather than by its electrooxidation at the electrode. It is preferred that the reaction of the redox mediator with $O_2$ proceeds more slowly than the electrooxidation of the mediator, because if the air oxidation of the mediator were fast, then dissolved air and the in-diffusion of air might affect the outcome of the measurement.

Because typically the assay takes about 10 minutes or less, preferably 5 minutes or less, and most preferably about 1 minute or less, it is preferred that the mediator, though air oxidizable in storage, will not be oxidized by dissolved oxygen during the time of the assay. Thus, mediators that are not air oxidized in 1 minute, and preferably not even in 10 minutes when dissolved in plasma or in serum, are preferred. Typically, less than 5%, and preferably less than 1%, of the reduced mediator should be oxidized by air during an assay.

The reaction rate of the air oxidation of the mediator can be controlled through choice of an appropriate complexing polymer. For example, the oxidation reaction is much faster for [Os(4,4'-dimethoxy-2,2'-bipyridine)$_2$Cl]$^{+/+2}$ coordinatively coupled to poly(1-vinyl imidazole) than for the same Os complex coupled to poly(4-vinyl pyridine). The choice of an appropriate polymer will depend on the expected analyte concentration and the potential applied between the electrodes, both of which determine the rate of the electrochemical reaction.

Thus, in one embodiment of the invention, the preferred redox mediator has the following characteristics: 1) the mediator does not react with any molecules in the sample or in the sensor other than the analyte (optionally, via a second electron transfer agent); 2) nearly all of the redox mediator is oxidized by an oxidizer such as $O_2$ prior to introduction of the sample in the sensor; and 3) the oxidation of the redox mediator by the oxidizer is slow compared to the electrooxidation of the mediator by the electrode.

Alternatively, if the redox mediator is to be oxidized in the presence of the analyte and electroreduced at the electrode, a reducer rather than an oxidizer would be required. The same considerations for the appropriate choice of reducer and mediator apply as described hereinabove for the oxidizer.

The use of stable air-oxidizable redox mediators in the electrochemical sensors of the invention provides an additional advantage during storage and packaging. Sensors of the invention which include air-oxidizable redox mediators can be packaged in an atmosphere containing molecular oxygen and stored for long periods of time, e.g., greater than one month, while maintaining at least 80% and preferably at least 90% of the redox species in the oxidized state.

Use of the Air-Oxidizable Mediators in Optical Sensors

The air-oxidizable redox species of the present invention can be used in other types of sensors. The osmium complexes described hereinabove are suitable for use in optical sensors, due to the difference in the absorption spectra, luminescence and/or fluorescence characteristics of the complexed $Os^{+2}$ and $Os^{+3}$ species. Absorption, transmission, reflection, luminescence and/or fluorescence measurements of the redox species will correlate with the amount of analyte in the sample (after reaction between an analyte and the redox species, either directly, or via a second electron transfer agent such as an enzyme). In this configuration, the molar amount of redox mediator should be greater, on a stoichiometric basis, than the molar amount of analyte reasonably expected to fill the measurement zone of the sensor.

Standard optical sensors, including light-guiding optical fiber sensors, and measurement techniques can be adapted for use with the air-oxidizable mediators. For example, the optical sensors of the invention may include a light-transmitting or light reflecting support on which the air-oxidizable redox species, and preferably an analyte-responsive enzyme, is coated to form a film. The support film forms one boundary for the measurement zone in which the sample is placed. The other boundaries of the measurement zone are determined by the configuration of the cell. Upon filling the measurement zone with an analyte-containing sample, reduction of the air-oxidizable mediator by the analyte, preferably via reaction with the analyte-responsive enzyme, causes a shift in the mediator's oxidation state that is detected by a change in the light transmission, absorption, or reflection spectra or in the luminescence and/or fluorescence of the mediator at one or more wavelengths of light.

Multiple Electrode Sensors and Calibration

Multiple electrode sensors may be used for a variety of reasons. For example, multiple electrode sensors may be used to test a variety of analytes using a single sample. One embodiment of a multiple electrode sensor, shown in FIG. 5, has one or more sample chambers which in turn may contain one or more working electrodes 22 with each working electrode 22 defining a different measurement zone. If the redox mediator is non-leachable, one or more of the working electrodes have the appropriate chemical reagents, for example, an appropriate enzyme, to test a first analyte and one or more of the remaining working electrodes have appropriate chemical reagents to test a second analyte. The chemical reagents (e.g., redox mediator and/or second electron transfer agent) can be deposited as a sensing layer on the working electrode or, if diffusible reagents are used, they can be deposited on any surface of the sample chamber or placed in the sample. For example, a multiple electrode sensor might include 1) one or more working electrodes having glucose oxidase in the sensing layer to determine glucose concentration and 2) one or more working electrodes having lactate oxidase in the sensing layer to determine lactate concentration.

Multiple electrode sensors may also be used to improve the precision of the resulting readings. The measurements from each of the working electrodes (all or which are detecting the same analyte) can be averaged together to obtain a more precise reading. In some cases, measurements may be rejected if the difference between the value and the average exceeds a threshold limit. This threshold limit may be, for example, determined based on a statistical parameter, such as the standard deviation of the averaged measurements. The average may then be recalculated while omitting the rejected values. Furthermore, subsequent readings from an electrode that produced a rejected value may be ignored in later tests if it is assumed that the particular electrode is faulty. Alternatively, a particular electrode may be rejected only after having a predetermined number of readings rejected based on the readings from the other electrodes.

In addition to using multiple electrode sensors to increase precision, multiple measurements may be made at each electrode and averaged together to increase precision. This technique may also be used with a single electrode sensor to increase precision.

Errors in assays may occur when mass produced sensors are used because of variations in the volume of the measurement zone of the sensors. Two of the three dimensions of the measurement zone, the length and the width, are usually relatively large, between about 1-5 mm. Electrodes of such dimensions can be readily produced with a variance of 2% or less. The submicroliter measurement zone volume requires, however, that the third dimension be smaller than the length or width by one or two order of magnitude. As mentioned hereinabove, the thickness of the sample chamber is typically between about 50 and about 200 µm. Manufacturing variances in the thickness may be on the order of 20 to 50 µm. Therefore, it may be desirable that a method be provided to accommodate for this uncertainty in the volume of sample within the measurement zone.

In one embodiment of the invention, depicted in FIG. 5, multiple working electrodes 42, 44, 46 are provided on a base material 48. These electrodes are covered by another base, not shown, which has counter electrodes, not shown, disposed upon it to provide multiple facing electrode pairs. The variance in the separation distance between the working electrode and the counter electrode among the electrode pairs on a given sensor is significantly reduced, because the working electrodes and counter electrodes are each provided on a single base with the same spacer 28 between each electrode pair (see FIG. 3).

One example of a multiple electrode sensor that can be used to accurately determine the volume of the measurement zones of the electrode pairs and that is also useful in reducing noise is presented herein. In this example, one of the working electrodes 42 is prepared with a non-leachable redox mediator and a non-leachable second electron transfer agent (e.g., an enzyme). Sorbent material may be disposed between that working electrode 42 and its corresponding counter electrode. Another working electrode 44 includes non-leachable redox mediator, but no second electron transfer agent on the electrode. Again, this second electrode pair may have sorbent material between the working electrode 44 and the corresponding counter electrode. An optional third working electrode 46 has no redox mediator and no second electron transfer agent hound to the electrode, nor is there sorbent material between the working electrode 46 and its corresponding counter electrode. A similar configuration can be constructed using diffusible redox mediator and/or diffusible second electron transfer agent although diffusible components are not limited to being disposed on the working electrode. In some instances, the distance between electrode pairs is sufficient that redox mediator and/or enzyme do not substantially diffuse between electrode pairs within the measurement period and/or in the time period from introduction of the same sample into the sample chamber to the end of the measurement.

The sensor error caused by redox mediator in a non-uniform oxidation state prior to the introduction of the sample can be measured by concurrently electrolyzing the sample in the measurement zones that are proximate electrodes 42 and 44. At electrode 42, the analyte is electrolyzed to provide the sample signal. At electrode 44, the analyte is not electrolyzed because of the absence of the second electron transfer agent (assuming that a second electron transfer agent is necessary). However, a charge will pass (and a current will flow) due to the electrolysis of the redox mediator that was in a mixed oxidation state (i.e., some redox centers in the reduced state and some in the oxidized state) prior to the introduction of the sample and/or the shuttling of a diffusible redox mediator between the working electrode and the counter electrode. The small charge passed between the electrodes in this second electrode pair can be subtracted from the charge passed between the first electrode pair to substantially remove the error due to the oxidation state of the redox mediator and/or to remove the background current caused by a diffusible redox mediator. This procedure also reduces the error associated with other electrolyzed interferents, such as ascorbate, urate, and acetaminophen, as well as errors associated with capacitive charging and faradaic currents.

The thickness of the sample chamber can be determined by measuring the capacitance, preferably in the absence of any fluid, between electrode 46 (or any of the other electrodes 42, 44 in the absence of sorbent material) and its corresponding counter electrode. The capacitance of an electrode pair depends on the surface area of the electrodes, the interelectrode spacing, and the dielectric constant of the material between the plates. The dielectric constant of air is unity which typically means that the capacitance of this electrode configuration is a few picofarads (or about 100-1000 picofarads if there is fluid between the electrode and counter electrode given that the dielectric constant for most biological fluids is approximately 75). Thus, since the surface area of the electrodes are known, measurement of the capacitance of the electrode pair allows for the determination of the thickness of the measurement zone to within about 1-5%.

The amount of void volume in the sorbent material, can be determined by measuring the capacitance between electrode 44 (which has no second electron transfer agent) and its associated counter electrode, both before and after fluid is added. Upon adding fluid, the capacitance increases markedly since the fluid has a much larger dielectric constant. Measuring the capacitance both with and without fluid allows the determination of the spacing between the electrodes and the void volume in the sorbent, and thus the volume of the fluid in the reaction zone.

Other electrode configurations can also use these techniques (i.e., capacitance measurements and coulometric measurements in the absence of a critical component) to reduce background noise and error due to interferents and imprecise knowledge of the volume of the interrogated sample. Protocols involving one or more electrode pairs and one or more of the measurements described above can be developed and are within the scope of the invention. For example, only one electrode pair is needed for the capacitance measurements, however, additional electrode pairs may be used for convenience.

Fill Indicator

When using a sample chamber that is filled with 1 μL or less of fluid, it is often desirable to be able to determine when the sample chamber is filled. FIGS. 18A-18C illustrate one sensor having a fill indicator structure. FIG. 18A illustrates a first substrate 500 upon which a working electrode 502 is printed. A spacer 504 (FIG. 18B), such as, for example, a layer of adhesive or a double-sided tape, is formed over the first substrate 500 and working electrode 502 with a channel 506 formed in the layer to provide a sample chamber. A second substrate 508 is printed with two counter electrodes 510, 512, as shown in FIG. 18C (inverted with respect to FIGS. 18A and 18B to show the electrode side up). In some instances, the counter electrode 510 nearest an entrance 514 of the channel 506 has a surface area within the sample chamber that is at least two times larger than the other counter electrode 512, and preferably at least five or ten times larger.

The sensor can be indicated as filled by observing a signal between the second counter electrode 512 and the working electrode 502 as the sensor fills with fluid.

When fluid reaches the second counter electrode 512, the signal from that counter electrode should change. Suitable signals for observing include, for example, voltage, current, resistance, impedance, or capacitance between the second counter electrode 512 and the working electrode 502. Alternatively, the sensor may be observed after filling to determine if a value of the signal (e.g., voltage, current, resistance, impedance, or capacitance) has been reached indicating that the sample chamber is filled.

In alternative embodiments, the counter electrode and/or working electrode may be divided into two or more parts and the signals from the respective parts observed to determine whether the sensor has been filled. In one example, the working electrode is in a facing relationship with the counter electrode and the indicator electrode. In another example, the counter electrode, working electrode, and indicator electrode are not in a facing relationship, but may be, for example, side-by-side. In other cases, a second electrode pair may be used with signals from the second electrode pair being monitored for changes and/or for approaching a particular value to determine that the sensor has filled. Typically, the indicator electrode is further downstream from a sample inlet port than the working electrode and counter electrode.

For side-fill sensors, such as those illustrated in FIGS. 19A-19C and 20A-20C, two indicator electrodes may be disposed on either side of the primary counter electrode. This permits the user to fill the sample chamber from either the left or right side with an indicator electrode disposed further upstream. This three-electrode configuration is not necessary. Side-fill sensors can also have a single indicator electrode and, preferably, some indication as to which side should be placed in contact with the sample fluid.

In one embodiment, the use of three counter/reference electrodes and/or indicator electrodes, detects when the sample chamber begins to fill and when the sample chamber has been filled to prevent partial filling of the sample chamber. In this embodiment, the two indicator electrodes are held at a different potential than the largest counter/reference electrode. The start and completion of filling of the sample chamber is indicated by the flow of current between the indicator and counter/reference electrodes.

In other instances, the potential of each of the counter/reference electrodes may be the same. When the potential at all three counter/reference electrodes is the same for example, 0 volts, then as the measurement zone begins to fill, the fluid allows for electrical contact between a working electrode and the first counter/reference electrode, causing a current at the first counter/reference electrode due to the reaction of the analyte with the enzyme and the mediator. When the fluid reaches the third counter/reference electrode, another current may be measured similar to the first counter/reference electrode indicating that the measurement zone is full. When the measurement zone is full, the three counter/reference electrodes may be shorted together or their signals may be added or otherwise combined.

The indicator electrode may also be used to improve the precision of the analyte measurements according to the methods described above for multiple electrode sensors. The indicator electrode may operate as a working electrode or as a counter electrode or counter/reference electrode. In the embodiment of FIGS. 18A-18C, the indicator electrode 512 can act as a second counter or counter/reference electrode with respect to the working electrode 502. Measurements from the indicator electrode/working electrode pair can be combined (for example, added to and/or averaged) with those from the first counter or counter/reference electrode/working electrode pair to obtain more accurate measurements. In one embodiment, the indicator electrode may operate as a second working electrode with the counter electrode or counter/reference electrode. In another embodiment, the indicator electrode may operate as a second working electrode with a second counter electrode or counter/reference electrode. In still another embodiment, the indicator electrode may operate as a second counter electrode or counter/reference electrode with a second working electrode.

The sensor or a sensor reader may include a sign (e.g., a visual sign or auditory signal) that is activated in response to the indicator electrode to alert the user that the measurement zone has been filled. In some instances, the sensor or a sensor reader may be configured to initiate a reading when the indicator electrode indicates that the measurement zone has been filled with or without alerting the user. The reading can be initiated, for example, by applying a potential between the working electrode and the counter electrode and beginning to monitor the signals generated at the working electrode.

Heating of Sample

The sample may be heated to increase the rate of diffusion, oxidation, or reduction of the analyte. This heating may be accomplished by a variety of techniques including placing the sensor in a heated environment or applying a heating unit to the sensor.

Another technique includes providing a thermal heating element, such as, for example, a wire or an ink that is capable of converting electrical energy into heat energy, on the sensor. This wire or ink can be applied, for example, on the opposite side of a base material, such as a polymer film, from one or more of the working, counter, reference, or counter/reference electrodes, or applied around the periphery of the working, counter, reference, or counter/reference electrodes. In some instances, the sample may be heated up to 5 to 20° C. above an initial temperature. In other instances, the temperature of the sample may not be known but a constant amount of power or current may be applied to the wire or ink.

EXAMPLES

The invention will be further characterized by the following examples. These examples are not meant to limit the scope of the invention which has been fully set forth in the foregoing description. Variations within the concepts of the invention are apparent to those skilled in the art.

Example 1

Preparation of a Small Volume In Vitro Sensor for the Determination of Glucose Concentration A sensor was constructed corresponding to the embodiment of the invention depicted in FIG. 1. The working electrode was constructed on a Mylar™ film (DuPont), the Mylar™ film having a thickness of 0.175 mm and a diameter of about 2.5 cm. An approximately 12 micron thick carbon pad having a diameter of about 1 cm was screen printed on the Mylar™ film. The carbon electrode was overlaid with a water-insoluble dielectric insulator (Insulayer) having a thickness of 12 μm, and a 4 mm diameter opening in the center.

The center of the carbon electrode, which was not covered by the dielectric, was coated with a non-leachable redox mediator. The redox mediator was formed by complexing poly(1-vinyl imidazole) with $Os(4,4'\text{-dimethoxy-}2,2'\text{-bipyridine})_2Cl_2$ followed by cross-linking glucose oxidase with the osmium polymer using polyethylene glycol diglycidyl ether (PEGDGE) as described in Taylor et al., *J. Electroanal. Chem.*, 396:511 (1995). The ratio of osmium to imidazole functionalities in the redox mediator was approximately 1:15. The mediator was deposited on the working electrode in a layer having a thickness of 0.6 μm and a diameter of 4 mm. The coverage of the mediator on the electrode was about 60 μg/cm$^2$ (dry weight). A spacer material was placed on the electrode surrounding the mediator-covered surface of the electrode. The spacer was made of polytetrafluoroethylene (PTFE) and had a thickness of about 0.040 mm.

A sorbent material was placed in contact with the mediator-covered surface of the working electrode. The sorbent was made of nylon (Tetko Nitex nylon 3-10/2). The sorbent had a diameter of 5 mm, a thickness of 0.045 mm, and a void volume of about 20%. The volume of sample in the measurement zone was calculated from the dimensions and characteristics of the sorbent and the electrode. The measurement zone had a diameter of 4 mm (the diameter of the mediator covered surface of the electrode) and a thickness of 0.045 mm (thickness of the nylon sorbent) to give a volume of 0.57 μL. Of this space, about 80% was filled with nylon and the other 20% was void space within the nylon sorbent. This resulting volume of sample within the measurement zone was about 0.11 μL.

A counter/reference electrode was placed in contact with the spacer and the side of the sorbent opposite to the working electrode so that the two electrodes were facing each other. The counter/reference electrode was constructed on a Mylar™ film having a thickness of 0:175 mm and a diameter of about 2.5 cm onto which a 12 micron thick layer of silver/silver chloride having a diameter of about 1 cm was screen printed.

The electrodes, sorbent, and spacer were pressed together using plates on either side of the electrode assembly. The plates were formed of polycarbonate plastic and were securely clamped to keep the sensor together. The electrodes were stored in air for 48 hours prior to use.

Tabs extended from both the working electrode and the counter/reference electrode and provided for an electrical contact with the analyzing equipment. A potentiostat was used to apply a potential difference of +200 mV between the working and counter/reference electrodes, with the working electrode being the anode. There was no current flow between the electrodes in the absence of sample, which was expected, as no conductive path between the electrodes was present.

The sample was introduced via a small tab of nylon sorbent material formed as an extension from the nylon sorbent in the sample chamber. Liquid was wicked into the sorbent when contact was made between the sample and the sorbent tab. As the sample chamber filled and the sample made contact with the electrodes, current flowed between the electrodes. When glucose molecules in the sample came in contact with the glucose oxidase on the working electrode, the glucose molecules were electrooxidized to gluconolactone. The osmium redox centers in the redox mediator then reoxidized the glucose oxidase. The osmium centers were in turn reoxidized by reaction with the working electrode. This provided a current which was measured and simultaneously integrated by a coulometer (EG&G Princeton Applied Research Model #173).

The electrochemical reaction continued until the current reached a steady state value which indicated that greater than 95% of the glucose had been electroreduced. The current curve obtained by measurement of the current at specific intervals was integrated to determine the amount of charge passed during the electrochemical reaction. These charges were then plotted versus the known glucose concentration to produce a calibration curve.

The sensor was tested using 0.5 μL aliquots of solutions containing known concentrations of glucose in a buffer of artificial cerebrospinal fluid or in a control serum (Baxter-Dade, Monitrol Level 1, Miami, Fla.) in the range of 3 to 20 mM glucose. The artificial cerebrospinal fluid was prepared as a mixture of the following salts: 126 mM NaCl, 27.5 mM $NaHCO_3$, 2.4 mM KCl, 0.5 mM $KH_2PO_4$, 1.1 mM $CaCl_2.2H_2O$, and 0.5 mM $Na_2SO_4$.

Figure 7:
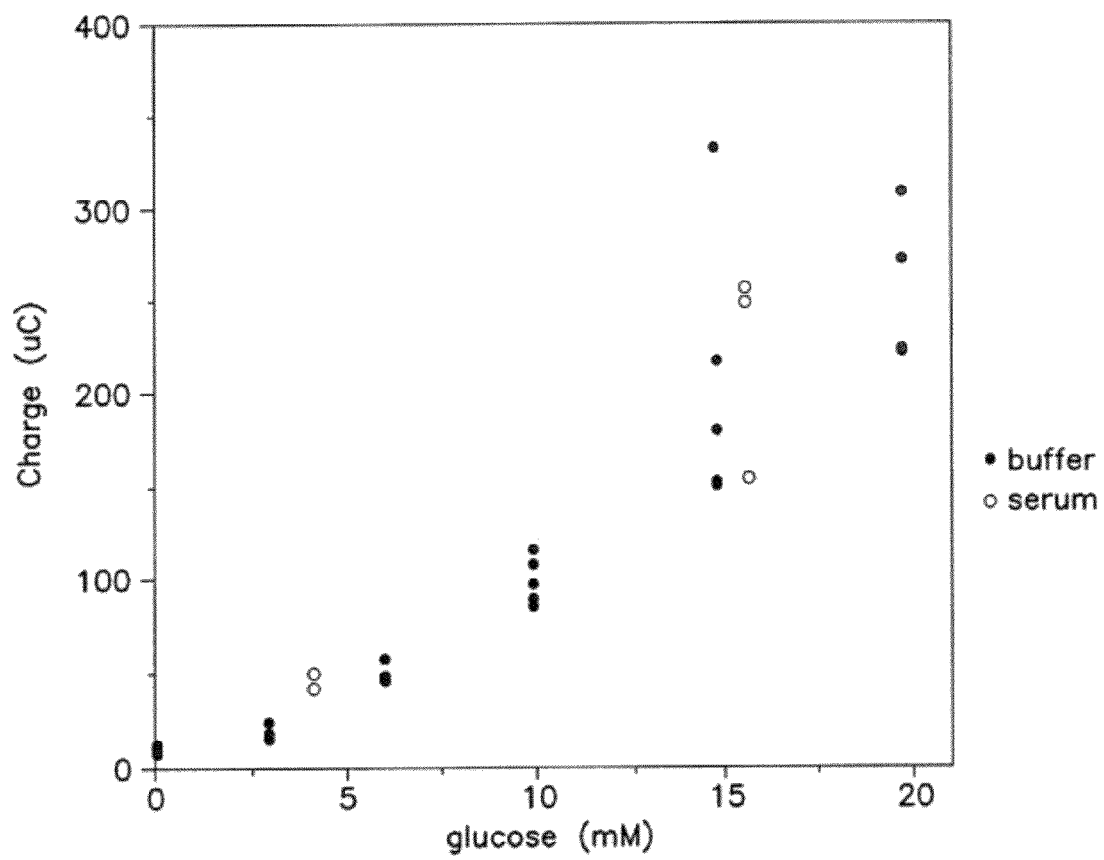
FIG. 7 is a graph of the charge required to electrooxidize a known quantity of glucose in an electrolyte buffered solution (filled circles) or serum solution (open circles) using the sensor of FIG. 1 with glucose oxidase as the second electron transfer agent.

The results of the analyses are shown in Table 1 and in FIG. 7. In Table 1, $Q_{avg}$ is the average charge used to electrolyze the glucose in 3-6 identical test samples (FIG. 7 graphs the charge for each of the test samples) and the 90% rise time corresponds to the amount of time required for 90% of the glucose to be electrolyzed. The data show a sensor precision of 10-20%, indicating adequate sensitivity of the sensor for low glucose concentrations, as well as in the physiologically relevant range (30 μg/dL-600 μg/dL).

TABLE 1

Sensor Results Using Glucose Oxidase

|  | Number of Samples Tested | $Q_{avg}$ (µC) | 90% rise time (sec) |
|---|---|---|---|
| buffer only | 4 | 9.9 ± 1.8 | 13 ± 6 |
| 3 mM glucose/buffer | 5 | 17.8 ± 3.5 | 19 ± 5 |
| 6 mM glucose/buffer | 4 | 49.4 ± 4.9 | 25 ± 3 |
| 10 mM glucose/buffer | 6 | 96.1 ± 12.4 | 36 ± 17 |
| 15 mM glucose/buffer | 5 | 205.2 ± 75.7 | 56 ± 23 |
| 20 mM glucose/buffer | 4 | 255.7 ± 41.0 | 62 ± 17 |
| 4.2 mM glucose/serum | 3 | 44.2 ± 4.3 | 44 ± 3 |
| 15.8 mM glucose/serum | 3 | 218.2 ± 57.5 | 72 ± 21 |

Figure 8:
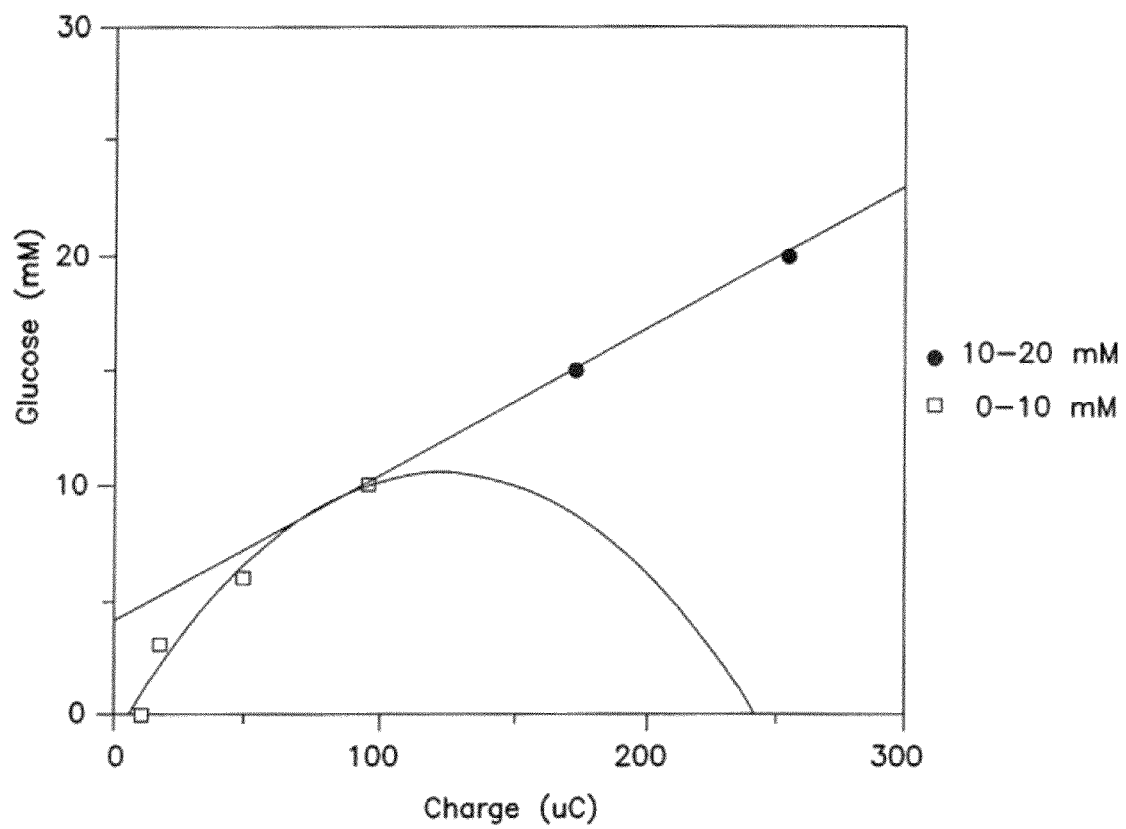
FIG. 8 is a graph of the average glucose concentrations for the data of FIG. 7 (buffered solutions only) with calibration curves calculated to fit the averages; a linear calibration curve was calculated for the 10-20 mM concentrations and a second order polynomial calibration curve was calculated for the 0-10 mM concentrations.

The average measured values of glucose concentration were fit by one or more equations to provide a calibration curve. FIG. 8 shows the calibration curves for the glucose/buffer data of Table 1. One of the 15.0 mM glucose measurements was omitted from these calculations because it was more than two standard deviations away from the average of the measurements. The higher glucose concentrations (10-20 mM) were fit by a linear equation. The lower glucose concentrations were fit by a second order polynomial.

Figure 9:
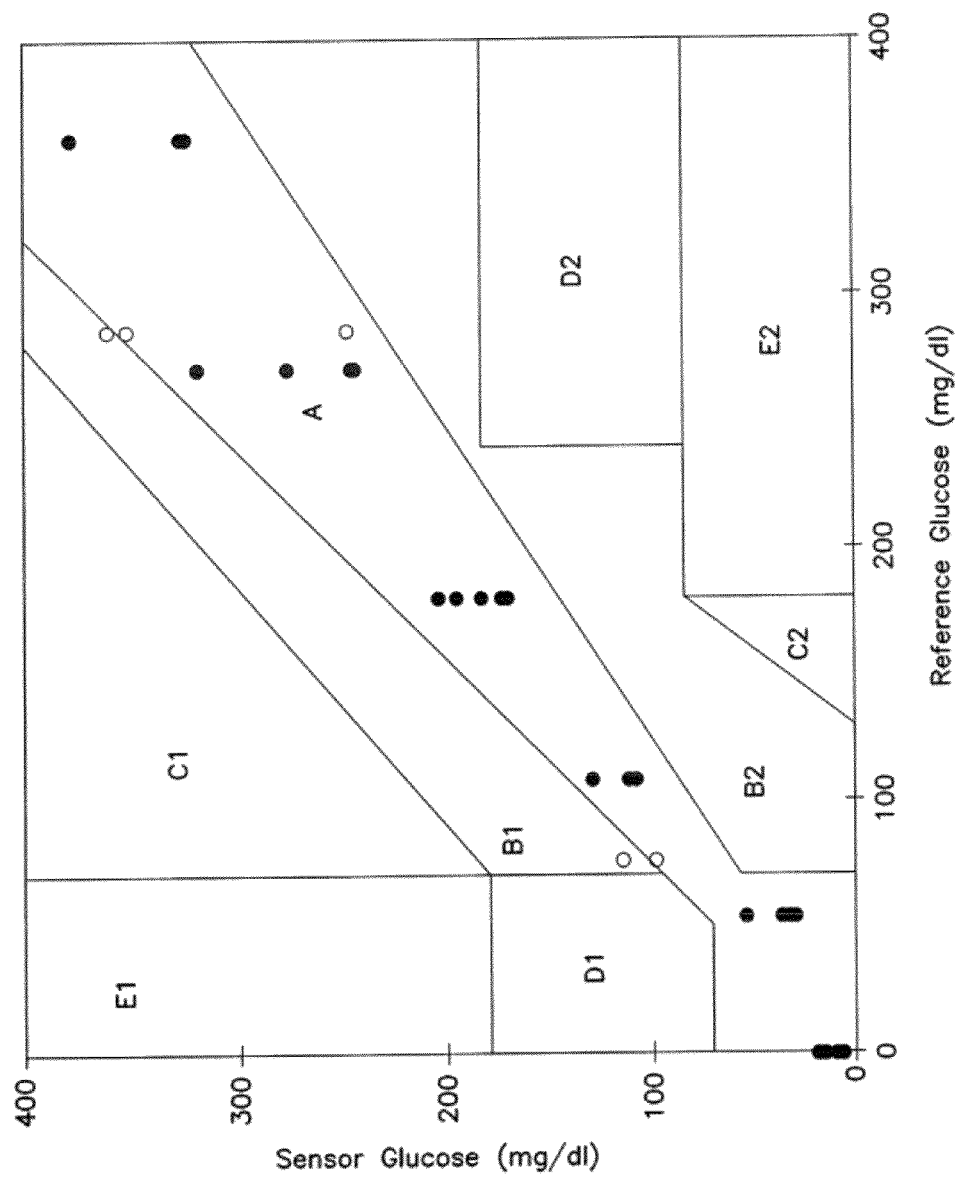
FIG. 9 is a Clarke-type clinical grid analyzing the clinical relevance of the glucose measurements of FIG. 7.

FIG. 9 shows the data of Table 1 plotted on an error grid developed by Clarke et al., *Diabetes Care*, 5, 622-27, 1987, for the determination of the outcome of errors based on inaccurate glucose concentration determination. The graph plots "true" glucose concentration vs. measured glucose concentration, where the measured glucose concentration is determined by calculating a glucose concentration using the calibration curves of FIG. 8 for each data point of FIG. 7. Points in zone A are accurate, those in zone B are clinically acceptable, and those in zones C, D, and E lead to increasingly inappropriate and finally dangerous treatments.

There were 34 data points. Of those data points 91% fell in zone A, 6% in zone B, and 3% in zone C. Only one reading was determined to be in zone C. This reading was off-scale and is not shown in FIG. 9. Thus, 97% of the readings fell in the clinically acceptable zones A and B.

The total number of Os atoms was determined by reducing all of the Os and then electrooxidizing it with a glucose-free buffer in the sample chamber. This resulted in a charge of 59.6±5.4 µC. Comparison of this result with the glucose-free buffer result in Table 1 indicated that less than 20% of the Os is in the reduced form prior to introduction of the sample. The variability in the quantity of osmium in the reduced state is less than 5% of the total quantity of osmium present.

Example 2

Response of the Glucose Sensor to Interferents

A sensor constructed in the same manner as described above for Example 1 was used to determine the sensor's response to interferents. The primary electrochemical interferents for blood glucose measurements are ascorbate, acetaminophen, and urate. The normal physiological or therapeutic (in the case of acetaminophen) concentration ranges of these common interferents are:
  ascorbate: 0.034-0.114 mM
  acetaminophen: 0.066-0.200 mM
  urate (adult male): 0.27-0.47 mM
Tietz, in: *Textbook of Clinical Chemistry*, C. A. Burtis and E. R. Ashwood, eds., W.B. Saunders Co., Philadelphia 1994, pp. 2210-12.

Buffered glucose-free interferent solutions were tested with concentrations of the interferents at the high end of the physiological or therapeutic ranges listed above. The injected sample volume in each case was 0.5 µL. A potential of +100 mV or +200 mV was applied between the electrodes. The average charge ($Q_{avg}$) was calculated by subtracting an average background current obtained from a buffer-only (i.e., interferent-free) solution from an average signal recorded with interferents present. The resulting average charge was compared with the signals from Table 1 for 4 mM and 10 mM glucose concentrations to determine the percent error that would result from the interferent.

TABLE 2

Interferent Response of Glucose Sensors

| Solution | E (mV) | n | $Q_{avg}$ (µC) | Error @ 4 mM glucose | Error @ 10 mM glucose |
|---|---|---|---|---|---|
| 0.114 mM ascorbate | 100 | 4 | 0.4 | 2% | <1% |
| 0.114 mM ascorbate | 200 | 4 | −0.5 | 2% | <1% |
| 0.2 mM acetaminophen | 100 | 4 | 0.1 | <1% | <1% |
| 0.2 mM acetaminophen | 200 | 4 | 1.0 | 5% | 1% |
| 0.47 mM urate | 100 | 4 | 6.0 | 30% | 7% |
| 0.47 mM urate | 200 | 4 | 18.0 | 90% | 21% |

These results indicated that ascorbate and acetaminophen were not significant interferents for the glucose sensor configuration, especially for low potential measurements. However, urate provided significant interference. This interference can be minimized by calibrating the sensor response to a urate concentration of 0.37 mM, e.g., by subtracting an appropriate amount of charge as determined by extrapolation from these results from all glucose measurements of the sensor. The resulting error due to a 0.10 mM variation in urate concentration (the range of urate concentration is 0.27-0.47 in an adult male) would be about 6% at 4 mM glucose and 100 mV.

Example 3

Sensor with Glucose Dehydrogenase

A sensor similar to that described for Example 1 was prepared and used for this example, except that glucose oxidase was replaced by pyrroloquinoline quinone glucose dehydrogenase and a potential of only +100 mV was applied as opposed to the +200 mV potential in Example 1. The results are presented in Table 3 below and graphed in FIG. 10.

TABLE 3

Sensor Results Using Glucose Dehydrogenase

|  | n | $Q_{avg}$ (µC) | 90% rise time (s) |
|---|---|---|---|
| buffer | 4 | 21.7 ± 5.2 | 14 ± 3 |
| 3 mM glucose/buffer | 4 | 96.9 ± 15.0 | 24 ± 6 |
| 6 mM glucose/buffer | 4 | 190.6 ± 18.4 | 26 ± 6 |
| 10 mM glucose/buffer | 4 | 327.8 ± 69.3 | 42 ± 9 |

The results indicated that the charge obtained from the glucose dehydrogenase sensor was much larger than for the comparable glucose oxidase sensor, especially for low concentrations of glucose. For 4 mM glucose concentrations the measurements obtained by the two sensors differed by a factor of five. In addition, the glucose dehydrogenase sensor operated at a lower potential, thereby reducing the effects of interferent reactions.

Figure 10:
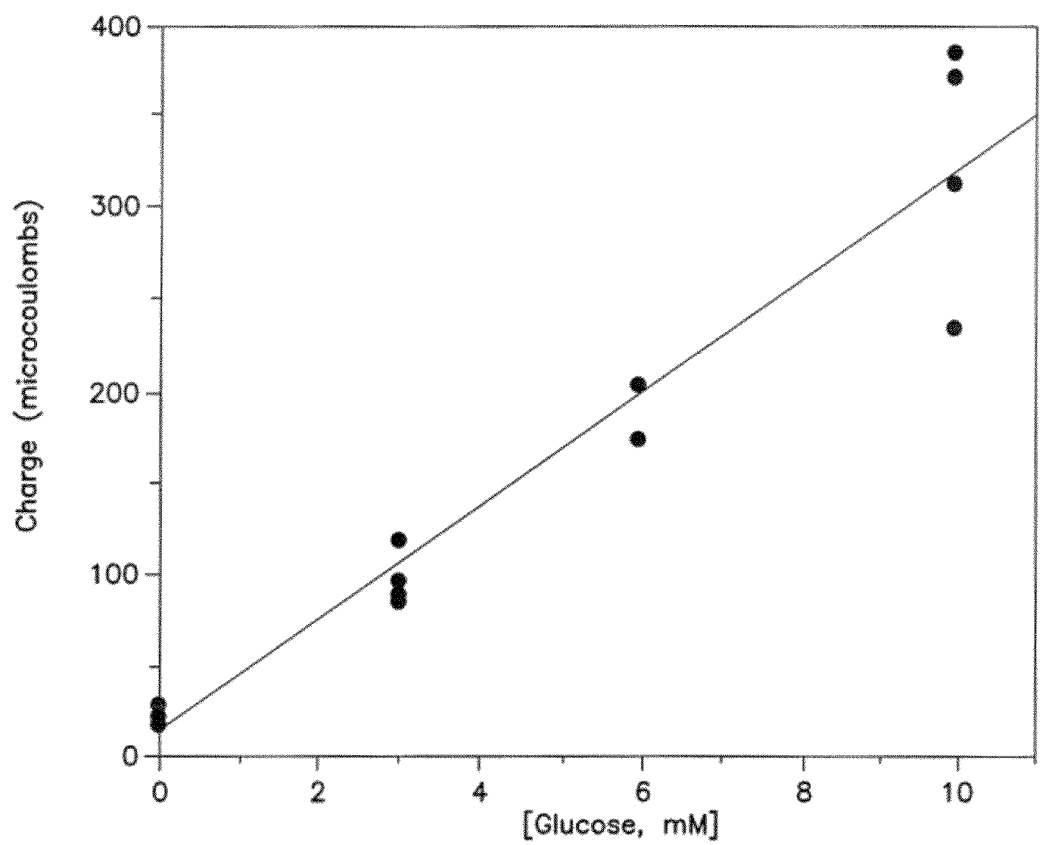
FIG. 10 is a graph of the charge required to electrooxidize a known quantity of glucose in an electrolyte buffered solution using the sensor of FIG. 1 with glucose dehydrogenase as the second electron transfer agent.

In addition, the results from Table 3 were all fit by a linear calibration curve as opposed to the results in Example 1, as shown in FIG. 10. A single linear calibration curve is greatly preferred to simplify sensor construction and operation.

Also, assuming that the interferent results from Table 2 are applicable for this sensor, all of the interferents would introduce an error of less than 7% for a 3 mM glucose solution at a potential of 100 mV.

Example 4

Determination of Lactate Concentration in a Fluid Stream

The sensor of this Example was constructed using a flow cell (BioAnalytical Systems, Inc. #MF-1025) with a glassy carbon electrode. A redox mediator was coated on the electrode of the flow cell to provide a working electrode. In this case, the redox mediator was a polymer formed by complexing poly(1-vinyl imidazole) with Os(4,4'-dimethyl-2,2'-bipyridine)$_2$Cl$_2$ with a ratio of 1 osmium for every 15 imidazole functionalities. Lactate oxidase was cross-linked with the polymer via polyethylene glycol diglycidyl ether. The mediator was coated onto the electrode with a coverage of 500 µg/cm$^2$ and a thickness of 5 µm. The mediator was covered by a polycarbonate track-etched membrane (Osmonics-Poretics #10550) to improve adherence in the flow stream. The membrane was then overlaid by a single 50 µm thick spacer gasket (BioAnalytical Systems, Inc. #MF-1062) containing a void which defined the sample chamber and corresponding measurement zone. Assembly of the sensor was completed by attachment of a cell block (BioAnalytical Systems, Inc. #MF-1005) containing the reference and auxiliary electrodes of the flow cell.

The sample chamber in this case corresponded to a 50 µm thick cylinder (the thickness of the spacer gasket) in contact with a mediator-coated electrode having a surface area of 0.031 cm$^2$. The calculated volume of sample in the measurement zone of this sensor was approximately 0.16 µL.

The flow rate of the fluid stream was 5 µL/min. A standard three electrode potentiostat was attached to the cell leads and a potential of +200 mV was applied between the redox mediator-coated glassy carbon electrode and the reference electrode. This potential was sufficient to drive the enzyme-mediated oxidation of lactate.

As the fluid stream flowed through the sensor, a steady-state current proportional to the lactate concentration was measured. At periodic intervals the fluid flow was stopped and current was allowed to flow between the electrodes until approximately all of the lactate in the measurement zone was electrooxidized, as indicated by the achievement of a stabilized, steady-state current. The total charge, Q, required for lactate electrooxidation was found by integration of the differential current registered from the flow stoppage until the current reached a steady-state. The concentration was then calculated by the following equation:

$$[lactate] = Q/2FV \quad (4)$$

where V is the volume of sample within the measurement zone and F is Faraday's constant.

This assay was performed using lactate solutions having nominal lactate concentrations of 1.0, 5.0, and 10.0 mM. The measured concentrations for the assay were 1.9, 5.4, and 8.9 mM respectively.

Example 5

Determination of the Oxidation State of Os(4,4'-dimethoxy-2,2'-bipyridine)$_2$Cl$^{+/+2}$ Complexed with poly(1-vinyl imidazole)

A sensor having a three electrode design was commercially obtained from Ecossensors Ltd., Long Hanborough, England, under the model name "large area disposable electrode". The sensor contained parallel and coplanar working, reference and counter electrodes. The working surface area (0.2 cm$^2$) and counter electrodes were formed of printed carbon and the reference electrode was formed of printed Ag/AgCl. A redox mediator was coated on the carbon working electrode. The redox mediator was formed by complexation of poly(1-vinyl imidazole) with Os(4,4'-dimethoxy-2, 2'-bipyridine)$_2$Cl$_2$ in a ratio of 15 imidazole groups per Os cation followed by cross linking the osmium polymer with glucose oxidase using polyethylene glycol diglycidyl ether.

The electrode was cured at room temperature for 24 hours. The coplanar electrode array was then immersed in a buffered electrolyte solution, and a potential of +200 mV (sufficient for conversion of Os(II) to Os(III),) was applied between the working electrode and the reference electrode.

Upon application of the potential, an undetectable charge of less than 1 µC was passed. Subsequent reduction and reoxidation of the redox mediator yielded a charge for conversion of all Os from Os(II) to Os(III) of 65 µC. Therefore, more than 98% of the Os cations in the redox mediator were in the desired oxidized Os(III) state.

Example 6

Determination of the Oxidation State of the Os(4,4'-dimethoxy-2,2'-bipyridine)$_2$Cl$^{+/+2}$ Complexed with poly(4-vinyl pyridine)

A similar experiment to that of Example 5 was conducted with the same working/counter/reference electrode configuration except that the redox mediator on the working electrode was changed to a complex of Os(4,4'-dimethoxy-2,2'-bipyridine)$_2$Cl$_2$ with poly(4-vinyl pyridine), with 12 pyridine groups per Os cation, cross linked with glucose oxidase via polyethylene glycol diglycidyl ether.

Two sensors were constructed. The electrodes of the two sensors were cured at room temperature for 24 hours. The electrodes were then immersed in a buffered electrolyte solution and a potential of +200 mV was applied between the working and reference electrodes.

Upon application of the potential to the electrodes, a charge of 2.5 µC and 3.8 µC was passed in the two sensors, respectively. Subsequent reduction and reoxidation of the redox mediators yielded oxidation charges of 27.9 µC and 28.0 µC, respectively. Therefore, the sensors originally contained 91% and 86% of the Os cations in the desirable oxidized Os(III) state.

Example 7

Optical Sensor

An optical sensor is constructed by applying a film of redox polymer with crosslinked enzyme onto a light-transparent support such as a glass slide. The quantity of redox mediator is equal to or greater than (in a stoichiometric sense) the maximum quantity of analyte expected to fill the measurement zone. The spacer material, sorbent and facing support are securely clamped. The sample chamber is adapted to transmit light through the assembled sensor to an optical density detector or to a luminescence and/or fluorescence detector. As sample fills the sample chamber and the redox mediator is oxidized, changes in the absorption, transmission, reflection or luminescence and/or fluorescence of the redox mediator in the chamber are correlated to the amount of glucose in the sample.

Example 8

Blood Volumes from Upper Arm Lancet Sticks

The forearm of a single individual was pierced with a lancet multiple times in order to determine the reproducibility of blood volumes obtained by this method. Despite more than thirty lancet sticks in the anterior portion of each forearm and the dorsal region of the left forearm, the individual identified each stick as virtually painless.

The forearm was pierced with a Payless Color Lancet. The blood from each stick was collected using a 1 µL capillary tube, and the volume was determined by measuring the length of the blood column. The volumes obtained from each stick are shown below in Table 4.

TABLE 4

| Volume of Lancet Sticks | | | |
|---|---|---|---|
| | Left Anterior Forearm, (nL) | Right Anterior Forearm, (nL) | Left Dorsal Forearm, (nL) |
| 1 | 180 | 190 | 180 |
| 2 | 250 | 180 | 300 |
| 3 | 170 | 120 | 310 |
| 4 | 150 | 100 | 300 |
| 5 | 100 | 210 | 60 |
| 6 | 50 | 140 | 380 |
| 7 | 90 | 120 | 220 |
| 8 | 130 | 140 | 200 |
| 9 | 120 | 100 | 380 |
| 10 | | 100 | 320 |
| 11 | | | 260 |
| 12 | | | 250 |
| 13 | | | 280 |
| 14 | | | 260 |
| Avg. | 138 ± 58 nL | 140 ± 40 nL | 264 ± 83 nL |

Example 9

A Sensor with Diffusible Redox Mediator

A sensor was formed by printing graphite ink (Graphite #G4491, Ercon, Wareham, Mass.) on a polyester substrate. A mixture of 5.5 µg/cm$^2$ [Os(dimethyoxybipyridine)$_2$(vinylimidazole)Cl]Cl, 23.7 µg/cm$^2$ PQQ-glucose dehydrogenase, and 18.2 µg/cm$^2$ Zonyl FSO® surfactant (E. I. duPont de Nemours & Co., Inc., Wilmington, Del.) were deposited on a portion of the working electrode. A 150 µm thick pressure sensitive adhesive tape was then applied to the working electrode leaving only a portion of the working electrode exposed to form a sample chamber. A second polyester film with a counter electrode disposed on the film was provided over the pressure sensitive adhesive tape. The counter electrode was formed by disposing Ag/AgCl ink (Silver/Silver Chloride #R414, Ercon, Wareham, Mass.) over the second polyester film. The Ag/AgCl counter electrode was coated with approximately 100 µg/cm$^2$ of methylated poly(vinylimidazole) crosslinked using PEGDGE.

Example 10

Figure 15:
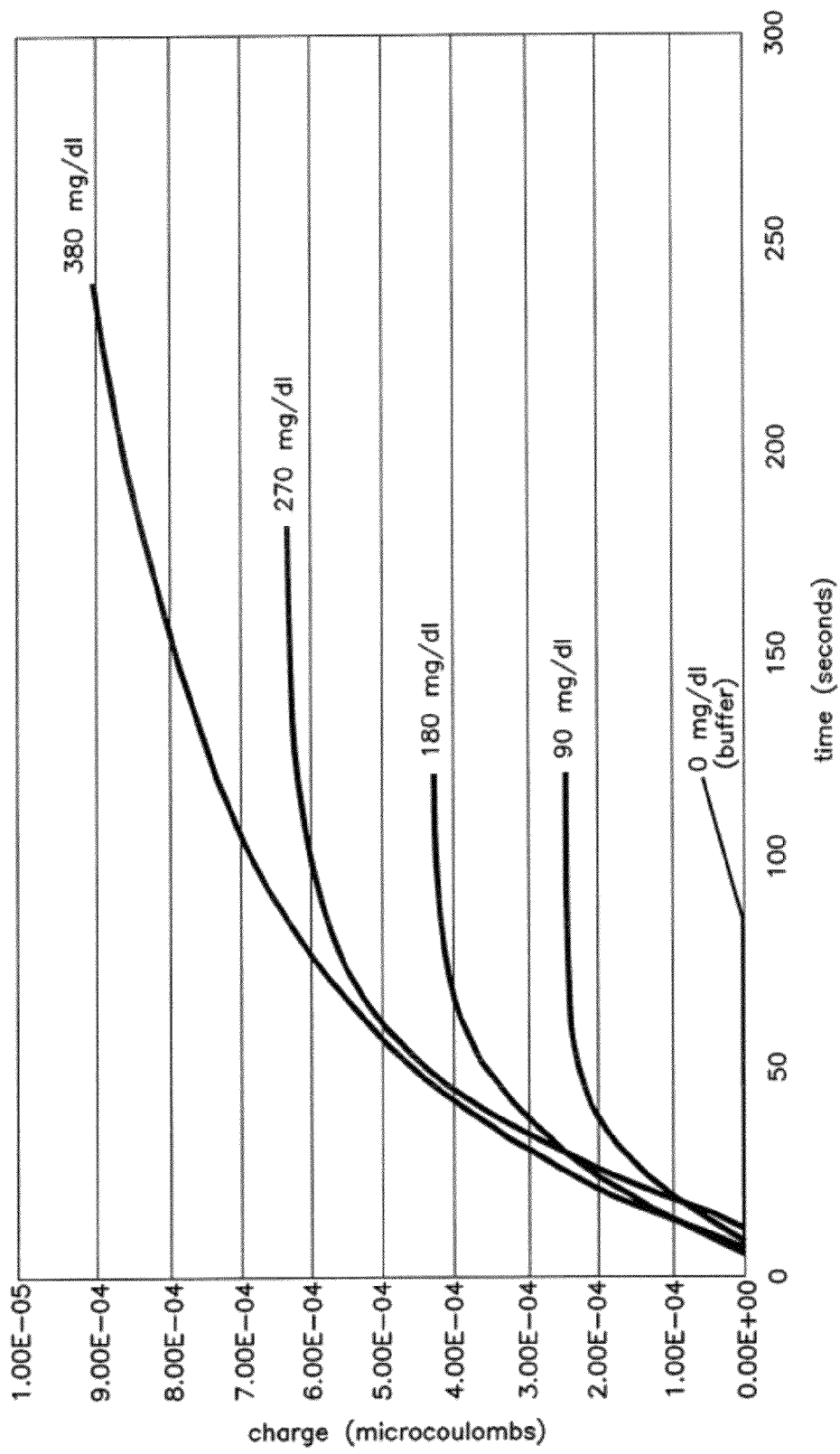
FIG. 15 is a graph of charge delivered by a sensor having a diffusible redox mediator over time for several concentrations of glucose.
Figure 16:
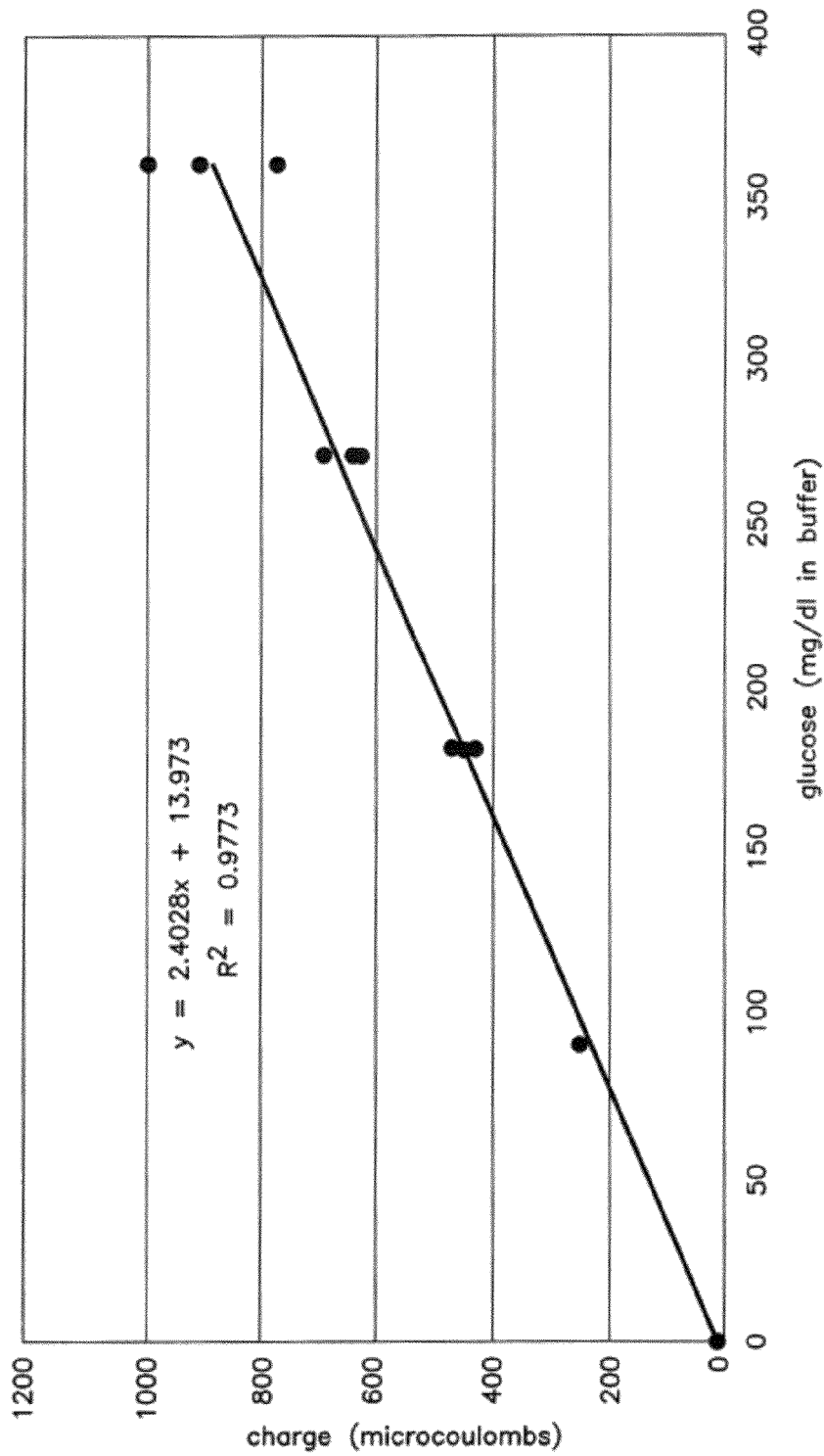
FIG. 16 is a graph of charge delivered by a sensor having a diffusible redox mediator for several glucose concentrations.

Measuring Glucose Using Sensor with Diffusible Redox Mediator at a Potential of 0 V Sensors were formed as described in Example 9 and used to measure glucose/buffer solutions at 0, 90, 180, 270, and 360 mg/dL glucose concentration. The charge measured over time for each of these solutions is graphed in FIG. 15. In the absence of glucose, the sensor indicates about 3 mg/dL glucose concentration. FIG. 16 illustrates the measured charge versus glucose concentration for three sensors at each glucose concentration. The measured charge varies linearly with glucose concentration similar to what is observed for sensors using non-leachable redox mediator.

Example 11

Other Sensors Formed Using Diffusible Redox Mediator

Sensors A and B were formed by printing graphite ink (Graphite #G4491, Ercon, Wareham, Mass.) on a polyester substrate. For Sensor A, a mixture of 8.0 µg/cm$^2$ [Os(dimethyoxybipyridine)$_2$(vinyl imidazole)Cl]Cl, 34.7 µg/cm$^2$ PQQ-glucose dehydrogenase, and 26.6 µg/cm$^2$ Zonyl FSO® surfactant (E.I. duPont de Nemours & Co., Inc., Wilmington, Del.) were deposited on a portion of the working electrode. For Sensor B, a mixture of 24 µg/cm$^2$ [Os(dimethyoxybipyridine)$_2$(vinyl imidazole)Cl]Cl, 104 µg/cm$^2$ PQQ-glucose dehydrogenase, and 80 µg/cm$^2$ Zonyl FSO® surfactant (E.I. duPont de Nemours & Co., Inc., Wilmington, Del.) were deposited on a portion of the working electrode. A 200 µm pressure sensitive adhesive tape was then formed over the working electrode of each sensor leaving only a portion of the working electrode exposed to form a sample chamber. A second polyester film with a counter electrode disposed on the film was provided over the pressure sensitive adhesive tape. The counter electrode of each sensor was formed by disposing Ag/AgCl ink (Silver/Silver Chloride #R414, Ercon, Wareham, Mass.) over the second polyester film. The Ag/AgCl counter electrode was coated with approximately 100 µg/cm$^2$ of methylated poly(vinylimidazole) crosslinked using PEGDGE.

Example 12

Varying the Amount of Diffusible Redox Mediator in the Sensor

Figure 17:
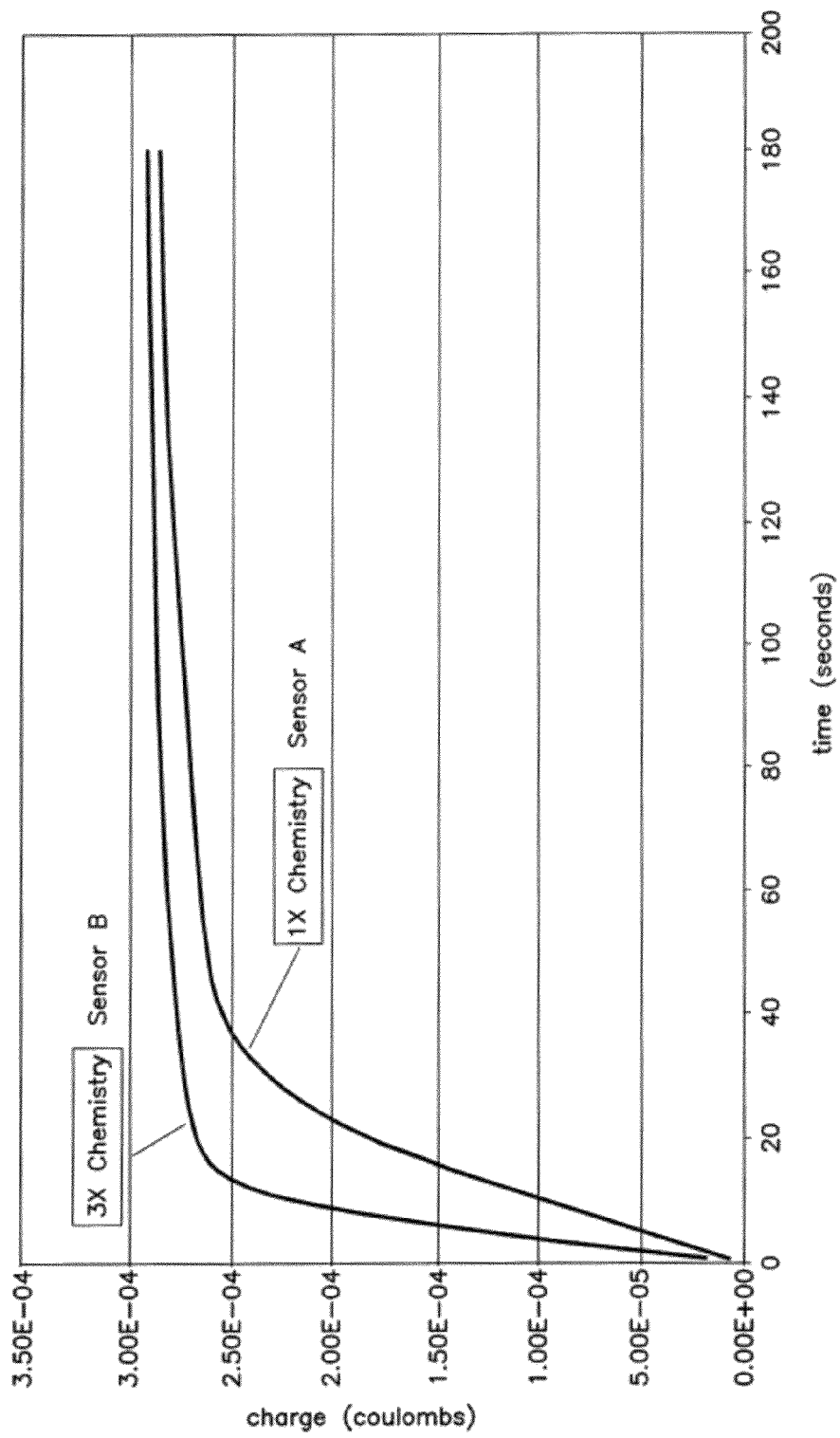
FIG. 17 is a graph of charge delivered by sensors with different amounts of diffusible redox mediator over time.

Sensors A and B were each tested to determine the amount of time required for electrolysis of the analyte. FIG. 17 illustrates the results. Increasing the amount of diffusible redox mediator in the sample decreases the response time of the sensor.

Example 13

Clinical Accuracy of the Small Volume Sensor

The sensor of this Example was constructed corresponding to the embodiment of the invention depicted in FIGS. 24A, 24B, and 24C. The carbon working electrode was printed on a Melinex™ polyester film (DuPont, Wilmington, Del.), as described in Example 11. The carbon electrode was coated with 18 µg/cm$^2$ Os[(MeO)$_2$bpy]$_2$(1-vinyl imidazole)Cl$_3$, 162 µg/cm$^2$ GDH (Toyobo, Japan), 1.35 µg/cm$^2$ PQQ (Fluka, Mila, Wis.), and 60 μg/cm² Zonyl FSO (DuPont, Wilmington, Del.). The coatings were applied to the working electrode at 18° C. and in 50% relative humidity. An adhesive (50 μm thickness) was placed on the carbon electrode surrounding the coated surface and forming a channel having a width of about 0.04 inches.

Two Ag/AgCl counter/reference electrodes were printed on a second Melinex™ polymer film, as described in Example 11. The film was then brought into contact with the adhesive and the working electrode film so that the working electrode and two counter electrodes were facing each other. The counter/reference electrodes were coated with 142 μg/cm² methylated polyvinyl imidazole, 18 μg/cm² PEGDGE (PolySciences, Warington, Pa.), and 7 μg/cm²Zonyl FSO (DuPont, Wilmington, Del.). One of the counter electrodes, upstream of the other counter electrode, was used as an indicator electrode to determine when the sample chamber was full. The sensors were laminated by three passes with a hand roller and aged for three days at room temperature over $CaSO_4$.

The sensors were constructed so that when sufficient current flowed between indicator and counter/reference electrodes, an external circuit emitted a visual signal indicating that the channel overlying the working electrode was full of blood.

A few days prior to using the sensors, dry capacitance measurements were taken to determine the uniformity of the sample chamber volume. The variation in capacitance reflected misalignment of electrodes and/or variation in adhesive thickness. The mean capacitance measured was 7.49 pF with a standard deviation of 0.28 pF or 3.8%. The maximum capacitance measured was 8.15 pF and the minimum capacitance measured was 6.66 pF.

The sensors were used to determine the glucose concentration in blood samples obtained from 23 people. In the study, the people ranged from 26 to 76 years of age, fourteen were men, and nine were women. Six of the people were diagnosed with Type 1 diabetes, sixteen were diagnosed with Type 2 diabetes, and one person was unknown regarding diabetic status. The people studied had an average hematocrit of 40.7% with a standard deviation of 3.9%. The maximum hematocrit was 49% and the minimum hematocrit was 33.2%.

One blood sample for each person was collected by pricking the finger of the subject. A small volume sensor was filled with this residual blood.

Three blood samples for each person were then collected in small volume sensors by using a 2 mm Carelet™ to lance the arm. If an adequate sample was not obtained in 10 seconds, the area around the puncture wound was kneaded, and then the sensor was filled. Sixteen of the sixty-nine samples required that the wound be kneaded.

Three blood samples per person were collected by venipuncture. YSI blood glucose measurements and hematocrit measurements were taken on at least one sample. Forty-six small volume sensors were also filled with blood from these samples.

Measurements from the sensor were performed at an applied potential of 0 mV. BAS potentiostats (CV50W, West Lafayette, Ind.) were "on" before any sample was applied, so that as the strips filled, electrolysis was immediate. Current collection was for 150 seconds (this charge is termed "complete" electrolysis), although most assays were essentially complete well before 150 seconds. No results were discarded. Three successive sensor blood glucose measurements were taken.

Measurements for the control samples were performed using YSI blood glucose measurement (Yellow Springs Instruments, Model 2300 Chemical Glucose Analyzer).

The data was plotted against YSI venous results and a linear function was determined from the data. All data was collected from "complete" (150 second) electrolysis of glucose in the sensor.

Figure 28:
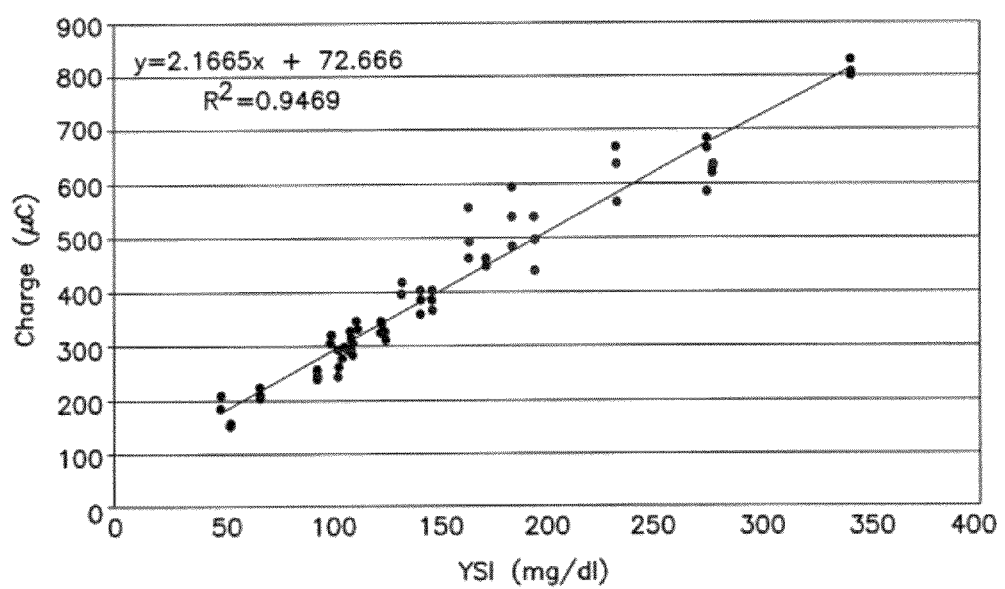
FIG. 28 illustrates a graph comparing measurements of analyte concentration in blood samples collected from a subject's arm made by a sensor of the invention with those determined by a standard blood test.

FIG. 28 shows the data for 69 small volume sensors tested on blood obtained from the arm. $R^2$ was 0.947, the average CV (coefficient of variation) was 4.8%, and the RMS (root mean square) CV was 5.7%.

Figure 29:
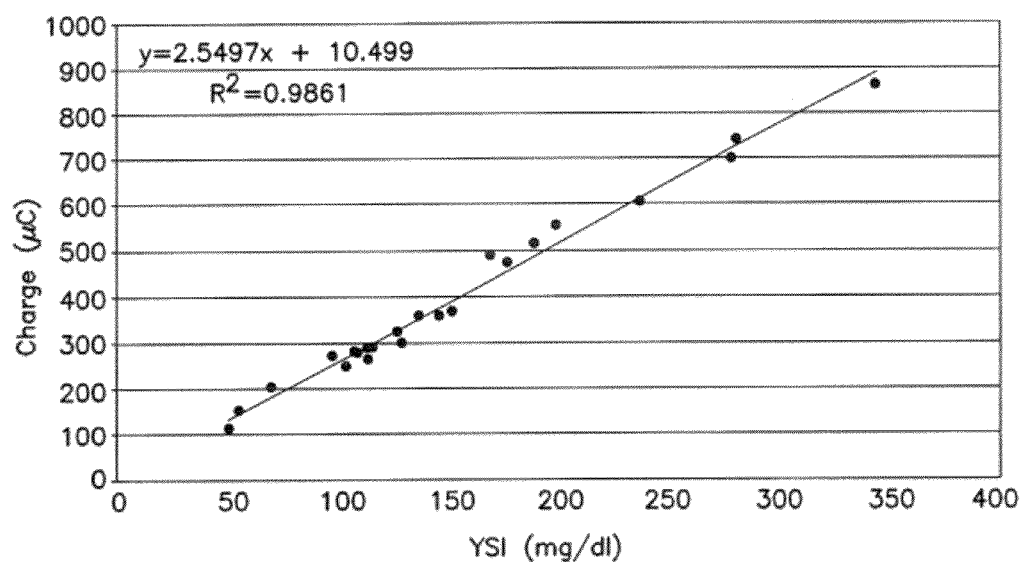
FIG. 29 illustrates a graph comparing measurements of analyte concentration in blood samples collected from a subject's finger made by a sensor of the invention with those determined by a standard blood test.

FIG. 29 shows the data for 23 small volume sensors tested on blood obtained from the finger. $R^2$ was 0.986.

Figure 30:
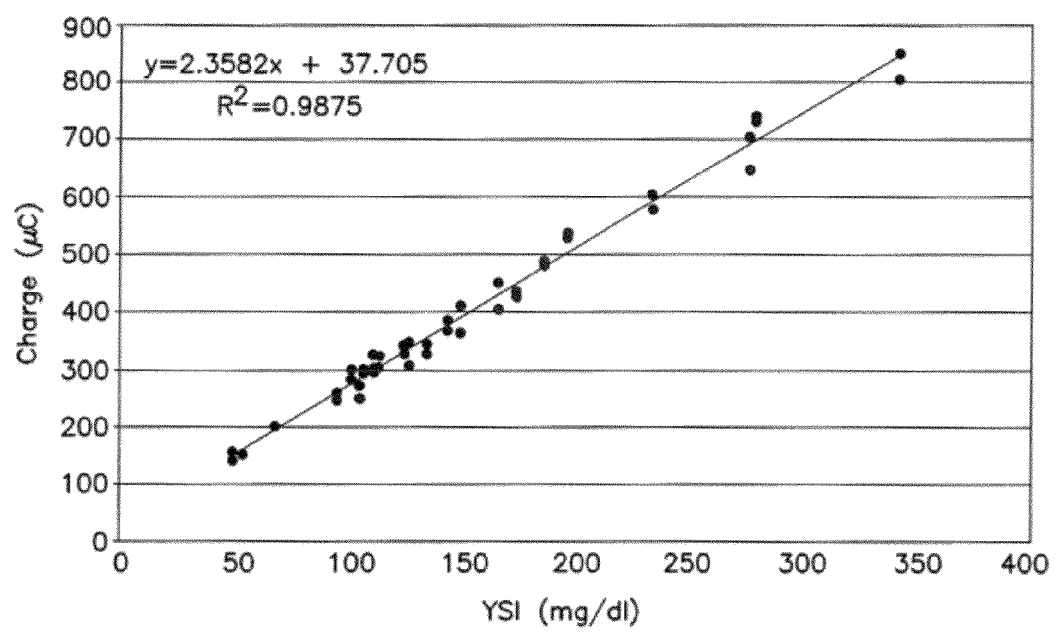
FIG. 30 illustrates a graph comparing measurements of analyte concentration in venous samples made by a sensor of the invention with those determined by a standard blood test.

FIG. 30 shows the data for 46 small volume sensors tested on venous blood. $R^2$ was 0.986. The average CV was 3.8%. The RMS CV was 4.6%.

The invention has been described with reference to various specific and preferred embodiments and techniques. However, it will be apparent to one of ordinarily skill in the art that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually incorporated by reference.

We claim:

1. A method for determining a concentration of an analyte in a sample, comprising the steps of:
    contacting a sample with a sensor, wherein the sensor comprises:
        a working electrode and a counter electrode, wherein the working electrode and counter electrode are separated by an effective distance in a range of 25 to 1000 μm;
        a sample chamber for holding the sample fluid, the sample chamber comprising the working electrode, the counter electrode, a first indicator electrode to indicate when the sample chamber is beginning to fill with sample, and a second indicator electrode to indicate when the sample chamber is substantially filled with sample, wherein the sample chamber is sized to contain a volume of no more than about 1 μL of the sample; and
        an analyte-responsive enzyme and a diffusible redox mediator disposed in the sample chamber, which redox mediator is non-immobilized wherein a background signal generated by the diffusible redox mediator in the absence of the analyte is no more than 25% of the signal generated by oxidation or reduction of the average normal physiological amount of analyte;
    observing a signal from the first indicator electrode to signify that the sample chamber is beginning to fill with sample;
    observing a signal from the second indicator electrode to signify that the sample chamber is substantially filled with sample;
    generating a sensor signal at the working electrode, and determining the concentration of the analyte by coulometry using the sensor signal.

2. The method according to claim 1, wherein the background signal that is generated by the diffusible redox mediator in the absence of the analyte is no more than 5% of the signal generated by oxidation or reduction of the average normal physiological amount of analyte.

3. The method according to claim 1, further comprising:
providing calibration data on a batch of the electrochemical sensors to a measurement instrument, said calibration data comprising information related to a magnitude of a background charge for the batch of the electrochemical sensors;
wherein the step of determining the concentration of the analyte comprises determining the concentration of the analyte using the sensor signal and the calibration data.

4. The method according to claim 1, wherein the sensor comprises:
(a) a first substrate having a proximal end and a distal end, the first substrate defining a first side edge and a second side edge of the electrochemical sensor extending from the proximal end to the distal end of the first substrate, the distal end being configured and arranged for insertion into a sensor reader;
(b) a second substrate disposed over the first substrate, the working electrode being disposed on one of the first and second substrates and the counter electrode being disposed on one of the first and second substrates;
(c) a spacer disposed between the first and second substrates and defining a first aperture along the first side edge of the sensor and a second aperture along the second side edge of the sensor, the sample chamber extending from the first aperture to the second aperture; and
(d) the first and second indicator electrodes disposed on at least one of the first and second substrates and positioned relative to the sample chamber to determine when the sample chamber is beginning to fill with sample and when the sample chamber is substantially filled with sample.

5. The method according to claim 1, wherein the sensor comprises:
(a) a first substrate having a proximal end and a distal end, the distal end being configured and arranged for insertion into a sensor reader, the first substrate defining a first side edge and a second side edge of the electrochemical sensor extending from the proximal end to the distal end of the first substrate;
(b) a second substrate disposed over the first substrate, the working electrode being disposed on one of the first and second substrates and the counter electrode being disposed on one of the first and second substrates;
(c) a spacer disposed between the first and second substrates and defining a first aperture along the proximal end of the sensor and a second aperture along the first side edge of the sensor, the sample chamber extending from the first aperture to the second aperture; and
(d) the first and second indicator electrodes disposed on at least one of the first and second substrates and positioned relative to the sample chamber to determine when the sample chamber is beginning to fill with sample and when the sample chamber is substantially filled with sample.

6. The method according to claim 1, wherein the sensor further comprises a visual or auditory sign coupled to the second indicator electrode that activates when the indicator electrode indicates that the sample chamber contains sample.

7. The method according to claim 1, wherein the indicator electrodes are disposed in facing relationship to one of the working electrode and the counter electrode.

8. The method according to claim 1, wherein either the working electrode or the counter electrode is disposed between the two indicator electrodes.

9. The method according to claim 1, wherein at least a portion of the working electrode is within an effective distance of no more than 200 µm of a portion of the counter electrode.

10. The method according to claim 1, wherein the analyte is glucose.

11. The method according to claim 10, wherein the analyte-responsive enzyme is a glucose dehydrogenase.

12. A method for determining a concentration of an analyte in a sample, the method comprising the steps of:
contacting a sample with a sensor, wherein the sensor comprises:
an electrode pair comprising a working electrode, and a counter electrode, wherein the working electrode and counter electrode are separated by an effective distance in a range of 25 to 1000 µm;
a sample chamber for holding the sample fluid, the sample chamber comprising the working electrode, the counter electrode, a first indicator electrode to indicate when the sample chamber is beginning to fill with sample, and a second indicator electrode to indicate when the sample chamber is substantially filled with sample, wherein the sample chamber is sized to contain a volume of no more than about 1 µL of the sample; and
an analyte-responsive enzyme and a diffusible redox mediator disposed in the sample chamber, which redox mediator is non-immobilized, wherein a background signal generated by the diffusible redox mediator in the absence of the analyte is no more than 25% of the signal generated by oxidation or reduction of the average normal physiological amount of analyte;
observing a signal from the first indicator electrode to signify that the sample chamber is beginning to fill with sample;
observing a signal from the second indicator electrode to signify that the sample chamber is substantially filled with sample;
applying a potential between the working electrode and the counter electrode to electrolyze the analyte in the sample;
generating an analyte-responsive signal from the sensor in response to electrolysis of the analyte in the sample; and
determining the concentration of the analyte by coulometry using the analyte-responsive signal.

13. The method according to claim 12, wherein the sensor comprises:
(a) a first substrate having a proximal end and a distal end, the first substrate defining a first side edge and a second side edge of the electrochemical sensor extending from the proximal end to the distal end of the first substrate, the distal end being configured and arranged for insertion into a sensor reader;
(b) a second substrate disposed over the first substrate, the working electrode being disposed on one of the first and second substrates and the counter electrode being disposed on one of the first and second substrates;
(c) a spacer disposed between the first and second substrates and defining a first aperture along the first side edge of the sensor and a second aperture along the second side edge of the sensor, the sample chamber extending from the first aperture to the second aperture; and
(d) the first and second indicator electrodes disposed on at least one of the first and second substrates and positioned relative to the sample chamber to determine when the sample chamber is beginning to fill with sample and when the sample chamber is substantially filled with sample.

14. The method according to claim 12, wherein the sensor comprises:
   (a) a first substrate having a proximal end and a distal end, the distal end being configured and arranged for insertion into a sensor reader, the first substrate defining a first side edge and a second side edge of the electrochemical sensor extending from the proximal end to the distal end of the first substrate;
   (b) a second substrate disposed over the first substrate, the working electrode being disposed on one of the first and second substrates and the counter electrode being disposed on one of the first and second substrates;
   (c) a spacer disposed between the first and second substrates and defining a first aperture along the proximal end of the sensor and a second aperture along the first side edge of the sensor, the sample chamber extending from the first aperture to the second aperture; and
   (d) the first and second indicator electrodes disposed on at least one of the first and second substrates and positioned relative to the sample chamber to determine when the sample chamber is beginning to fill with sample and when the sample chamber is substantially filled with sample.

15. The method according to claim 12, wherein the sensor further comprises a visual or auditory sign coupled to the second indicator electrode that activates when the indicator electrode indicates that the sample chamber contains sample.

16. The method according to claim 12, wherein the indicator electrodes are disposed in facing relationship to one of the working electrode and the counter electrode.

17. The method according to claim 12, wherein either the working electrode or the counter electrode is disposed between the two indicator electrodes.

18. The method according to claim 12, wherein at least a portion of the working electrode is within an effective distance of no more than 200 µm of a portion of the counter electrode.

19. The method according to claim 12, wherein the analyte is glucose.

20. The method according to claim 19, wherein the analyte-responsive enzyme is a glucose dehydrogenase.

* * * * *